United States Patent [19]

Ikawa et al.

[11] Patent Number: 5,696,268

[45] Date of Patent: Dec. 9, 1997

[54] 1,4-DIHYDROPYRIDINE DERIVATIVES AND METHODS OF PRODUCING THE SAME

[75] Inventors: Hiroshi Ikawa; Akiyoshi Kadoiri; Yasuko Konagai; Tetsuaki Yamaura; Noriko Kase, all of Tokyo, Japan

[73] Assignee: Fujirebio Inc., Tokyo, Japan

[21] Appl. No.: 460,273

[22] Filed: Jun. 2, 1995

Related U.S. Application Data

[62] Division of Ser. No. 258,487, Jun. 10, 1994, which is a division of Ser. No. 800,249, Nov. 29, 1991, Pat. No. 5,367,081.

[30] Foreign Application Priority Data

Nov. 30, 1990 [JP] Japan ................... 2-330005
Jul. 25, 1991 [JP] Japan ................... 3-207283
Jul. 25, 1991 [JP] Japan ................... 3-207284

[51] Int. Cl.⁶ ............ C07D 401/04; C07D 211/84; C07D 213/56
[52] U.S. Cl. ............ 546/249; 544/124; 544/269; 544/333; 544/405; 544/360; 546/144; 546/167; 546/193; 546/268.7; 546/269.1; 546/277.4; 546/280.4; 546/283.4; 546/316
[58] Field of Search ............... 546/316, 249, 546/144, 167, 193, 268.7, 269.1, 277.4, 280.4, 283.4; 544/405, 333, 360, 269, 124

[56] References Cited

U.S. PATENT DOCUMENTS 5,276,150  1/1994  Ikawa et al. ............... 544/238

*Primary Examiner*—Alan L. Rotman
*Attorney, Agent, or Firm*—Oblon, Spivak, McClelland, Maier & Neustadt, P.C.

[57] ABSTRACT 1,4-dihydropyridine derivatives and optically active 1,4-dihydropyridine derivatives with the following formula, having vasodilating activity based on calcium antagonism, and PAF antaognism, and methods of producing the same are disclosed:

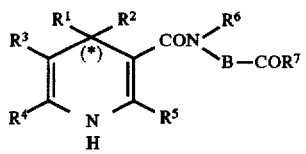

wherein (*) indicates a chiral center in the case of the optically active 1,4-dihydropyridine derivatives.

9 Claims, No Drawings

1,4-DIHYDROPYRIDINE DERIVATIVES AND METHODS OF PRODUCING THE SAME

This is a Division of application Ser. No. 08/258,487 filed on Jun. 10, 1994, pending; which is a Divisional of Ser. No. 07/800,249, filed Nov. 29, 1991, now U.S. Pat. No. 5,367,081.

BACKGROUND OF THE INVENTION

The present invention relates to 1,4-dihydropyridine derivatives and optically active 1,4-dihydropyridine derivatives having (a) vasodilating activity based on calcium antagonism and (b) PAF antaognism, and methods of producing the optically active 1,4-dihydropyridine derivatives.

Generally it is known that 1,4-dihydropyridine derivatives are useful as remedies for diseases of circulatory system such as remedies for ischemic heart disease, cerebral circulatory disease and hypertension, since the 1,4-dihydropyridine derivatives have vasodilating activity based on the calcium antagonism thereof.

It has been reported that it is essential that the 1,4-dihydropyridine derivatives have a 3,5-diester structure in order that the 1,4-dihydropyridine derivatives exhibit the above-mentioned actions.

Representative examples of such 1,4-dihydropyridine derivatives are 1,4-dihydro-2,6-dimethyl-4-(2-nitrophenyl) pyridine-3,5-dicarboxylic acid dimethyl ester (Generic name: "NIFEDIPINE" as described in U.S. Pat. No. 3,644,627) and 1,4-dihydro-2,6-dimethyl-4-(3-nitrophenyl) pyridine-3,5-dicarboxylic acid-3-[2-(N-benzyl-N-methylamino)ethyl]ester-5-methyl ester hydrochloride (Generic name: "NICARDIPINE" as described in Japanese Patent Publication 55-45075).

Furthermore, as the conventional methods of producing optically active 1,4-dihydropyridine-3-carboxylate derivatives, there are known, for instance, (a) a method comprising the steps of subjecting 1,4-dihydropyridine-3-carboxylic acid derivatives to optical resolution to obtain optically active 1,4-dihydropyridine-3-carboxylic acid derivatives, (refer to T. Shibanuma et al., Chem. Pharm. Bull. 28, 2809 (1980)) to 1,4-dihydropyridine-3,5-dicarboxylate derivatives and (b) a method of subjecting diastereomers of 1,4-dihydropyridine-3,5-dicarboxylate derivatives to optical resolution (refer to Japanese Laid-Open Patent Application 56-36455).

Platelet-activating factor (PAF) is produced by many types of pre-phlogocytes, platelet and liver, liberated, and exhibits not only strong platelet aggregation activity, but also biological activities in a wide range, which are induced directly or through the liberation of other strong mediators such as thromboxane $A_2$ and leucotriene. Therefore it is considered that compounds having PAF antagonism are useful for remedies for varieties of allergic diseases, inflammatory diseases, and hyperexcretory diseases, such as asthma, arthritis, and bronchitis. Furthermore, recent studies have revealed that PAF is capable of inducing the reduction of the blood flow volume of coronaory artery. Therefore it is also considered that PAF antagonists will be useful as remedies for angina pectoris.

As PAF antagonists, varieties of compounds such as PAF analogues and benzodiazepine derivatives has been reported.

However, a compound having (a) vasodilating activity based on calcium antagonism and (b) PAF antaognism have not yet been discovered.

SUMMARY OF THE INVENTION

It is therefore a first object of the present invention to provide 1,4-dihydropyridine derivatives having vasodilating activity based on calcium antagonism, and PAF antaognism.

A second object of the present invention is to provide optically active 1,4-dihydropyridine derivatives having vasodilating activity based on calcium antagonism, and PAF antaognism.

A third object of the present invention is to provide methods of producing the above 1,4-dihydropyridine derivatives and optically active 1,4-dihydropyridine derivatives.

The present invention is besed on the discovery that 1,4-dihydropyridine derivatives in which various amino acid derivatives are amido-bonded to either the position 3 or position 5 or both positions of the 1,4-dihydropyridine ring exhibit antihypertensive action or PAF antagonism the same as or greater than that exhibited by the conventional 1,4-dihydropyridine-3,5-diester derivatives.

The first object of the present invention is achieved by 1,4-dihydropyridine derivatives of formula (I):

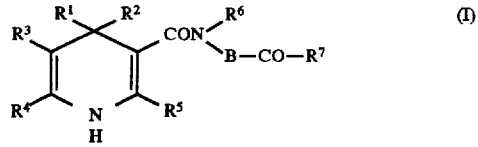

wherein $R^1$ represents hydrogen, a straight chain, branched chain or cyclic alkyl group, an unsubstituted or substituted aromatic hydrocarbon group, or an unsubstituted or substituted aromatic heterocyclic group; $R^2$ represents hydrogen, a straight chain, branched chain or cyclic alkyl group, and $R^1$ and $R^2$ in combination may form a saturated or unsaturated hydrocarbon ring; $R^4$ and $R^5$ each represent hydrogen, an unsubstituted or substituted straight chain, branched chain or cyclic alkyl group, an unsubstituted or substituted amino group, an unsubstituted or substituted aromatic hydrocarbon group, or an unsubstituted or substituted aromatic heterocyclic group; $R^6$ represents hydrogen, a straight chain, branched chain or cyclic alkyl group, or a trialkylsilyl group; B represents an unsubstituted or substituted alkylene group, an unsubstituted or substituted aromatic hydrocarbon group, an unsubstituted or substituted aromatic heterocyclic group, an unsubstituted or substituted cycloalkylydene group; $R^7$ represents an unsubstituted or substituted straight chain, branched chain or cyclic alkoxyl group, an unsubstituted or substituted amino group, or an unsubstituted or substituted cyclic amino group; $R^3$ represents hydrogen, cyano group, nitro group, —$COR^8$, an unsubstituted or substituted aromatic hydrocarbon group, or an unsubstituted or substituted aromatic heterocyclic group, in which $R^8$ represents an unsubstituted or substituted straight chain, branched chain or cyclic alkoxyl group, an alkenyloxy group, an alkynyloxy group, or —$N(R^{61})$-$B^1$-$COR^{71}$, in which $R^{61}$, $R^{71}$ and $B^1$ are respectively the same as $R^6$, $R^7$, and B.

The second object of the present invention is achieved by optically active 1,4-dihydropyridine derivatives of formula (I-a):

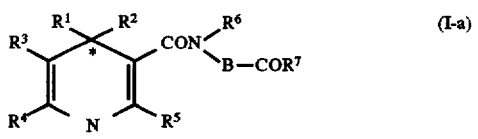

wherein $R^1$, $R^2$, $R^3$, $R^4$, $R^5$, $R^6$, $R^7$, and B are respectively the same as in formula (I), and * indicates a chiral center.

The third object of the present invention with respect to the production of 1,4-dihydropyridine derivatives of formula (I) is achieved by any of the following three processes:

[Process 1]

A ketone compound of formula (II) is allowed to react with an acrylamide compound of formula (III) in the following reaction scheme:

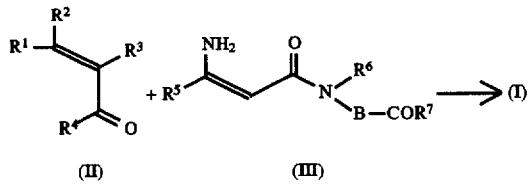

wherein $R^1$, $R^2$, $R^3$, $R^4$, $R^5$, $R^6$, $R^7$, and B are respectively the same as in formula (I).

[Process 2]

An amide compound of formula (IV) is allowed to react with an amino compound of formula (V) in the following reaction scheme:

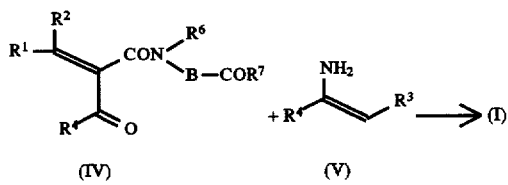

wherein $R^1$, $R^2$, $R^3$, $R^4$, $R^5$, $R^6$, $R^7$, and B are respectively the same as in formula (I).

[Process 3]

A carboxylic acid derivative of formula (VI) is allowed to react with an amine compound of formula (VII) in the following reaction scheme:

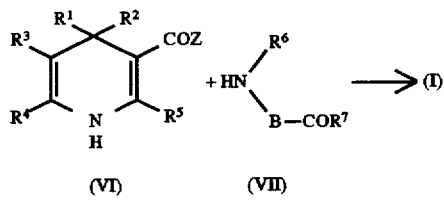

wherein $R^1$, $R^2$, $R^3$, $R^4$, $R^5$, $R^6$, $R^7$, and B are respectively the same as in formula (I), and Z represents a hydroxyl group, a halogen atom, or an active ester residue.

In the third object of the present invention, the optically active 1,4-dihydropyridine derivatives of formula (I-a) are produced by any of the following three processes:

[Process 4]

A keto-ester derivative of formula (X) is allowed to react with an optically active enamine derivative of formula (XI) in the following reaction scheme:

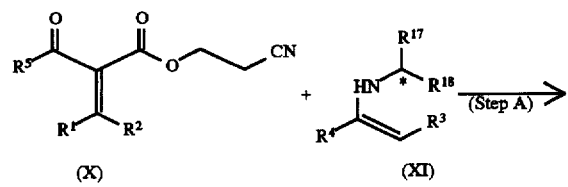

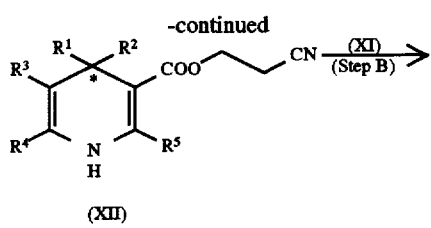

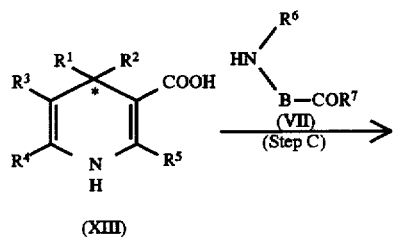

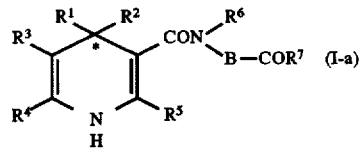

wherein $R^1$, $R^2$, $R^3$, $R^4$, $R^5$, $R^6$, $R^7$, and B are respectively the same as in formula (I), $R^{17}$ and $R^{18}$ are different and independently represent an unsubstituted or substituted straight chain, branched chain or cyclic alkyl group, an unsubstituted or substituted aromatic hydrocarbon group, an unsubstituted or substituted aralkyl group, an unsubstituted or substituted straight chain, branched chain or cyclic alkoxycarbonyl grup, or an unsubstituted or substituted straight chain, branched chain or cyclic aminocarbonyi group, and * indicates a chiral center.

[Process 5]

An N-acylamino acid derivative of formula (XIV) is allowed to react with an optically active enamine derivative of formula (XV) in the following reaction scheme, followed by allowing the product to react with ammonia or an ammonium salt:

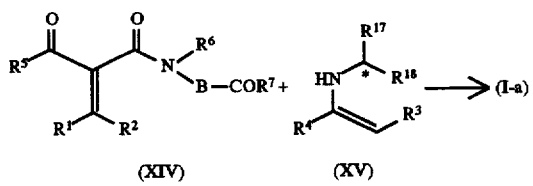

wherein $R^1$, $R^2$, $R^3$, $R^4$, $R^5$, $R^6$, $R^7$, $R^{17}$, $R^{18}$, and B are respectively the same as previously defined, and * indicates a chiral center.

[Process 6]

A ketone derivative of formula (XVI) is allowed to react with an optically active acrylamide derivative of formula (XVII) in the following reaction scheme, followed by allowing the product to react with ammonia or an ammonium salt:

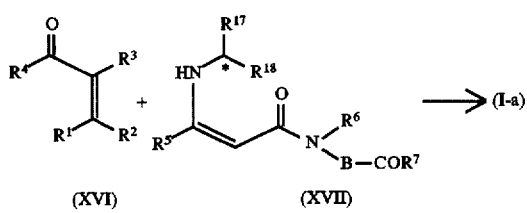

wherein $R^1$, $R^2$, $R^3$, $R^4$, $R^5$, $R^6$, $R^7$, $R^{17}$, $R^{18}$, and B are respectively the same as previously defined, and * indicates a chiral center.

DETAILED DESCRIPTION OF THE PREFERRED EMBODIMENTS

In the 1,4-dihydropyridine derivatives of formula (I) and the optically active 1,4-dihydropyridine derivatives of formula (I-a), $R^1$ represents hydrogen, a straight chain, branched chain or cyclic alkyl group having 1 to 6 carbon atoms, such as methyl group, ethyl group, propyl group, butyl group, pentyl group, hexyl group, 2-propyl group, t-butyl group, cyclopentyl group, and cyclohexyl group; an aromatic hydrocarbon group or an aromatic heterocyclic group such as phenyl group, pyridyl group, quinolyl group, isoquinolyl group, furyl group, thienyl group, benzoxazolyl group, benzthiazolyl group, pyridazinyl group, pyrazinyl group, pyrimidyl group, indolyl group, naphthyl group, benzoxadiazolyl group, and benzthiadiazolyl group, which may have a substituent selected from the group consisting of a halogen atom such as fluorine, chlorine, bromine or iodine; hydroxyl group; cyano group; nitro group; trifluoromethyl group, trichloromethyl group, azide group; amino group; a lower alkyl group having i to 6 carbon atoms, such as methyl group, ethyl group, propyl group, butyl group, pentyl group or hexyl group; a lower alkoxyl group having such as methoxy group, ethoxy group, propoxy group, butoxy group, pentyloxy group, or hexyloxy group; benzoyl group; a lower alkylthio group such as methythio group, ethylthio group, propylthio group, butylthio group, pentylthio group, or hexylthio group; phenylthio group; phenoxy group; a lower alkoxycarbonyl group such as methoxycarbonyl group, ethoxycarbonyl group, propoxycarbonyl group, butoxycarbonyl group, or pentyloxycarbonyl group; a lower acyl group such as acetyl group, propyonyl group, butylyl group, pentanoyl group, or hexanoyl group; benzyloxy group; and cinnamyloxy group.

$R^2$ represents hydrogen, the same straight chain, branched chain or cyclic alkyl group as represented by $R^1$. $R^2$ may be combined with $R^1$ to form a saturated or unsaturated hydrocarbon ring. Examples of such a hydrocarbon ring include cyclopentane ring, cyclohexane ring, and tetrahydronaphthalene ring.

$R^4$ and $R^5$ each represent hydrogen, the same straight chain, branched chain or cyclic alkyl group as represented by $R^1$, a substituted straight chain, branched chain or cyclic alkyl group such as trifluoromethyl group, or trichloromethyl group, an unsubstituted or substituted amino group such as amino group, dimethylamino group, diethylamine group, or dipropylamino group, or the same aromatic hydrocarbon group or aromatic heterocyclic group as represented by $R^1$.

$R^6$ represents hydrogen, the same straight chain, branched chain or cyclic alkyl group as represented by $R^1$, or a trialkylsilyl group.

B represents an unsubstituted or substituted alkylene group, an unsubstituted or substituted aromatic hydrocarbon group, an unsubstituted or substituted aromatic heterocyclic group or an unsubstituted or substituted cycloalkylydene group. Examples of these groups include methylene group, ethylene group, ethylydene group, isopropylydene group, 2-phenylethylydene group, 3-methylbutylydene group, 3-(t-butoxycarbonyl)propylydene group, phenylenediyl group, phenylenediyl group, cyclohexylydene group, and pyrazinediyl group.

$R^7$ represents an unsubstituted or substituted straight chain, branched chain or cyclic alkoxyl group, an unsubstituted or substituted amino group, or an unsubstituted or substituted cyclic amino group.

Examples of the unsubstituted or substituted alkoxyl group as follows: methoxy group, ethoxy group, n-propyloxy group, n-butoxy group, n-pentyloxy group, n-hexyloxy group, n-heptyloxy group, n-octyloxy group, n-nonyloxy group, n-decyloxy group, isopropytoxy group, isobutyloxy group, cyclopentyloxy group, cyclohexyloxy group, aryloxy group, 2-propyn-1-yloxy group, (E)-2-buten-1-yloxy group, (E)-3-buten-1-yloxy group, (E)-2-penten-1-yloxy group, (2E,4E)-2,4-hexadienyloxy group, 2,4-hexadiynyloxy group, (E)-hexa-4-ene-2-yloxy group, (E)-3-phenyl-2-propen-1-yloxy group, (Z)-3-phenyl-2-propen-1-yloxy group, 3-phenyl-2-propyn-1-yloxy group, (2E,4E)-5-phenyl-2,4-pentadien-1-yloxy group, 5-phenyl-penta-2,4-diyn-1-yloxy group, (E)-5-phenylpenta-2-ene-4-yn-1-yloxy group, (E)-3-[4-(1-imidazolylmethyl)phenyl]-2-propen-1-yloxy group, (E)-3-[3-(1-imidazolylmethyl)phenyl]-2-propen-1-yloxy group, (E)-3-[2-(1-imidazolylmethyl)phenyl]-2-propen-1-yloxy group, (E)-3-[4-(1-imidazolyl)phenyl]-2-propen-1-yloxy group, (Z)-3-[4-(1-imidazolylmethyl)phenyl]-2-propen-1-yloxy group, (E)-3-[6-(1-imidazolylmethyl)pyridin-2-yl]-2-propen-1-yloxy group, (E)-3-[5-(1-imidazolylmethyl)furan-2-yl]-2-propen-1-yloxy group, (E)-3-[5-(1-imidazolylmethyl)thiophen-2-yl]-2-propen-1-yloxy group, (E)-3-phenyl-1-methyl-2-propen-1-yloxy group, (E)-1-fluoro-3-phenyl-2-propen-1-yloxy group, 2-methoxyethyloxy group, 3-methoxypropyloxy group, 3-ethoxypropyloxy group, 2-phenoxyethyloxy group, 2-phenylthioethyloxy group, 2-(N-methylamino)ethyloxy group, 2-(N,N-dimethylamino)ethyloxy group, 2-(N-methyl-N-phenylamino)ethyloxy group, 2-(N,N-diethyl)aminoethyloxy group, 2-(N-benzyl-N-methyl)aminoethyloxy group, 2-(1-piperazinyl)ethyloxy group, 4-(1-piperazinyl)butyloxy group, 6-(1-piperazinyl)hexyloxy group, 2-(4-piperidinyl)ethyloxy group, 2-(4-phenylpiperazin-1-yl)ethyloxy group, 3-(4-phenylpiperazin-1-yl)propyloxy group, 4-(4-phenylpiperazin-1-yl)butyloxy group, 6-(4-phenylpiperazin-1-yl)hexyloxy group, 2-(4-phenylpiperidin-1-yl)ethyloxy group, 3-(4-phenylpiperidin-1-yl)propyloxy group, 4-(4-phenylpiperidin-1-yl)butyloxy group, 6-(4-phenylpiperidin-1-yl)hexyloxy group, 2-[4-(diphenylmethyl)piperazin-1-yl]ethyloxy group, 3-[4-(diphenylmethyl)piperazin-1-yl]propyloxy group, 4-[4-(diphenylmethyl)piperazin-1-yl]butyloxy group, 6-[4-(dipheylmethyl)piperazin-1-yl]hexyloxy group, 2-morpholinoethyloxy group, N-benzylpyrrolidin-3-yloxy group, N-benzylpiperidin-3-yloxy group, 2-(1,2,3,4-tetrahydroisoquinolin-2-yl)ethyloxy group, 2,2,2-trifluoroethyloxy group, 2-(3,7-dihydro-3,7-dimethyl-1H-purine-2,6-dion-1-yl)ethyloxy group, and 2-(1,2,3,6-tetrahydro-1,3-dimethyl-2,6-dioxo-7H-purin-7-yl)ethyloxy.

Examples of the unsubstituted or substituted amino group or cyclic amino group are as follows: dimethylamino group, diethylamino group, dipropylamino group, diisopropylamino group, piperidinyl group, piperazinyl group, morpholino group, pyrrolidinyl group, 4-phenylpiperidinyl group, 4-phenylpiperazinyl group, 4-diphenylmethylpiperazinyl group, methoxycarbonylmethylamino group, ethoxycarbonylmethylamino group, isopropyloxycarbonylmethylamino group, t-butoxycarbonylmethylamino group, 1-(t-butoxycarbonyl)-2-methylpropylamino group, 1-(t-butoxycarbonyl)ethylamino group, 1-(t-butoxycarbonyl)-2-phenylethylamino group, 1-(2-methoxyethoxycarbonyl)-2-methylpropylamino group, 1-(ethoxycarbonyl)-1-methylethylamino group, 2-(ethoxycarbonyl)ethylamino group, and N-methyl-N-ethoxycarbonylmethylamino group.

$R^3$ represents hydrogen, cyano group, nitro group, —$COR^8$ the same unsubstituted or substituted aromatic hydrocarbon group, or the same unsubstituted or substituted aromatic heterocyclic group as represented by $R^1$. $R^8$ represents an unsubstituted or substituted straight chain, branched chain or cyclic alkoxyl group, an alkenyloxy group, an alkynyloxy group, or —$N(R^{61})$-$B^1$-$COR^{71}$, in which $R^{61}$, $R^{71}$, and $B^1$ are respectively the same as $R^6$, $R^7$, and B which are defined previously. Examples of the above-mentioned unsubstituted or substituted straight chain, branched chain or cyclic alkoxyl group are those of the alkoxyl group defined by $R^7$.

Specific examples of the 1,4-dihydropyridine derivatives represented by the previously mentioned formula (I) are as follows:

t-butyl 2-[N-[1,4-dihydro-2,6-dimethyl-5-methoxycarbonyl-4-(3-nitrophenyl)pyridine-3-carbonyl]amino]-3-methylbutylate, (+)-t-butyl 2-(S)-[N-[1,4-dihydro-2,6-dimethyl-5-methoxycarbonyl-4-(S)-(3-nitrophenyl)pyridine-3-carbonyl]amino]-3-methylbutylate, (+)-t-butyl 2-(S)-[N-[1,4-dihydro-2,6-dimethyl-5-methoxycarbonyl-4-(R)-(3-nitrophenyl)pyridine-3-carbonyl]amino]-3-methylbutylate, (−)-t-butyl 2-(R)-[N-[1,4-dihydro-2,6-dimethyl-5-methoxycarbonyl-4-(S)-(3-nitrophenyl)pyridine-3-carbonyl]amino]-3-methylbutylate, (−)-t-butyl 2-(R)-[N-[1,4-dihydro-2,6-dimethyl-5-methoxycarbonyl-4-(R)-(3-nitrophenyl)pyridine-3-carbonyl]amino]-3-methylbutylate, t-butyl 2-[N-[1,4-dihydro-2,6-dimethyl-5-methoxycarbonyl-4-(3-nitrophenyl)pyridine-3-carbonyl]amino]acetate, (+)-butyl 2-[N-[1,4-dihydro-2,6-dimethyl-5-methoxycarbonyl-4-(S)-(3-nitrophenyl)pyridine-3-carbonyl]amino]acetate, (−)-t-butyl 2-[N-[1,4-dihydro-2,6-dimethyl-5-methoxycarbonyl-4-(R)-(3-nitrophenyl)pyridine-3-carbonyl]amino]-acetate, t-butyl 2-[N-[1,4-dihydro-2,6-dimethyl-5-methoxycarbonyl-4-(3-nitrophenyl)pyridine-3-carbonyl]amino]propionate, t-butyl 2-[N-[1,4-dihydro-2,6-dimethyl-5-methoxycarbonyl-4-(3-nitrophenyl)pyridine-3-carbonyl]amino]-3-phenylpropionate, t-butyl 1-[1,4-dihydro-2,6-dimethyl-5-methoxycarbonyl-4-(3-nitrophenyl)pyridine-3-yl]carbonyl]pyrrolidine-2-carboxylate, t-butyl 2-[N-[1,4-dihydro-2,6-dimethyl-5-methoxycarbonyl-4-(2-chlorophenyl)pyridine-3-carbonyl]amino]-3-methylbutylate, t-butyl 2-[N-[1,4-dihydro-2,6-dimethyl-5-methoxycarbonyl-4-(2-chlorophenyl)pyridine-3-carbonyl]amino]acetate, t-butyl 2-[N-[1,4-dihydro-2,6-dimethyl-5-methoxycarbonyl-4-(2-chlorophenyl)pyridine-3-carbonyl]amino]propionate, t-butyl 2-[N-[1,4-dihydro-2,6-dimethyl-5-methoxycarbonyl-4-(2-chlorophenyl)pyridine-3-carbonyl]amino]-3-phenylpropionate, t-butyl 1-[1,4-dihydro-2,6-dimethyl-5-methoxycarbonyl-4-(2-chlorophenyl)pyridine-3-carbonyl]amino]pyrrolidine-2-carboxylate, t-butyl 2-[N-[1,4-dihydro-2,6-dimethyl-5-methoxycarbonyl-4-(2-chlorophenyl)pyridine-3-carbonyl]amino]-4-methylpentanoate, t-butyl 2-[N-[1,4-dihydro-2,6-dimethyl-5-methoxycarbonyl-4-(2-chlorophenyl)pyridine-3-carbonyl]amino]-3-(1-t-butoxycarbonyl)butylate, t-butyl 2-[N-[1,4-dihydro-2,6-dimethyl-5-methoxycarbonyl-4-(2-fluorophenyl)pyridine-3-carbonyl]amino]-3-methylbutylate, t-butyl 2-[N-[1,4-dihydro-2,6-dimethyl-5-methoxycarbonyl-4-(2-trifluoromethylphenyl)pyridine-3-carbonyl]amino]-3-methylbutylate, t-butyl 2-[N-[1,4-dihydro-2,6-dimethyl-5-methoxycarbonyl-4-(2-methoxyphenyl)pyridine-3-carbonyl]amino]-3-methylbutylate, t-butyl 2-[N-[1,4-dihydro-2,6-dimethyl-5-methoxycarbonyl-4-(2-methylphenyl)pyridine-3-carbonyl]amino]-3-methylbutylate, t-butyl 2-[N-[1,4-dihydro-2,6-dimethyl-5-methoxycarbonyl-4-(2,4,6-trimethoxyphenyl)pyridine-3-carbonyl]amino]-3-methylbutylate, t-butyl 2-[N-[1,4-dihydro-2,6-dimethyl-5-methoxycarbonyl-4-(3-chlorophenyl)pyridine-3-carbonyl]amino]-3-methylbutylate, t-butyl 2-[N-[1,4-dihydro-2,6-dimethyl-5-methoxycarbonyl-4-(3-fluorophenyl)pyridine-3-carbonyl]amino]-3-methylbutylate, t-butyl 2-[N-[1,4-dihydro-2,6-dimethyl-5-methoxycarbonyl-4-(3-trifluoromethylphenyl)pyridine-3-carbonyl]amino]-3-methylbutylate, t-butyl 2-[N-[1,4-dihydro-2,6-dimethyl-5-methoxycarbonyl-4-(4-nitrophenyl)pyridine-3-carbonyl]amino]-3-methylbutylate, t-butyl 2-[N-[1,4-dihydro-2,6-dimethyl-5-methoxycarbonyl-4-(4-cyanophenyl)pyridine-3-carbonyl]amino]-3-methylbutylate, t-butyl 2-[N-[1,4-dihydro-2,6-dimethyl-5-methoxycarbonyl-4-(3-methoxyphenyl)pyridine-3-carbonyl]amino]-3-methylbutylate, t-butyl 2-[N-[1,4-dihydro-2,6-dimethyl-5-methoxycarbonyl-4-phenylpyridine-3-carbonyl]amino]-3-methylbutylate, t-butyl 2-[N-[1,4-dihydro-2,6-dimethyl-5-methoxycarbonyl-4-(3-hydroxyphenyl)pyridine-3-carbonyl]amino]-3-methylbutylate, t-butyl 2-[N-[1,4-dihydro-2,6-dimethyl-5-methoxycarbonyl-4-cyclohexylpyridine-3-carbonyl]amino]-3-methylbutylate, t-butyl 2-[N-[1,4-dihydro-2,6-dimethyl-5-methoxycarbonyl-4-(2-nitrophenyl)pyridine-3-carbonyl]amino]-3-methylbutylate, t-butyl 2-[N-[1,4-dihydro-2,6-dimethyl-5-methoxycarbonyl-4-(2-nitrophenyl)pyridine-3-carbonyl]amino]acetate, t-butyl 2-[N-[1,4-dihydro-2,6-dimethyl-5-methoxycarbonyl-4-(3-chlorophenyl)pyridine-3-carbonyl]amino]acetate, t-butyl 2-[N-[1,4-dihydro-2,6-dimethyl-5-methoxycarbonyl-4-(2-cyanophenyl)pyridine-3-carbonyl]amino]acetate, t-butyl 2-[N-[1,4-dihydro-2,6-dimethyl-5-methoxycarbonyl-4-(3-cyanophenyl)pyridine-3-carbonyl]amino]acetate, t-butyl 2-[N-[1,4-dihydro-2,6-dimethyl-5-ethoxycarbonyl-4-(3-methylphenyl)pyridine-3-carbonyl]amino]-3-methylbutylate, t-butyl 2-[N-[1,4-dihydro-2,6-dimethyl-5-ethoxycarbonyl-4-(3-nitrophenyl)pyridine-3-carbonyl]amino]acetate, t-butyl 2-[N-[1,4-dihydro-2,6-dimethyl-5-isopropyloxycarbonyl-4-(3-nitrophenyl)pyridine-3-carbonyl]amino]acetate, t-butyl 2-[N-[1,4-dihydro-2,6-dimethyl-5-(2-methoxyethyloxycarbonyl-4-(3-nitrophenyl)pyridine-3-carbonyl]amino]acetate, t-butyl 2-[N-[1,4-dihydro-2,6-dimethyl-5-ethoxycarbonyl-4-(3-nitrophenyl)pyridine-3-carbonyl]amino]-3-methylbutylate, t-butyl 2-[N-[1,4-dihydro-2,6-dimethyl-5-isopropyloxycarbonyl-4-(3-nitrophenyl)pyridine-3-carbonyl]amino]-3-methylbutylate, t-butyl 2-[N-[1,4-dihydro-2,6-dimethyl-5-(2-methoxyethyloxycarbonyl-4-(3-nitrophenyl)pyridine-3-carbonyl]amino]-3-methylbutylate, t-butyl 2-[N-[1,4-dihydro-2,6-dimethyl-5-t-butoxycarbonyl-4-(3-nitrophenyl)pyridine-3-carbonyl]amino]-3-methylbutylate, t-butyl 2-[N-[1,4-dihydro-2,6-dimethyl-5-methoxycarbonyl-4-(3-nitrophenyl)pyridine-3-carbonyl]amino]-3-methylbutylate, 1-[2-[N-[1,4-dihydro-2,6-dimethyl-5-methoxycarbonyl-4-(3-nitrophenyl)pyridine-3-carbonyl]amino]-3-methylbutanoyl]pyrrolidine, 1-[2-[N-[1,4-dihydro-2,6-dimethyl-5-methoxycarbonyl-4-(3-nitrophenyl)pyridine-3-carbonyl]amino]-3-methylbutanoyl]-4-phenylpiperidine, 1-[2-[N-[1,4-dihydro-2,6-dimethyl-5-methoxycarbonyl-4-(3-nitrophenyl)pyridine-3-carbonyl]amino]-3-methylbutanoyl]-4-diphenylmethylpiperidine, 1-[2-[N-[1,4-dihydro-2,6-dimethyl-5-methoxycarbonyl-4-(3-nitrophenyl)pyridine-3-carbonyl]amino]acetyl]pyrrolidine, 1-[2-[N-[1,4-dihydro-2,6-dimethyl-5-methoxycarbonyl-4-(3-nitrophenyl)pyridine-3-carbonyl]amino]acetyl]-4-phenylpiperazine, 1-[2-[N-[1,4-dihydro-2,6-dimethyl-5-methoxycarbonyl-4-(3-nitrophenyl)pyridine-3-carbonyl]amino]acetyl]-4-diphenylmethylpiperazine, 1-[2-[N-[1,4-dihydro-2,6-dimethyl-5-methoxycarbonyl-4-(3-nitrophenyl)pyridine-3-carbonyl]amino]-3-methylbutanoyl]-4-(2-pyridyl)piperazine, 1-[2-[N-[1,4-dihydro-2,6-dimethyl-5-methoxycarbonyl-4-(3-nitrophenyl)pyridine-3-carbonyl]amino]-3-methylbutanoyl]-4-(2-pyrimidyl)piperazine, t-butyl 2-[N-[5-[N-(t-butoxycarbonyl)methylcarbamoyl]-1,4-dihydro-2,6-dimethyl-4-(3-nitrophenyl)pyridine-3-carbonyl]-amino]-3-methylbutylate, ethyl 2-[N-[1,4-dihydro-2,6-dimethyl-5-methoxycarbonyl-4-(3-nitrophenyl)pyridine-3-carbonyl]amino]-3-methylbutylate, ethyl 2-[N-[1,4-dihydro-2,6-dimethyl-5-methoxycarbonyl-4-(3-nitrophenyl)pyridine-3-carbonyl]amino]acetate, isopropyl 2-[N-[1,4-dihydro-2,6-dimethyl-5-methoxycarbonyl-4-(3-nitrophenyl)pyridine-3-carbonyl]amino]acetate, ethyl 2-[N-[1,4-dihydro-2,6-dimethyl-5-methoxycarbonyl-4-(3-nitrophenyl)pyridine-3-carbonyl]amino]propionate, ethyl 2-[N-[1,4-dihydro-2,6-dimethyl-5-methoxycarbonyl-4-(3-nitrophenyl)pyridine-3-carbonyl-N-methylamino]acetate, ethyl 1-[N-[1,4-dihydro-2,6-dimethyl-5-methoxycarbonyl-4-(3-nitrophenyl)pyridine-3-carbonyl]amino]cyclohexanecarboxylate, ethyl 2-[N-[1,4-dihydro-2,6-dimethyl-5-methoxycarbonyl-4-(3-nitrophenyl)pyridine-3-carbonyl]amino]benzoate, ethyl 2-[N-[1,4-dihydro-2,6-dimethyl-5-methoxycarbonyl-4-(3-nitrophenyl)pyridine-3-carbonyl]amino]isobutyrate, ethyl 3-[N-[1,4-dihydro-2,6-dimethyl-5-methoxycarbonyl-4-(3-nitrophenyl)pyridine-3-carbonyl]amino]pyrazine-2-carboxylate, t-butyl 2-[N-[1,4-dihydro-6-methyl-5-methoxycarbonyl-4-(3-nitrophenyl)-2-phenylpyridine-3-carbonyl]amino]-3-methylbutylate, t-butyl 2-[N-[1,4-dihydro-2-methyl-5-methoxycarbonyl-4-(3-nitrophenyl)-6-phenylpyridine-3-carbonyl]amino]acetate, 2-methoxyethyl 2-[N-[1,4-dihydro-2,6-dimethyl-5-methoxycarbonyl-4-(3-nitrophenyl)pyridine-3-carbonyl]amino]-3-methylbutylate, t-butyl 2-[N-[1,4-dihydro-2,6-dimethyl-5-methoxycarbonyl-4-(2-methylphenyl)pyridine-3-carbonyl]amino]acetate, t-butyl 2-[N-[1,4-dihydro-2,6-dimethyl-5-methoxycarbonyl-4-(3-nitrophenyl)pyridine-3-carbonyl]amino]-4-methylpentanoate, t-butyl 2-[N-[1,4-dihydro-2,6-dimethyl-5-methoxycarbonyl-4-(3-nitrophenyl)pyridine-3-carbonyl]amino]-2-cyclopropanecarboxylate, t-butyl 2-[N-[1,4-dihydro-2,6-dimethyl-5-methoxycarbonyl-4-(3-nitrophenyl)pyridine-3-carbonyl]amino]-2-cyclopentanecarboxylate, ethyl 2-[N-[1,4-dihydro-2,6-dimethyl-5-methoxycarbonyl-4-(3-nitrophenyl)pyridine-3-carbonyl]amino]nicotinate, ethyl 6-[N-[1,4-dihydro-2,6-dimethyl-5-methoxycarbonyl-4-(3-nitrophenyl)pyridine-3-carbonyl]amino]nicotinate, ethyl 2-[N-[1,4-dihydro-2,6-dimethyl-5-methoxycarbonyl-4-(3-nitrophenyl)pyridine-3-carbonyl]amino]-2-thiopheneacetate, ethyl 3-[N-[1,4-dihydro-2,6-dimethyl-5-methoxycarbonyl-4-(3-nitrophenyl)pyridine-3-carbonyl]amino]-1,2,4-triazole-5-carboxylate, ethyl 2-[N-[1,4-dihydro-2,6-dimethyl-5-methoxycarbonyl-4-(3-nitrophenyl)pyridine-3-carbonyl]amino]-2-phenylacetate, ethyl 2-[N-[1,4-dihydro-2,6-dimethyl-5-methoxycarbonyl-4-(3-nitrophenyl)pyridine-3-carbonyl]amino]butyrate, ethyl 3-[N-[1,4-dihydro-2,6-dimethyl-5-methoxycarbonyl-4-(3-nitrophenyl)pyridine-3-carbonyl]amino]butyrate, ethyl 4-[N-[1,4-dihydro-2,6-dimethyl-5-methoxycarbonyl-4-(3-nitrophenyl)pyridine-3-carbonyl]amino]butyrate, ethyl 2-[N-[1,4-dihydro-2,6-dimethyl-5-methoxycarbonyl-4-(3-nitrophenyl)pyridine-3-carbonyl]amino]hexanoate, ethyl 6-[N-[1,4-dihydro-2,6-dimethyl-5-methoxycarbonyl-4-(3-nitrophenyl)pyridine-3-carbonyl]amino]hexanoate, ethyl 7-[N-[1,4-dihydro-2,6-dimethyl-5-methoxycarbonyl-4-(3-nitrophenyl)pyridine-3-carbonyl]amino]heptanoate, ethyl 3-[N-[1,4-dihydro-2,6-dimethyl-5-methoxycarbonyl-4-(3-nitrophenyl)pyridine-3-carbonyl]amino]-3-phenylpropionate, ethyl 4-[N-[1,4-dihydro-2,6-dimethyl-5-methoxycarbonyl-4-(3-nitrophenyl)pyridine-3-carbonyl]amino]-2-chlorobenzoate, ethyl 2-[N-[1,4-dihydro-2,6-dimethyl-5-methoxycarbonyl-4-(3-nitrophenyl)pyridine-3-carbonyl]amino]-4-chlorobenzoate, ethyl 2-[1-[N-[1,4-dihydro-2,6-dimethyl-5-methoxycarbonyl-4-(3-nitrophenyl)pyridine-3-carbonyl]amino]piperidinecarboxylate, ethyl 2-[1-[N-[1,4-dihydro-2,6-dimethyl-5-methoxycarbonyl-4-(3-nitrophenyl)pyridine-3-carbonyl]amino]pyrrolecarboxylate, t-butyl 2-[N-[1,4-dihydro-2,6-dimethyl-5-methoxycarbonyl-4-(3-nitrophenyl)pyridine-3-carbonyl]amino]-3-hydroxypropionate t-butyl 2-[N-(1,4-dihydro-5-methoxycarbonyl-6-methyl-4-(3-nitrophenyl)-2-phenylpyridine-3-carbonyl)amino]acetate, t-butyl 2-[N-(1,4-dihydro-5-methoxycarbonyl-4,6-dimethyl-2-phenylpyridine-3-carbonyl)amino]acetate, t-butyl 2-[N-(2-ethyl-1,4-dihydro-5-methoxycarbonyl-6-methyl-4-(3-nitrophenyl)pyridine-3-carbonyl)amino]acetate, t-butyl 2-[N-(1,4-dihydro-5-methoxycarbonyl-6-methyl-2-(2-methoxy-4-methylthiophenyl)-4-(3-nitrophenyl)pyridine-3-carbonyl)amino]acetate, t-butyl 2-[N-(5-cyano-1,4-dihydro-2,6-dimethyl-4-(3-nitrophenyl)pyridine-3-carbonyl)amino]acetate, (+)-t-butyl 2-(S)-[N-(1,4-dihydro-2,6-dimethyl-5-methoxycarbonyl-4-(S)-(3-nitrophenyl)pyridine-3-carbonyl)amino]propionate, (−)-t-butyl 2-(S)-[N-(1,4-dihydro-2,6-dimethyl-5-methoxycarbonyl-4-(R)-(3-nitrophenyl)pyridine-3-carbonyl)amino]propionate, (+)-t-butyl 2-(S)-[N-(1,4-dihydro-2,6-dimethyl-5-methoxycarbonyl-4-(S)-(3-nitrophenyl)pyridine-3-carbonyl)amino]-3-phenylpropionate, (−)-t-butyl 2-(S)-[N-(1,4-dihydro-2,6-dimethyl-5-methoxycarbonyl-4-(R)-(3-nitrophenyl)pyridine-3-carbonyl)amino]-3-phenylpropionate, (+)-t-butyl 2-(S)-[N-(1,4-dihydro-2,6-dimethyl-5-methoxycarbonyl-4-(S)-(3-nitrophenyl)pyridine-3-carbonyl)amino]-4-methylpentanoate, (−)-t-butyl 2-(S)-[N-(1,4-dihydro-2,6-dimethyl-5-methoxycarbonyl-4-(R)-(3-nitrophenyl)pyridine-3-carbonyl)amino]-4-methylpentanoate, (+)-t-butyl 2-(S)-[N-(1,4-dihydro-2,6-dimethyl-5-methoxycarbonyl-4-(S)-(3-nitrophenyl)pyridine-3-carbonyl)amino]-4-(t-butoxycarbonyl)butylate, (−)-t-butyl 2-(S)-[N-[1,4-dihydro-2,6-dimethyl-5-methoxycarbonyl-4-(R)-(3-nitrophenyl)pyridine-3-carbonyl]amino]-4-(t-butoxycarbonyl)butylate, (+)-t-butyl 1-[1,4-dihydro-2,6-dimethyl-5-methoxycarbonyl-4-(S)-(3-nitrophenyl)pyridine-3-carbonyl]pyrrolidine-2-(S)-carboxylate, (−)-t-butyl 1-[1,4-dihydro-2,6-dimethyl-5-methoxycarbonyl-4-(R)-(3-nitrophenyl)pyridine-3-carbonyl]pyrrolidine-2-(S)-carboxylate, t-butyl 2-[N-(1,4-dihydro-2,6-dimethyl-5-methoxycarbonyl-4-(3-fluorophenyl)pyridine-3-carbonyl)amino]acetate, t-butyl 2-[N-(1,4-dihydro-2,6-dimethyl-5-methoxycarbonyl-4-phenylpyridine-3-carbonyl)amino]acetate, t-butyl 2-[N-(1,4-dihydro-2,6-dimethyl-5-methoxycarbonyl-4-(2,4,6-trimethoxyphenyl)pyridine-3-carbonyl)amino]acetate, t-butyl 2-[N-(1,4-dihydro-2,6-dimethyl-5-methoxycarbonyl-4-(3-methoxyphenyl)pyridine-3-carbonyl)amino]acetate, t-butyl 2-[N-(1,4-dihydro-2,6-dimethyl-5-methoxycarbonyl-4-(2-trifluoromethylphenyl)pyridine-3-carbonyl)amino]acetate, t-butyl 2-[N-(4-cyclohexyl-1,4-dihydro-2,6-dimethyl-5-methoxycarbonylpyridine-3-carbonyl)amino]acetate, t-butyl 2-[N-(1,4-dihydro-5-methoxycarbonyl-2,4,6-trimethylpyridine-3-carbonyl)amino]acetate, t-butyl 2-[N-(1,4-dihydro-2,6-dimethyl-5-methoxycarbonyl-4-(4-nitrophenyl)pyridine-3-carbonyl)amino]acetate, t-butyl 2-[N-(1,4-dihydro-2,6-dimethyl-4-(3-nitrophenyl)-5-pyridylpyridine-3-carbonyl)amino]acetate, t-butyl 2-(S)-[N-(1,4-dihydro-2,6-dimethyl-5-methoxycarbonyl-4-(4-nitrophenyl)pyridine-3-carbonyl)amino]-3-methylbutylate, t-butyl 2-(S)-[N-(4-(2-cyanophenyl)-1,4-dihydro-2,6-dimethyl-5-methoxycarbonylpyridine-3-carbonyl)amino]-3-methylbutylate, t-butyl 2-(S)-[N-(1,4-dihydro-2,6-dimethyl-5-methoxycarbonyl-4-(2-trifluoromethylphenyl)pyridine-3-carbonyl)amino]-3-methylbutylate, t-butyl 2-(S)-[N-(4-(3-chlorophenyl)-1,4-dihydro-2,6-dimethyl-5-methoxycarbonylpyridine-3-carbonyl)amino]-3-methylbutylate, t-butyl 2-(S)-[N-(1,4-dihydro-2,6-dimethyl-5-methoxycarbonyl-4-(2-methylphenyl)pyridine-3-carbonyl)amino]-3-methylbutylate, t-butyl 2-(S)-[N-(1,4-dihydro-5-methoxycarbonyl-2,4,6-trimethylpyridine-3-carbonyl)amino]-3-methylbutylate, and t-butyl 2-(S)-[N-(1,4-dihydro-2,6-dimethyl-5-methoxycarbonyl-4-phenylpyridine-3-carbonyl)amino]-3-methylbutylate.

The 1,4-dihydropyridine derivatives of the previously mentioned formula (I) can be produced by any of the following three processes:

[Process 1]

A ketone compound of formula (II) is allowed to react with an acrylamide compound of formula (III) in the following reaction scheme:

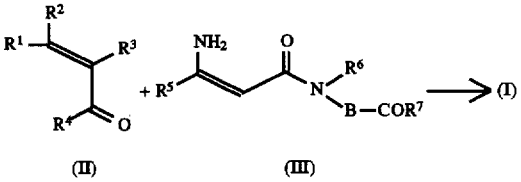

wherein $R^1$, $R^2$, $R^3$, $R^4$, $R^5$, $R^6$, $R^7$, and B are respectively the same as in formula (I).

The above reaction can be carried out by mixing the ketone compound of formula (II) and the acrylamide compound of formula (III) in an inert solvent or without any solvent at 0° C. to 150° C., preferably at 80° C. to 120° C.

Examples of the inert solvent for use in the above reaction include aromatic hydrocarbons such as benzene, toluene and xylene; halogenated hydrocarbons such as dichloromethane, 1,2-dichloroethane, and chloroform; alcohols such as methanol, and ethanol; ethers such as diethyl ether, tetrahydrofuran, and dioxane; dimethylformamide; and diemthyl sulfoxide.

It is also preferable that the above reaction be carried out in an atmosphere of an inert gas such as nitrogen gas or argon gas, and in the dark.

Furthermore, in order to carry out the above reaction efficiently, it is preferable that an equivalent amount of the ketone compound of formula (II) be employed with respect to the acrylamide compound of formula (III).

[Process 2]

An amide compound of formula (IV) is allowed to react with an amino compound of formula (V) in the following reaction scheme under the same conditions as in Process 1:

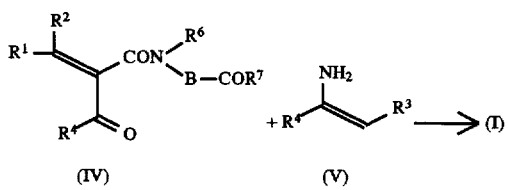

(IV)   (V)

wherein $R^1$, $R^2$, $R^3$, $R^4$, $R^5$, $R^6$, $R^7$, and B are respectively the same as in formula (I).

[Process 3]

A carboxylic acid derivative of formula (VI) is allowed to react with an amine compound of formula (VII) in the following reaction scheme:

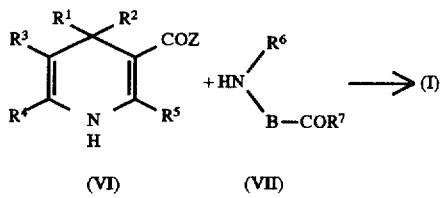

(VI)   (VII)

wherein $R^1$, $R^2$, $R^3$, $R^4$, $R^5$, $R^6$, $R^7$, and B are respectively the same as in formula (I), and Z represents a hydroxyl group, a halogen atom, or an active ester residue.

In the carboxylic acid derivative of formula (VI), when Z is a hydroxyl group, the reaction can be carried out in the presence of a condensation agent. Examples of the condensation agent include carbodiimide agents such as N,N-dicyclohexylcarbodiimide and 1-ethyl-3-(3-diethylaminopropyl)carbodiimide hydrochloride.

The above reaction can be carried in an inert solvent at 0° C. to 150° C., preferably at 20° C. to 120° C.

Examples of the inert solvent for use in the above reaction include halogenated hydrocarbons such as dichloromethane, chloroform, and 1,2-dichloroethane; hydrocarbons such as benzene, toluene and xylene; ethers such as ether, tetrahydrofuran, and dioxane; dimethylformamide; and diemthyl sulfoxide.

It is also preferable that the above reaction be carried out in an atmosphere of an inert gas such as nitrogen gas or argon gas, and in the dark.

In the above reaction, the carbodiimide agents can be employed in an amount of 1 to 1.5 equivalents with respect to the carboxylic acid derivative of formula (VI) and the amine compound of formula (VII).

When Z in formula (VI) is a hydroxyl group, the carboxyl group in the carboxylic acid derivative of formula (VI) is converted to a carboxylic halide group or an active ester residue to produce a carboxylic acid halide or an active ester, and then the compound is allowed to react with the amine compound of formula (VII) in an inert solvent, whereby 1,4-dihydropyridine derivative of formula (I) can be produced. The carboxylic acid halide can be produced by a conventional method by allowing the carboxylic acid derivative of formula (VI) in which Z is a hydroxyl group to react with a phosphorous halide such as phosphorous pentachloride, or phosphorous oxychloride; a thionyl halogenide such as thionyl chloride, or thionyl bromide.

The active ester can be produced by a condensation reaction between the carboxylic acid of formula (VI) and an alcohol such as N-hydroxysuccinimide, N-hydroxyphthalimide, 1-hydroxybenzotriazol, cyanomethyl alcohol, 2,4-dinitrophenol, 4-nitrophenol, and pentachlorophenol. In this reaction, the previously mentioned carbodiimides can be employed in the inert solvent.

Furthermore, in the above-mentioned Process 3 the 1,4-dihydropyridine derivatives of formula (I) can be obtained by converting the compound obtained in any of Process 1, 2 or 3 to the following carboxylic acid derivative of formula (VIII), followed by allowing the carboxylic acid derivative to react with an alcohol compound or an amine compound of formula (IX):

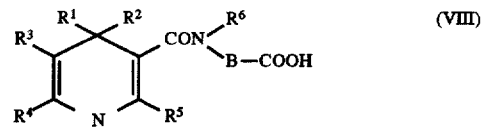

(VIII)

wherein $R^1$, $R^2$, $R^3$, $R^4$, $R^5$, $R^6$, $R^7$, and B are respectively the same as in formula (I).

(IX)

wherein $R^7$ is the same as defined previously.

The above reaction can be carried out under the same conditions by using the same solvents as in Process 3 in which the carboxylic acid derivative of formula (VI) and the amine derivative of formula (VII) are allowed to react.

The optically active 1,4-dihydropyridine derivatives of formula (I-a) are produced by any of the following three processes:

[Process 4]

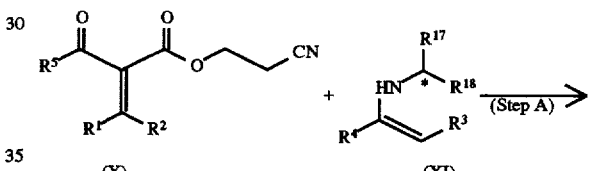

(X)   (XI)

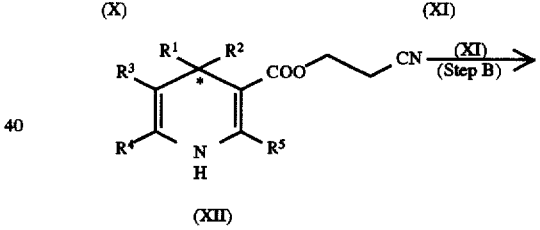

(XII)

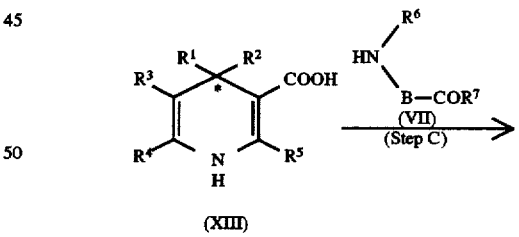

(XIII)

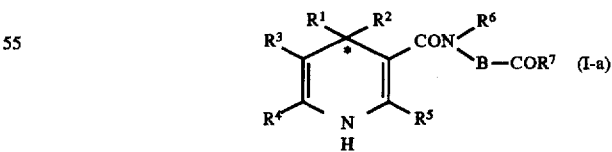

(I-a)

wherein $R^1$, $R^2$, $R^3$, $R^4$, $R^5$, $R^6$, $R^7$, and B are respectively the same as in formula (I), and * indicates a chiral center.

[Step A]

The reaction in Step A in the above reaction scheme can be carried out by mixing the keto-ester derivative of formula (X) and the optically active enamine derivative of formula (XI). The optically active enamine derivative of formula (XI) can be easily obtained by allowing a commercially available keto-ester compound to react with an optically active amine compound.

It is preferable to use a basic compound to carry out the reaction efficiently. Examples of the basic compound are n-butyl lithium, lithium diisopropylamide, sodium hydride, isopropyl magnesium halide, and phenyl magnesium halide. Such a basic compound is generally employed in an amount of 0.5 to 1.5 equivalents to the keto-ester derivative of formula (X).

Furthermore, it is preferable that the above reaction be carried out in a non-protonic solvent. Examples of the non-protonic solvent are ethers such as diethyl ether, and tetrahydrofuran, and aromatic hydrocarbons such as benzene and toluene.

The reaction proceeds at temperatures of −120° to 110° C., but it is preferable that the reaction be carried out in the temperature range of −100° C. to −20° C. to cause the reaction to proceed efficiently.

Furthermore, it is preferable that the reaction be carried out under a water-free condition in an atmosphere of an inert gas such as nitrogen gas or argon gas in order to obtain the desired product in high yield.

The product obtained by the above reaction is easily decomposed at room temperature and therefore difficult to identify. However the product is considered to have the following structure from the identification by use of a mass spectrum:

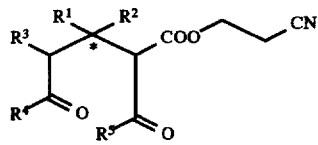

wherein $R^1$, $R^2$, $R^3$, $R^4$, $R^5$, $R^6$, $R^7$, and B are respectively the same as in formula (I), and * indicates a chiral center.

The above reaction product is then allowed to react with ammonia or an ammonium salt, whereby the optically active cyanoethylester of formula (XII) can be obtained.

The ammonia and the ammonium salt employed in the above reaction are commercially available. Examples of the ammonium salt are ammonium acetate, and ammonium chloride.

It is preferable that the ammonia or the ammonium salt be employed in an amount of 1.0 to 20 equivalents, more preferably in an amount of 1.2 to 5 equivalents, to the keto-ester derivative of formula (X) in order to obtain the optically active cyanoethyl ester of formula (XII) in high yield. It is also preferable that the reaction with the ammonia or the ammonium salt be carried out in a solvent. Examples of the solvent are alcohols such as ethanol, methanol and propanol; ethers such as diethyl ether and tetrahydrofuran; and hydrocarbons such as hexane, pentane, toluene and benzene.

The reaction proceeds at temperatures of 0° to 60° C., but it is preferable that the reaction be carried out at room temperature because the operations are simple.

Furthermore, the reaction in the above Step A can be carried out by replacing the keto-ester derivative of formula (X) and the optically active enamine derivative of formula (XI) with a keto-ester derivative of formula (X') and an enamine derivative of formula (XI') resectively, which are shown below:

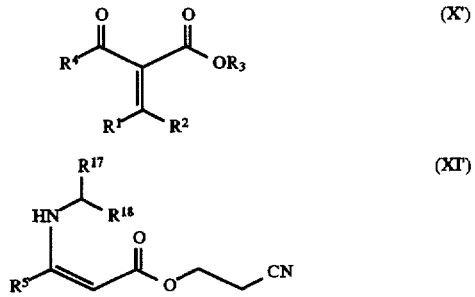

[Step B]

The reaction in Step B can be carried out by mixing the optically active cyanoethyl ester derivative of formula (XII) with a basic compound. Examples of the basic compound employed in this reaction are sodium methylate, sodium hydroxide, and potassium hydroxide. It is preferable that the basic compound be employed in an amount of 1.0 to 3.0 equivalents, more preferably in an amount of 1.0 to 1.2 equivalents, to the optically active cyanoethyl ester derivative of formula (XII), to obtain the product of formula (XIII) in high yield. It is also preferable that the reaction be carried out in a solvent, such as water, an alcohol such as methanol, and ethanol, or a mixed solvent of these solvents, at temperatures of −20° C. to 80° C., more preferably at temperatures of 0° C. to 25° C. to obtain the product of formula (XIII) in high yield.

[Step C]

The reaction in Step C can be carried out by subjecting the optically active carboxylic acid derivative of formula (XIII) obtained in the above Step B and the amine compound of formula (VII) to a condensation reaction. This condensation reaction can be carried out in the same reaction temperature range, using the same carbodiimide agent and reaction solvent as in Process 3.

The carboxyl group in the optically active carboxylic acid derivative of formula (XIII) is converted to a carboxylic halide group or an active ester group as in Process 3, and the thus obtained compound is allowed to react with the amine compound of formula (VII), whereby a 1,4-dihydropyridine derivative of formula (I) can be obtained. This reaction can be carried out in the same reaction temperature range, using the same carbodiimide agent and reaction solvents as in Process 3.

The optically active 1,4-dihydropyridine derivatives of formula (I-a) can be synthesized more efficiently by the following Process 5 and Process 6 than by the abovementioned Process 4:

[Process 5]

An N-acylamino acid derivative of formula (XIV) is allowed to react with an optically active enamine derivative of formula (XV) in the following reaction scheme, followed by allowing the product to react with ammonia or an ammonium salt:

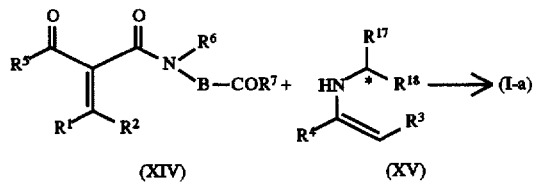

wherein $R^1$, $R^2$, $R^3$, $R^4$, $R^5$, $R^6$, $R^7$, $R^{17}$, $R^{18}$, and B are respectively the same as previously defined, and * indicates a chiral center.

The above reaction can be carried out in the same reaction temperature range, using the same reaction solvents as in Step A in Process 4.

[Process 6]

A ketone derivative of formula (XVI) is allowed to react with an optically active acrylamide derivative of formula (XVII) in the following reaction scheme, followed by allowing the product to react with ammonia or an ammonium salt:

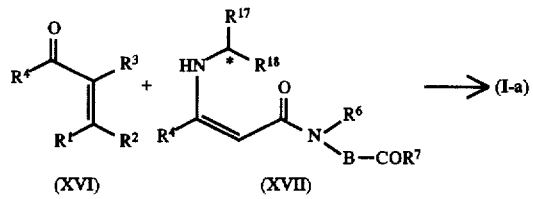

wherein $R^1$, $R^2$, $R^3$, $R^4$, $R^5$, $R^6$, $R^7$, $R^{17}$, $R^{18}$, and B are respectively the same as previously defined, and * indicates a chiral center.

The above reaction can be carried out in the same reaction temperature range, using the same reaction solvents as in Step A in Process 4.

The compounds produced in each of the above processes can be isolated by conventional separation methods, extraction, reprecipitation, recrystallization, and various types of chromatography.

When necessary, the 1,4-dihydropyridine derivatives of formula (I) can be converted to the corresponding acid-addition salts by the reaction with pharmaceutically permissible acids. Examples of such acids are inorganic acids such as hydrochloric acid, hydrobromic acid, phosphoric acid, sulfuric acid, and nitric acid; and organic acids such as acetic acid, propionic acid, lactic acid, and citric acid.

When the 1,4-dihydropyridine derivatives of formula (I) are used as hypotensor, vasodilator, cerebral circulation improvement agent, antithrombotic agent, antiasthmatic, antiinflammatory agent, and antiallergic agent, the derivatives can be administered perorally, intravenously, hypodermically, intramuscularly, or by inhalation. Therefore, the derivatives can be used in various administration forms including pellet, capsule, liquid, and suppository.

EXAMPLE 1

Synthesis of t-butyl 2-(S)-[N-[1,4-dihydro-2,6-dimethyl-5-methoxycarbonyl-4-(3-nitrophenyl)pyridine-3-carbonyl]amino]-3-methylbutylate

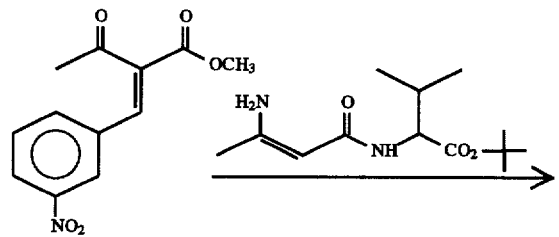

-continued

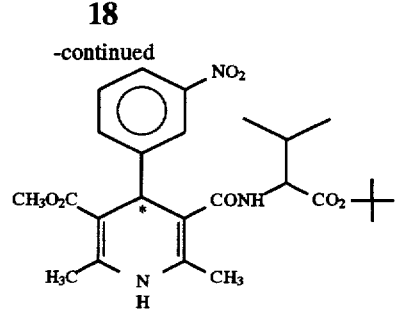

A mixture of 11.2 g (45 mmol) of methyl 2-(3-nitrobenzylidene)acetoacetate and 11.53 g (45 mmol) of (s)-t-butyl 2-(S)-[N-(3-amino-2-butenoyl)amino]-3-methylbutylate was heated at 110° C. for 20 minutes. After cooling to room temperature, the reaction mixture was chromatographed on a silica gel column for purification, whereby 14.7 g (67.5%) of a diastereo mixture was obtained. The diastereo mixture as recrystallized from acetonitrile, so that 8.9 g (40.7%) of Compound a of the captioned compound was obtained. The mother liquor was distilled away under reduced pressure and the residue was recrystallized from methanol, whereby 5.8 g (27%) of Compound b of the captioned compound was obtained.

(Compound a)

Melting point (°C.) 194 (dec.)

IR (vKBr, $cm^{-1}$) 3308, 1716, 1690, 1530, 1354

Mass spectrometry Based on Formula $C_{25}H_{33}N_3O_7$ Calcd. 487.23180 Found 487.23146

NMR (δ, $CDCl_3$) 0.72 (3H, d, J=7 Hz), 0.75 (3H, d, J=7 Hz), 1.40 (9H, s), 1.98–2.01 (1H, m), 2.22 (1H, s), 2.35 (3H, s), 3.62 (3H, s), 4.39 (1H, dd, J=8 Hz, 4 Hz), 4.99 (1H, s), 5.58 (1H, s), 5.76 (1H, d, J=8 Hz), 7.41 (1H, dd, J=8 Hz, 8 Hz), 7.66 (1H, d, J=8 Hz), 8.03 (1H, d, J=8 Hz), 8.13 (1H, s)

Optical rotation $[\alpha]_D^{20}$=+60.9° (C=1.00, ethanol)

(Compound b)

Melting point (°C.) 157 (dec.)

IR (vKBr, $cm^{-1}$) 3330, 1732, 1714, 1676, 1530, 1352

Mass spectrometry Based on Formula $C_{25}H_{33}N_3O_7$ Calcd. 487.23180 Found 487.23299

NMR (δ, $CDCl_3$) 0.698 (3H, d, J=7 Hz), 0.703 (3H, d, J=7 Hz), 1.45 (9H, s), 1.96–2.01 (1H, m), 2.30 (3H, s), 2.33 (3H, s), 3.66 (3H, s), 4.42 (1H, dd, J=8 Hz, 4 Hz), 4.96 (1H, s), 5.59 (1H, s), 5.90 (1H, d, J=8 Hz), 7.42 (1H, dd, J=8 Hz, 8 Hz), 7.70 (1H, d, J=8 Hz), 8.03 (1H, d, J=8 Hz), 8.15 (1H, s)

Optical rotation $[\alpha]_{20}^D$=+31.4° (c=1.00 ethanol)

EXAMPLE 2

Synthesis of t-butyl 2-(R)-[N-[1,4-dihydro-2,6-dimethyl-5-methoxycarbonyl-4-(3-nitrophenyl)pyridine-3-carbonyl]amino-3-methylbutylate

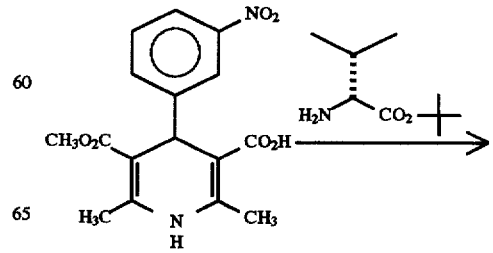

-continued

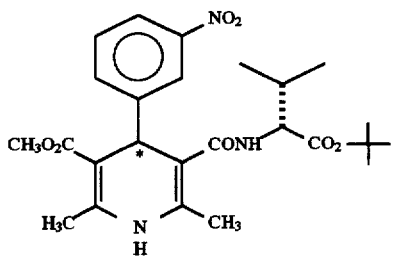

1.65 g (5 mmol) of 1,4-dihydro-2,6-dimethyl-5-methoxycarbonyl-4-(3-nitrophenyl)pyridine-3-carboxylic acid was suspended in 20 ml of dichloromethane. 1.054 g (5.5 mmol) of hydrochloric acid 1-ethyl-3-(3-dimethylaminopropyl)carbodiimide was added to the above suspension in an ice-cooled condition and the mixture was stirred for one hour.

To the above mixture, a solution of dichloromethane containing 0.952 g (5.5 mmol) of D-valine-t-butylester was added and the mixture was stirred at room temperature overnight. After washing with water, the reaction mixture was dried over anhydrous sodium sulfate and the dichloro methane was distilled away under reduced pressure. The reaction mixture was chromatographed on a silica gel column for purification, whereby 1.8 g (74%) of a diastereo mixture was obtained. The thus obtained diastereo mixture was recrystallized from acetonitrile, whereby 0.525 g (21.5%) of Compound a of the captioned compound was obtained. The mother liquor was distilled away under reduced pressure and the residue was recrystallized from methanol, whereby 0.05 g (2%) of Compound b of the captioned compound was obtained.

(Compound a)

Melting point (°C.) 194–196

IR (vKBr, cm$^{-1}$) 3308, 1718, 1688, 1534, 1354

Mass spectrometry Based on Formula $C_{25}H_{33}N_3O_7$ Calcd. 487.23180 Found 487.23174

NMR (δ, CDCl$_3$) 0.72 (3H, d, J=7 Hz), 0.75 (3H, d, J=7 Hz), 1.40 (9H, s), 1.98–2.21 (1H, m), 2.22 (3H, s), 2.35 (3H, s), 3.62 (3H, s), 4.39 (1H, dd, J=9 Hz, 5 Hz), 4.99 (1H, s), 5.54 (1H, s), 5.76 (1H, d, J=9 Hz), 7.41 (1H, dd, J=8 Hz, 8 Hz), 7.66 (1H, d, J=8 Hz), 8.03 (1H, d, J=8 Hz), 8.13 (1H, s)

Optical rotation $[\alpha]_D^{20}$=−32.5° (c=1.00, ethanol)

(Compound b)

Melting point (°C.) 170–173

IR (vKBr, cm$^{-1}$) 3320, 1734, 1712, 1678, 1532, 1352

Mass spectrometry Based on Formula $C_{25}H_{33}N_3O_7$ Calcd. 487.23180 Found 487.23129

NMR (δ, CDCl$_3$) 0.68 (3H, d, J=7 Hz), 0.71 (3H, d, J=7 Hz), 1.45 (9H, s), 1.97–2.10 (1H, m), 2.30 (3H, s), 2.33 (3H, s), 3.66 (3H, s), 4.41 (1H, dd, J=8 Hz, 4 Hz), 4.96 (1H, s), 5.69 (1H, s), 5.91 (1H, d, J=8 Hz), 7.42 (1H, dd, J=8 Hz, 8 Hz), 7.70 (1H, d, J=8 Hz), 8.03 (1H, d, J=8 Hz), 8.15 (1H, s)

Optical rotation $[\alpha]_D^{20}$−60.2° (c=1.00 ethanol)

EXAMPLE 3

Synthesis of t-butyl 2-[N-[1,4-dihydro-2,6-dimethyl-5-methoxycarbonyl-4-(3-nitrophenyl)pyridine-3-carbonyl]amino]acetate The above compound was prepared in accordance with the following reaction scheme by allowing the carboxylic acid employed in Example 2 to react with an amino acid of formula R$^{10}$-H shown below:

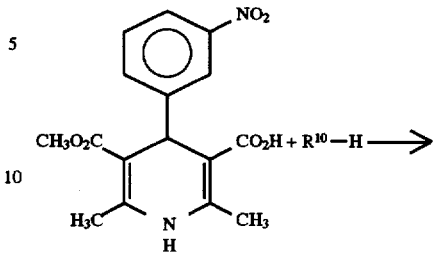

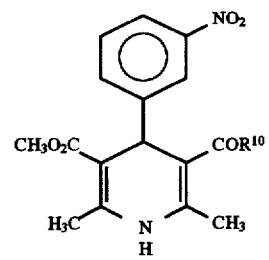

In the above formula, R$^{10}$ is

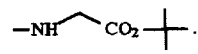

Yield (%) 62.5 (recrystallized from acetonitrile)

Melting point (°C.) 143–146

IR (vKBr, c$^{-1}$) 3364, 1718, 1672, 1534, 1352

Mass spectrometry Based on Formula $C_{22}H_{27}N_3O_7$ Calcd. 445.18484 Found 445.18523

NMR (δ, CDCl$_3$) 1.43 (9H, s), 2.29 (3H, s), 2.33 (3H, s), 3.65 (3H, s), 3.88 (2H, d, J=5 Hz), 4.96 (1H, s), 5.90 (2H, m), 7.42 (1H, dd, J=8 Hz, 8 Hz), 7.68 (1H, d, J=8 Hz), 8.03 (1H, d, J=8 Hz), 8.13 (1H, s)

EXAMPLE 4

Synthesis of t-butyl 2-(S)-[N-[1,4-dihydro-2,6-dimethyl-5-methoxycarbonyl-4-(3-nitrophenyl)pyridine-3-carbonyl]amino]propionate The above compound was prepared in the same reaction scheme as in Example 3 except that the amino acid employed in Example 3 was replaced by an amino acid of formula R$^{10}$-H, in which R$^{10}$ is

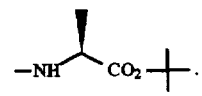

Yield (%) 52.5

Melting point (°C.) oil

Mass spectrometry Based on Formula $C_{23}H_{29}N_3O_7$ Calcd. 459.20051 Found 459.20009

IR (vKBr, cm$^{-1}$) 3356, 1678, 1656, 1532, 1350

NMR (δ, CDCl$_3$) 1.41 (9/2H, s), 1.44 (9/2H, s), 1.26 (3/2H, d, J=7 Hz), 1.28 (3/2H, d, J=7 Hz), 2.25 (3/2H, s), 2.26 (3/2H, s), 2.34 (3/2H, s), 2.35 (3/2H, s), 3.64 (3/2H, s), 3.65 (3/2H, s), 4.40 (1/2H, m), 4.42 (1/2H, m), 4.93 (1/2H, s), 4.97 (1/2H, s), 5.66 (1/2H, s), 4.93 (1/2H, s), 5.98 (1/2H, d, J=8 Hz), 6.02 (1/2H, d, J=8 Hz), 7.41 (1/2H, dd, J=8 Hz,

8 Hz), 7.42 (1/2H, dd, J=8 Hz, 8 Hz), 7.67 (1H, d, J=8 Hz), 8.03 (1H, d, J=8 Hz), 8.13 (1H, s)

EXAMPLE 5

Synthesis of t-butyl 2-(S)-[N-[1,4-dihydro-2,6-dimethyl-5-methoxycarbonyl-4-(3-nitrophenyl)pyridine-3-carbonyl]amino]-3-phenylpropionate (Compound a)

The above compound was prepared in the same reaction scheme as in Example 3 except that the amino acid employed in Example 3 was replaced by an amino acid of formula $R^{10}$-H, in which $R^{10}$ is

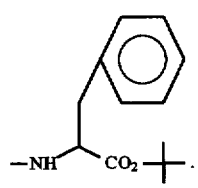

Yield (%) 30.5 (recrystallized from acetonitrile)
Melting point (°C.) 200–203
IR (vKBr, cm$^{-1}$) 3328, 1746, 1700, 1678, 1532, 1348
Mass spectrometry Based of Formula $C_{29}H_{33}N_3O_7$ Calcd. 535.23181 Found 535.23243
NMR (δ, CDCl$_3$) 1.35 (9H, s), 2.19 (3H, s), 2.33 (3H, s), 2.97 (1H, dd, J=15 Hz, 6 Hz), 3.06 (1H, dd, J=15 Hz, 6 Hz), 3.63 (3H, s), 4.68–4.75 (1H, m), 4.89 (1H, s), 5.62 (1H, s), 5.73 (1H, d, J=7 Hz), 6.90–6.98 (2H, m), 7.18–7.26 (3H, m), 7.36 (1H, dd, J=8 Hz, 8 Hz), 7.52 (1H, d, J=8 Hz), 8.02 (1H, d, J=8 Hz), 8.03 (1H, s)

EXAMPLE 6

Synthesis of t-butyl 1-[1,4-dihydro-2,6-dimethyl-5-methoxycarbonyl-4-(3-nitrophenyl)pyridine-3-carbonyl]pyrrolidine-2-(S)-carboxylate The above compound was prepared in the same reaction scheme as in Example 3 except that the amino acid employed in Example 3 was replaced by an amino acid of formula $R^{10}$-H, in which $R^{10}$ is

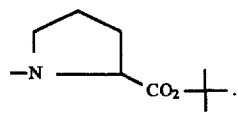

Yield (%) 72.6
Melting point (°C.) oil
IR (vKBr, cm$^{-1}$) 3320, 1742, 1700, 1532, 1350
Mass spectrometry Based on Formula $C_{25}H_{31}N_3O_7$ Calcd. 485.21616 Found 485.21621
NMR (δ, CDCl$_3$) 1.12–2.72 (4H, m), 1.44 (9/2H, s), 1.45 (9/2H, s), 1.96 (3H, s), 2.38 (3/2H, s), 2.40 (3/2H, s), 3.15–3.28 (1/2H, m), 3.41–3.55 (1/2H, m), 3.51 (3/2H, s), 3.60 (3/2H, s), 4.28–4.37 (1H, m), 4.79 (1/2H, s), 5.08 (1/2H, s), 5.57 (1/2H, s), 5.69 (1/2H, s), 7.398 (1/2H, dd, J=8 Hz, 8 Hz), 7.403 (1/2H, dd, J=8 Hz, 8 Hz), 7.56 (1/2H, d, J=8 Hz), 7.64 (1/2H, d, J=8 Hz), 8.02 (1H, d, J=8 Hz), 8.07 (1H, s)

EXAMPLE 7

Synthesis of t-butyl 2-(S)-[N-[1,4-dihydro-2,6-dimethyl-5-methoxycarbonyl-4-(2-chlorophenyl)pyridine-3-carbonyl]amino]carbamoyl]-3-methylbutylate

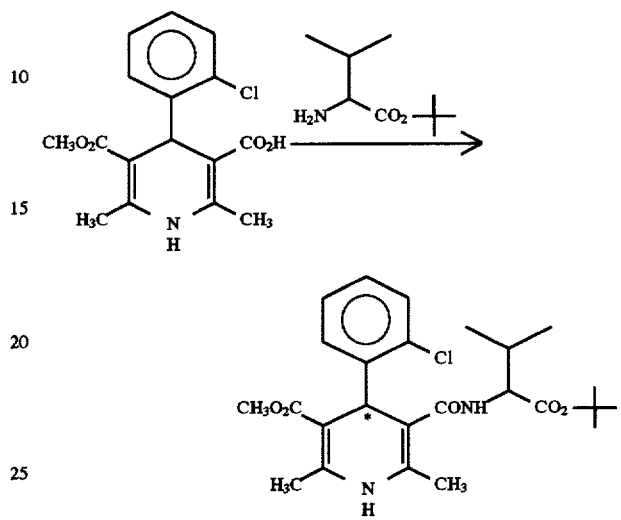

1.60 g (5 mmol) of 1,4-dihydro-2,6-dimethyl-5-methoxycarbonyl-4-(2-chlorophenyl)pyridine-3-carboxylic acid was suspended in 20 ml of dichloromethane. 1.05 g (5.5 mmol) of 1-ethyl-3-(3-dimethylaminopropyl)carbodiimide hydrochloride was added to the the above suspension in an ice-cooled condition and the mixture was stirred for one hour. A dichloromethane solution containing 0.952 g (5.5 mmol) of L-valine-t-butylester hydrochloride and 0.556 g (5.5 mmol) of triethylamine was added to the above mixture. The reaction mixture was refluxed for 3 days. After washing with water, the reaction mixture was dried over anhydrous sodium sulfate and the dichloromethane was distilled away under reduced pressure. The reaction mixture was chromatographed on a silica gel column for purification, whereby 0.93 g (39%) of a diastereo mixture was obtained. The thus obtained diastereo mixture was recrystallized from acetonitrile, whereby 0.15 g (6.2%) of Compound a of the captioned compound was obtained.

Melting point (°C.) 198–200
IR (vKBr, cm$^{-1}$) 3324, 1738, 1708
Mass spectrometry Based on Formula $C_{25}H_{33}ClN_2O_5$ Calcd. 476.20776 Found 476.20785
NMR (δ, CDCl$_3$) 0.69 (6H, d, J=7 Hz), 1.39 (9H, s), 1.92–2.08 (1H, m), 2.09 (3H, s), 2.32 (3H, s), 3.56 (3H, s), 4.37 (1H, dd, J=9 Hz, 5 Hz), 5.33 (2H, s), 5.70 (1H, d, J=9 Hz), 7.07 (1H, dd, J=8 Hz, 8 Hz), 7.18 (1H, d, J=8 Hz), 7.25 (1H, d, J=8 Hz), 7.39 (1H, s)

EXAMPLE 8

Synthesis of t-butyl 2-[N-[1,4-dihydro-2,6-dimethyl-5-methoxycarbonyl-4-(2-chlorophenyl)pyridine-3-carbonyl]amino]acetate The above compound was prepared in accordance with the following reaction scheme by allowing the carboxylic acid employed in Example 7 to react with an amino acid of formula $R^{11}$-H shown below:

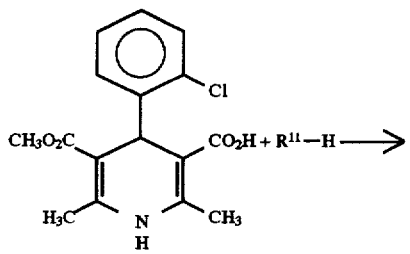

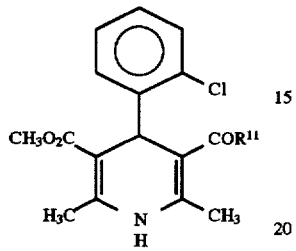

In the above formula, R¹¹ is

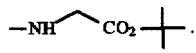

Yield (%) 39.5

Melting point (°C.) 116 (dec.)

IR (vKBr, cm⁻¹) 3352, 1748, 1684

Mass spectrometry Based on Formula $C_{22}H_{27}ClN_2O_5$ Calcd. 434.16080 Found 434.16190

NMR (δ, CDCl$_3$) 1.44 (9H, s), 2.22 (3H, s), 2.34 (3H, s), 3.59 (3H, s), 3.78 (1H, dd, J=18 Hz, 6 Hz), 3.98 (1H, dd, J=18 Hz, 6 Hz), 5.27 (1H, s), 5.65 (1H, s), 6.23 (1H, t, J=6 Hz), 7.08 (1H, dd, J=9 Hz, 8 Hz), 7.18 (1H, dd, J=8 Hz, 8 Hz), 7.24 (1H, d, J=8 Hz), 7.42 (1H, d, J=8 Hz)

EXAMPLE 9

Synthesis of t-butyl 2-(S)-[N-[1,4-dihydro-2,6-dimethyl-5-methoxycarbonyl-4-(2-chlorophenyl)pyridine-3-carbonyl]amino]propionate:

The above compound was prepared in the same reaction scheme as in Example 8 except that the amino acid employed in Example 8 was replaced by an amino acid of formula R¹¹-H, in which R¹¹ is

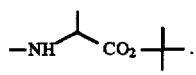

Yield (%) 36

Melting point (°C.) oil

IR (vKBr, cm⁻¹) 3328, 1738, 1696

Mass spectrometry Based on Formula $C_{23}H_{29}ClN_2O_5$ Calcd. 448.17646 Found 448.17655

NMR (δ, CDCl$_3$) 1.23 (3H, d, J=8 Hz), 1.27 (3H, d, J=8 Hz), 1.37 (9/2H, s), 1.46 (9/2H, s), 2.12 (3/2H, s), 2.23 (3/2H, s), 2.32 (3/2H, s), 2.33 (3/2H, s), 3.57 (3/2H, s), 3.59 (3/2H, s), 4.34–4.47 (1H, m), 5.25 (1/2H, s), 5.27 (1/2H, s), 5.61 (1/2H, s), 5.78 (1/2H, s), 5.88 (1/2H, d, J=8 Hz), 6.41 (1/2H, d, J=8 Hz), 7.03–7.12 (1H, m), 7.15–7.28 (2H, m), 7.39–7.46 (1H, m)

EXAMPLE 10

Synthesis of t-butyl 2-(S)-[N-[1,4-dihydro-2,6-dimethyl-5-methoxycarbonyl-4-(2-chlorophenyl)pyridine-3-carbonyl]-amino]-3-phenylpropionate (Compound a)

The above compound was prepared in the same reaction in Example 8 was replaced by an amino acid of formula R¹¹-H, in which R¹¹ is

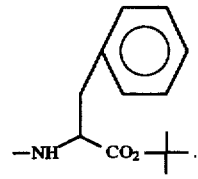

Yield (%) 10.2 (recrystallized from acetonitrile)

Melting point (°C.) 205–210

IR (vKBr, cm⁻¹) 3344, 1732, 1698, 1676

Mass spectrometry Based on Formula $C_{29}H_{33}ClN_2O_5$ Calcd. 524.20776 Found 524.20676

NMR (δ, CDCl$_3$) 1.33 (9H, s), 2.08 (3H, s), 2.33 (3H, s), 2.88 (1H, dd, J=15 Hz, 6 Hz), 3.07 (1H, dd, J=15 Hz, 6 Hz), 3.57 (3H, s), 4.75–4.84 (1H, m), 5.33 (1H, s), 5.38 (1H, s), 5.88 (1H, d, J=9 Hz), 6.83–6.90 (2H, m), 7.08∝7.32 (6H, m), 7.37 (1H, d, J=8 Hz)

EXAMPLE 11

Synthesis of t-butyl 1-[1,4-dihydro-2,6-dimethyl-5-methoxycarbonyl-4-(2-chlorophenyl)pyridine-3-carbonyl]-pyrrolidine-2-(S)-carboxylate The above compound was prepared in the same reaction scheme as in Example 8 except that the amino acid employed in Example 8 was replaced by an amino acid of formula R¹¹-H, in which R¹¹ is

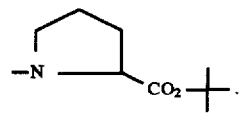

Yield (%) 26

Melting point (°C.) oil

IR (vKBr, cm⁻¹) 3288, 1740, 1700

Mass spectrometry Based on Formula $C_{25}H_{31}ClN_2O_5$ Calcd. 474.19211 Found 474.19190

NMR (δ, CDCl$_3$) 1.13–2.50 (5H, m), 1.42 (9/2H, s), 1.45 (9/2H, s), 1.87 (3/2H, s), 1.94 (3/2H, s), 2.37 (3H, m), 2.97–3.08 (1/2H, m), 3.43–3.82 (1H, m), 3.49 (3/2H, s), 3.53 (3/2H, s), 3.43–3.82 (2H, m), 4.32 (1H, t, J=8 Hz), 5.24 (1/2H, s), 5.33 (1/2H, s), 5.42 (1/2H, s), 5.45 (1/2H, s), 7.02–7.37 (4H, m)

EXAMPLE 12

Synthesis of t-butyl 2-(S)-[N-[1,4-dihydro-2,6-dimethyl-5-methoxycarbonyl-4-(2-chlorophenyl)pyridine-3-carbonyl]amino]-4-methylpentanoate The above compound was prepared in the same reaction scheme as in Example 8 except that the amino acid employed in Example 8 was replaced by an amino acid of formula R¹¹-H, in which R¹¹ is

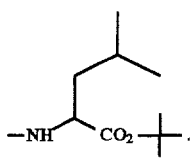

Yield (%) 27

Melting point (°C.) oil

IR (vKBr, cm⁻) 3312, 1736, 1690

Mass spectrometry Based on Formula $C_{26}H_{35}ClN_2O_5$ Calcd. 490.22341 Found 490.22297

NMR (δ, CDCl₃) 0.77 (3/2H, d, J=6 Hz), 0.78 (3/2H, d, J=6 Hz), 0.81 (3/2H, d, J=6 Hz), 0.83 (3/2H, d, J=6 Hz), 1.36 (9/2H, s), 1.46 (1/2H, s), 1.08–1.53 (2H, m), 2.14 (3/2H, s), 2.28 (3/2H, s), 2.32 (3/2H, s), 2.33 (3/2H, s), 3.57 (3/2H, s), 3.60 (3/2H, s), 4.44 (1H, dt, J=9 Hz, 6 Hz), 4.49 (1H, dt, J=9 Hz, 6 Hz), 5.26 (1/2H, s), 5.30 (1/2H, s), 5.48 (1/2H, s), 5.62 (1/2H, d, J=9 Hz), 5.66 (1/2H, s), 6.27 (1/2H, d, J=9 Hz), 7.03–7.12 (1H, m), 7.14–7.29 (2H, m), 7.41 (1/2H, d, J=9 Hz), 7.44 (1/2H, d, J=9 Hz)

EXAMPLE 13

Synthesis of t-butyl 2-(S)-[N-[1,4-dihydro-2,6-dimethyl-5-methoxycarbonyl-4-(2-fluorophenyl)pyridine-3-carbonyl]amino]-3-methylbutylate

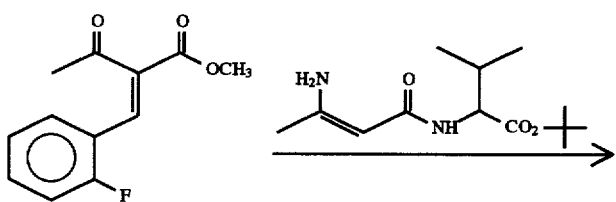

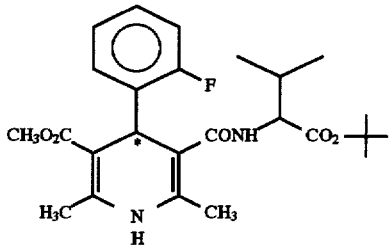

A mixture of 1.11 g (5 mmol) of methyl 2-(2-fluorobenzylidene)acetoacetate and 1.28 g (5 mmol) of (S)-t-butyl 2-[N-(3-amino-2-propenoyl)amino]-3-methylbutylate was refluxed in toluene overnight. After cooling to room temperature, the reaction mixture was chromatographed on a silica gel column for purification, whereby 80 mg (3.5%) of Compound a of the captioned compound, 100 mg (4.3%) of Compound b of the captioned compound and 913 mg (39.8%) of a diastereo mixture were obtained.

(Compound a)

Melting point (°C.) 178 (dec.)

IR (vKBr, cm⁻¹) 3292, 1716, 1698

Mass spectrometry Based on Formula $C_{25}H_{33}FN_2O_5$ Calcd. 460.23731 Found 460.23726

NMR (δ, CDCl₃) 0.74 (3H, d, J=7 Hz), 0.78 (3H, d, J=7 Hz), 1.38 (9H, s), 1.96–2.10 (1H, m), 2.17 (3H, s), 2.32 (3H, s), 3.58 (3H, s), 4.38 (1H, dd, J=9 Hz, 5 Hz), 5.12 (1H, s), 5.42 (1H, s), 5.80 (1H, d, J=9 Hz), 6.95 (1H, ddd, J=10 Hz, 8 Hz, 1 Hz), 7.04 (1H, ddd, J=8 Hz, 8 Hz, 1 Hz), 7.14 (1H, dddd, J=8 Hz, 8 Hz, 5 Hz, 2 Hz), 7.32 (1H, ddd, J=8 Hz, 8 Hz, 2 Hz)

(Compound b)

Melting point (°C.) 113.4–113.7

IR (vKBr, cm⁻¹) 3336, 1734, 1668

Mass spectrometry Based on Formula $C_{25}H_{33}FN_2O_5$ Calcd. 460.23731 Found 460.23845

NMR (δ, CDCl₃) 0.71 (3H, d, J=7 Hz), 0.74 (3H, d, J=7 Hz), 1.48 (9H, s), 1.96–2.08 (1H, m), 2.28 (3H, s), 2.32 (3H, s) 3.60 (3H, s), 4.42 (1H, dd, J=8 Hz, 5 Hz), 5.12 (1H, s), 5.94 (1H, s), 6.22 (1H, d, J=8 Hz), 6.93 (1H, ddd, J=10 Hz, 9 Hz, 2 Hz), 7.05 (1H, ddd, J=8 Hz, 8 Hz, 2 Hz), 7.06–7.17 (1H, m), 7.36 (1H, ddd, J=8 Hz, 8 Hz, 2 Hz)

EXAMPLE 14

Synthesis of t-butyl 2-(S)-[N-[1,4-dihydro-2,6-dimethyl-5-methoxycarbonyl-4-(2-trifluoromethylphenyl)pyridine-3-carbonyl]-amino]-3-methylbutylate (Compound a)

The above compound was prepared in accordance with the same reaction scheme as in Example 13, except that the ketone compound employed in Example 13 was replaced by a ketone compound shown below. Specifically the reaction scheme in this example is as follows:

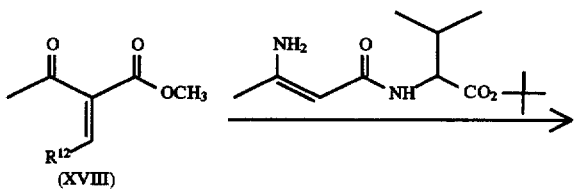

(XVIII)

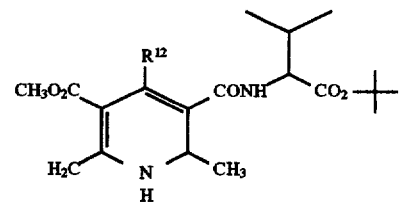

wherein $R^{12}$ is

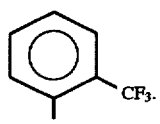

Yield (%) 19.2 (recrystallized from acetonitrile)

Melting point (°C.) 209–212

IR (vKBr, cm$^{-1}$) 3284, 1718, 1704, 1684

Mass spectrometry Based on Formula $C_{26}H_{33}F_3N_2O_5$ Calcd. 510.23411 Found 510.23128

NMR (δ, CDCl$_3$) 0.65 (3H, d, J=7 Hz), 0.67 (3H, d, J=7 Hz), 1.43 (9H, s), 1.88–2.00 (1H, m), 1.96 (3H, s), 2.35 (3H, s), 3.49 (3H, s), 4.29 (1H, dd, J=9 Hz, 5 Hz), 5.25 (1H, s), 5.35 (1H, s), 5.53 (1H, d, J=9 Hz), 7.24 (1H, dd, J=8 Hz, 8 Hz), 7.48 (1H, dd, J=8 Hz, 8 Hz), 7.52 (1H, d, J=8 Hz), 7.59 (1H, d, J=8 Hz)

EXAMPLE 15

Synthesis of t-butyl 2-(S)-[N-[1,4-dihydro-2,6-dimethyl-5-methoxycarbonyl-4-(2-methoxyphenyl) pyridine-3-carbonyl]-amino]-3-methylbutylate The above compound was prepared in the same reaction scheme as in Example 14 except that the ketone compound of formula (XVIII) employed in Example 14 was replaced by a ketone compound of formula (XVIII) in which $R^{12}$ is

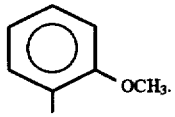

Yield (%) 57.5

Melting point (°C.) oil

IR (vKBr, cm$^{-1}$) 3328, 1734, 1702

Mass spectrometry Based on Formula $C_{26}H_{36}N_2O_6$ Calcd. 471.24947 Found 471.24899

NMR (δ, CDCl$_3$) 0.67 (3/2H, d, J=7 Hz), 0.73 (3/2H, d, J=7 Hz), 0.91 (3H, d, J=7 Hz), 1.33 (9/2H, s), 1.48 (9/2H, s), 1.86–2.00 (1/2H, m), 2.02–2.14 (1/2H, m), 2.30 (3/2H, s), 2.32 (3/2H, s), 2.33 (3/2H, s), 2.37 (3/2H, s), 3.57 (3/2H, s), 3.58 (3/2H, s), 3.88 (3/2H, s), 3.91 (3/2H, s), 4.41 (1H, dd, J=8 Hz, 6 Hz), 5.20 (1/2H, s), 5.25 (1/2H, s), 5.47 (1H, s), 6.67 (1/2H, d, J=8 Hz), 6.78–6.92 (2H, m), 7.07 (1/2H, d, J=8 Hz), 7.09–7.17 (1H, d, J=8 Hz), 7.30–7.36 (1H, m)

EXAMPLE 16

Synthesis of t-butyl 2-(S)-[N-[1,4-dihydro-2,6-dimethyl-5-methoxycarbonyl-4-(3-methylphenyl) pyridine-3-carbonyl]amino]-3-methylbutylate (Compound a)

The above compound was prepared in the same reaction scheme as in Example 14 except that the ketone compound of formula (XVIII) employed in Example 14 was replaced by a ketone compound of formula (XVIII) in which $R^{12}$ is

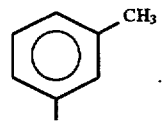

Yield (%) 25.9 (recrystallized from toluene)

Melting point (°C.) 174 (dec.)

IR (vKBr, cm$^{-1}$) 3296, 1718, 1698

Mass spectrometry Based on Formula $C_{26}H_{36}N_2O_5$ Calcd. 456.26238 Found 456.25930

NMR (δ, CDCl$_3$) 0.71 (3H, d, J=7 Hz), 0.81 (3H, d, J=7 Hz), 1.37 (9H, s), 1.97–2.10 (1H, m), 2.21 (3H, s), 2.29 (3H, s), 2.30 (3H, s), 3.63 (3H, s), 4.36 (1H, dd, J=9 Hz, 7 Hz), 4.74 (1H, s), 5.39 (1H, s), 5.71 (1H, d, J=9 Hz), 6.89 (1H, d, J=7 Hz), 7.10–7.15 (3H, m)

EXAMPLE 17

Synthesis of t-butyl 2-[N-[1,4-dihydro-2,6-dimethyl-5-methoxycarbonyl-4-(2,4,6-trimethyoxyphenyl)pyridine-3-carbonyl]amino]-3-methylbutylate The above compound was prepared in the same reaction scheme as in Example 14 except that the ketone compound of formula (XVIII) employed in Example 14 was replaced by a ketone compound of formula (XVIII) in which $R^{12}$ is

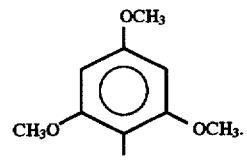

Yield (%) 21.4

Melting point (°C.) oil

IR (vKBr, cm$^{-1}$) 3330, 1734, 1694

Mass spectrometry Based on Formula $C_{28}H_{40}N_2O_8$ Calcd. 532.27842 Found 532.27851

NMR (δ, CDCl$_3$) 0.65 (3/2H, d, J=7 Hz), 0.74 (3/2H, d, J=7 Hz), 0.90 (3/2H, d, J=7 Hz) 0.93 (3/2H, d, J=7 Hz), 1.31 (9/2H, s), 1.48 (9/2H, s), 1.79–1.93 (1/2H, m), 1.97–2.10 (1/2H, m), 2.24 (3H, s), 2.28 (3/2H, s), 2.33 (3/2H, s), 3.52 (3/2H, s), 3.53 (3/2H, s), 3.76 (3H, s), 3.79 (3H, s), 3.80 (3H, s), 4.38 (1/2H, dd, J=10 Hz, 7 Hz), 4.42 (1/2H, dd, J=10 Hz, 7 Hz), 5.38 (1/2H, s), 5.42 (1/2H, s), 6.07 (1H, s), 6.10 (1H, s), 6.78 (1/2H, d, J=9 Hz), 7.19 (1/2H, d, J=9 Hz)

EXAMPLE 18

Synthesis of t-butyl 2-(S)-[N-[1,4-dihydro-2,6-dimethyl-5-methoxycarbonyl-4-(3-chlorophenyl) pyridine-3-carbonyl]amino]-3-methylbutylate (Compound a)

The above compound was prepared in the same reaction scheme as in Example 14 except that the ketone compound of formula (XVIII) employed in Example 14 was replaced by a ketone compound of formula (XVIII) in which $R^{12}$ is

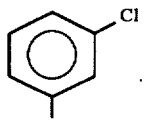

Yield (%) 28.3 (recrystallized from diethyl ether)

Melting point (°C.) 175 (dec.)

IR (vKBr, cm$^{-1}$) 3320, 1716, 1702, 1684

Mass spectrometry Based on Formula $C_{25}H_{33}ClN_2O_5$
Calcd. 476.20776 Found 476.20620

NMR (δ, CDCl$_3$) 0.73 (3H, d, J=7 Hz), 0.79 (3H, d, J=7 Hz), 1.40 (9H, s), 1.98–2.12 (1H, m), 2.22 (3H, s), 2.32 (3H, s), 3.62 (3H, s), 4.39 (1H, dd, J=9 Hz, 4 Hz), 4.82 (1H, s), 5.42 (1H, s), 5.69 (1H, d, J=9 Hz), 7.12 (3H, m), 7.26 (1H, s)

EXAMPLE 19

Synthesis of t-butyl 2-(S)-[N-[1,4-dihydro-2,6-dimethyl-5-methoxycarbonyl-4-(3-fluorophenyl)pyridine-3-carbonyl]-amino]-3-methylbutylate (Compound a)

The above compound was prepared in the same reaction scheme as in Example 14 except that the ketone compound of formula (XVIII) employed in Example 14 was replaced by a ketone compound of formula (XVIII) in which R$^{12}$ is

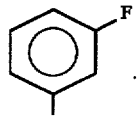

Yield (%) 28.7 (recrystallized from diethyl ether)

Melting point (°C.) 169 (dec.)

IR (vKBr, cm$^{-1}$) 3296, 1716, 1702

Mass spectrometry Based on Formula $C_{25}H_{33}FN_2O_5$
Calcd. 460.23731 Found 460.23785

NMR (δ, CDCl$_3$) 0.73 (3H, d, J=7 Hz), 0.79 (3H, d, J=7 Hz), 1.39 (9H, s), 1.99–2.10 (1H, m), 2.21 (3H, s), 2.31 (3H, s), 3.63 (3H, s), 4.38 (1H, dd, J=9 Hz, 5 Hz), 4.38 (1H, s), 5.44 (1H, s), 5.69 (1H, d, J=9 Hz), 6.86 (1H, dddd, J=8 Hz, 8 Hz, 2 Hz, 1 Hz), 7.01 (1H, ddd, J=10 Hz, 2 Hz, 1 Hz), 7.10 (1H, ddd, J=8 Hz, 2 Hz, 2 Hz), 7.22 (1H, ddd, J=8 Hz, 8 Hz, 6 Hz)

EXAMPLE 20

Synthesis of t-butyl 2-(S)-[N-[1,4-dihydro-2,6-dimethyl-5-methoxycarbonyl-4-(3-trifluoromethylphenyl)-pyridine-3-carbonyl]-amino]-3-methylbutylate (Compound a)

The above compound was prepared in the same reaction scheme as in Example 14 except that the ketone compound of formula (XVIII) employed in Example 14 was replaced by a ketone compound of formula (XVIII) in which R$^{12}$ is

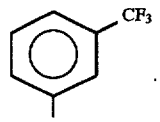

Yield (%) 5.1 (recrystallized from acetonitrile)

Melting point (°C.) 187 (dec.)

IR (vKBr, cm$^{-1}$) 3300, 1720, 1706, 1688

Mass spectrometry Based on Formula $C_{26}H_{33}F_3N_2O_5$
Calcd. 510.23410 Found 510.23190

NMR (δ, CDCl$_3$) 0.69 (3H, d, J=7 Hz), 0.73 (3H, d, J=7 Hz), 1.39 (9H, s), 2.21 (1H, s), 2.33 (3H, s), 3.61 (3H, s), 4.38 (1H, dd, J=9 Hz, 4 Hz), 4.92 (1H, s), 5.44 (1H, s), 5.65 (1H, d, J=9 Hz), 7.37 (1H, dd, J=7 Hz, 7 Hz), 7.43 (1H, d, J=7 Hz), 7.52 (1H, d, J=7 Hz), 7.54 (1H, s)

EXAMPLE 21

Synthesis of t-butyl 2-(S)-[N-[1,4-dihydro-2,6-dimethyl-5-methoxycarbonyl-4-(4-nitrophenyl)pyridine-3-carbonyl]-amino]-3-methylbutylate (Compound a)

The above compound was prepared in the same reaction scheme as in Example 14 except that the ketone compound of formula (XVIII) employed in Example 14 was replaced by a ketone compound of formula (XVIII) in which R$^{12}$ is

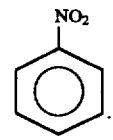

Yield (%) 43 (recrystallized from toluene)

Melting point (°C.) 203 (dec.)

IR (vKBr, cm$^{-1}$) 3300, 1716, 1686, 1520, 1348

Mass spectrometry Based on Formula $C_{25}H_{33}N_3O_7$
Calcd. 487.23181 Found 487.23109

NMR (δ, CDCl$_3$) 0.74 (3H, d, J=7 Hz), 0.76 (3H, d, J=7 Hz), 1.41 (9H, s), 1.99–2.11 (1H, m), 2.21 (3H, s), 2.35 (3H, s), 3.61 (3H, s), 4.40 (1H, dd, J=9 Hz, 4 Hz), 4.99 (1H, s), 5.48 (1H, s), 5.74 (1H, d, J=9 Hz), 7.48 (2H, d, J=9 Hz), 8.12 (2H, d, J=9 Hz)

EXAMPLE 22

Synthesis of t-butyl 2-(S)-[N-[1,4-dihydro-2,6-dimethyl-5-methoxycarbonyl-4-(3-cyanophenyl)pyridine-3-carbonyl]-amino]-3-methylbutylate (Compound a)

The above compound was prepared in the same reaction scheme as in Example 14 except that the ketone compound of formula (XVIII) employed in Exhale 14 was replaced by a ketone compound of formula (XVIII) in which R$^{12}$ is

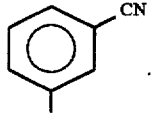

Yield (%) 3.6 (recrystallized from toluene)

Melting point (°C.) 195 (dec.)

IR (vKBr, cm$^{-1}$) 3324, 2236, 1730, 1700

Mass spectrometry Based on Formula $C_{26}H_{33}N_3O_5$ Calcd. 467.24197 Found 467.23961

NMR (δ, CDCl$_3$) 0.69 (6H, d, J=7 Hz), 1.46 (9H, s), 1.97–2.08 (1H, m), 2.30 (3H, s), 2.32 (3H, s), 3.66 (3H, s), 4.42 (1H, dd, J=8 Hz, 4 Hz), 4.87 (1H, s), 5.56 (1H, s), 5.86 (1H, d, J=8 Hz), 7.36 (1H, dd, J=8 Hz, 8 Hz), 7.46 (1H, d, J=8 Hz), 7.59–7.63 (2H, m)

EXAMPLE 23

Synthesis of t-butyl 2-(S)-[N-[1,4-dihydro-2,6-dimethyl-5-methoxycarbonyl-4-(3-methoxyphenyl)pyridine-3-carbonyl]-amino]-3-methylbutylate The above compound was prepared in the same reaction scheme as in Example 14 except that the ketone compound of formula (XVIII) employed in Example 14 was replaced by a ketone compound of formula (XVIII) in which $R^{12}$ is

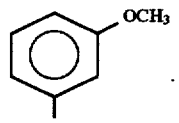

Yield (%) 60.8
Melting point (°C.) oil
IR (vKBr, cm$^{-1}$) 3330, 1732, 1718, 1700, 1682

Mass spectrometry Based on Formula $C_{26}H_{36}N_2O_6$ Calcd. 472.25729 Found 472.25689

NMR (δ, CDCl$_3$) 0.58 (3/2H, d, J=7 Hz), 0.63 (3/2H, d, J=7 Hz), 0.73 (3/2H, d, J=7 Hz), 0.81 (3/2H, d, J=7 Hz), 1.37 (9/2H, s), 1.47 (9/2H, s), 1.90–2.12 (1H, m), 2.21 (3/2H, s), 2.28 (3/2H, s), 2..29 (3/2H, s), 2.31 (3/2H, s), 3.64 (3/2H, s), 3.67 (3/2H, s), 3.77 (3/2H, s), 3.78 (3/2H, s), 4.33–4.42 (1H, m), 4.76 (1/2H, s), 4.78 (1/2H, s), 5.46 (1/2H, s), 5.54 (1/2H, s), 5.73 (1/2H, d, J=8 Hz), 5.94 (1/2H, d, J=8 Hz), 6.72 (1H, d, J=8 Hz), 6.89 (1/2H, s), 6.93 (1/2H, d, J=8 Hz), 6.95 (1/2H, s), 6.98 (1/2H, d, J=8 Hz), 7.20 (1/2H, dd, J=8 Hz, 8 Hz), 7.21 (1/2H, dd, J=8 Hz, 8 Hz)

EXAMPLE 24

Synthesis of t-butyl 2-(S)-[N-[1,4-dihydro-2,6-dimethyl-5-methoxycarbonyl-4-phenylpyridine-3-carbonyl]-amino]-3-methylbutylate (Compound a)

The above compound was prepared in the same reaction scheme as in Example 14 except that the ketone compound of formula (XVIII) employed in Example 14 was replaced by a ketone compound of formula (XVIII) in which $R^{12}$ is

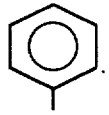

Yield (%) 26.9 (recrystallized from diethyl ether)
Melting point (°C.) 164 (dec.)
IR (vKBr, cm$^{-1}$) 3292, 1718, 1698

Mass spectrometry Based on Formula $C_{25}H_{33}N_2O_5$ Calcd. 441.23891 Found 441.23902

NMR (δ, CDCl$_3$) 0.70 (3H, d, J=7 Hz), 0.79 (3H, d, J=7 Hz), 1.37 (9H, s), 1.95–2.10 (1H, m), 2.22 (3H, s), 2.30 (3H, s), 3.63 (3H, s), 4.36 (1H, dd, J=9 Hz, 5 Hz), 4.79 (1H, s), 5.41 (1H, s), 5.67 (1H, d, J=9 Hz), 7.17 (1H, dd, J=7 Hz, 7 Hz), 7.26 (2H, dd, J=7 Hz, 7 Hz), 7.33 (2H, d, J=7 Hz)

EXAMPLE 25

Synthesis of t-butyl 2-(S)-[N-[1,4-dihydro-2,6-dimethyl-5-methoxycarbonyl-4-(3-hydroxyphenyl)pyridine-3-carbonyl]-amino]-3-methylbutylate (Compound a)

The above compound was prepared in the same reaction scheme as in Example 14 except that the ketone compound of formula (XVIII) employed in Example 14 was replaced by a ketone compound of formula (XVIII) in which $R^{12}$ is

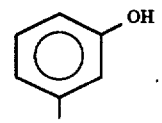

Yield (%) 18.8 (recrystallized from diethyl ether)

Melting point (°C.) 170 (dec.)

IR (vKBr, cm$^-$) 3276, 1718, 1676

Mass spectrometry Based on Formula $C_{25}H_{34}N_2O_6$ Calcd. 458.24163 Found 458.24099

NMR (δ, CDCl$_3$) 0.74 (3H, d, J=7 Hz), 0.82 (3H, d, J=7 Hz), 1.39 (9H, s), 1.97–2.11 (1H, m), 2.17 (3H, s), 2.28 (3H, s), 3.63 (3H, s), 4.37 (1H, dd, J=9 Hz, 5 Hz), 4.75 (1H, s), 5.53 (1H, s), 5.61 (1H, s), 5.79 (1H, d, J=9 Hz), 6.66 (1H, d, J=8 Hz), 6.88 (1H, S), 7.14 (1H, dd, J=8 Hz, 8 Hz)

EXAMPLE 26

Synthesis of t-butyl 2-(S)-[N-[1,4-dihydro-2,6-dimethyl-5-methoxycarbonyl-4-cyclohexylpyridine-3-carbonyl]-amino]-3-methylbutylate (Compound a)

The above compound was prepared in the same reaction scheme as in Example 14 except that the ketone compound of formula (XVIII) employed in Example 14 was replaced by a ketone compound of formula (XVIII) in which $R^{12}$ is

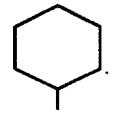

Yield (%) 7.7 (recrystallized from diethyl ether)

Melting point (°C.) 150 (dec.)

IR (vKBr, cm$^{-1}$) 3336, 1718, 1700, 1684

Mass spectrometry Based on Formula $C_{25}H_{40}N_2O_5$ Calcd. 448.29367 Found 448.29334

NMR (δ, CDCl$_3$) 0.94 (3H, d, J=7 Hz), 0.96 (3H, d, J=7 Hz), 0.90–1.71 (11H, m), 1.49 (9H, s), 2.06–2.22 (1H, m), 2.22 (3H, s), 2.31 (3H, s), 3.65 (1H, d, J=5 Hz), 3.71 (3H, s), 4.52 (1H, dd, J=9 Hz, 5 Hz), 5.38 (1H, s), 6.13 (1H, d, J=9 Hz)

EXAMPLE 27

Synthesis of t-butyl 2-(S)-[N-[1,4-dihydro-2,6-dimethyl-5-methoxycarbonyl-4-(2-nitrophenyl)pyridine-3-carbonyl]-amino]-3-methylbutylate (Compound a)

The above compound was prepared in the same reaction scheme as in Example 14 except that the ketone compound of formula (XVIII) employed in Example 14 was replaced by a ketone compound of formula (XVIII) in which $R^{12}$ is

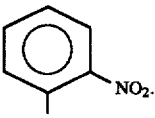

Yield (%) 8.8 (recrystallized from toluene)

Melting point (°C.) 202–204

IR (vKBr, cm$^{-1}$) 3276, 1714, 1686, 1534, 1372

Mass spectrometry Based on Formula $C_{25}H_{33}N_3O_7$ Calcd. 487.23180 Found 487.23055

NMR (δ, CDCl$_3$) 0.89 (3H, d, J=7 Hz), 0.94 (3H, d, J=7 Hz), 1.24 (9H, s), 2.01–2.28 (1H, m), 2.27 (3H, s), 2.44 (3H, s), 3.53 (3H, s), 4.36 (1H, dd, J=8 Hz, 6 Hz), 5.60 (1H, s), 5.62 (1H, s), 7.14 (1H, d, J=8 Hz), 7.28 (1H, dd, J=8 Hz, 8 Hz), 7.49 (1H, dd, J=8 Hz, 8 Hz), 7.59 (1H, d, J=8 Hz), 7.73 (1H, d, J=8 Hz)

EXAMPLE 28

Synthesis of t-butyl 2-(S)-[N-[4-(2-cyanophenyl)-1,4-dihydro-2,6-dimethyl-5-methoxycarbonylpyridine-3-carbonyl]-amino]-3-methylbutylate The above compound was prepared in the same reaction scheme as in Example 14 except that the ketone compound of the formula shown in Example 14 was replaced by the following ketone in which $R^{12}$ in the formula is

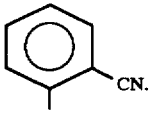

Yield (%) 69.7

Melting point (°C.) oil

IR (vKBr, cm$^{-1}$) 3340, 2228, 1740, 1710

Mass spectrometry Based on Formula $C_{26}H_{33}N_3O_5$ Calcd. 467.24198 Found 467.24205

NMR (δ, CDCl$_3$) 0.59 (3/2H, d, J=8 Hz), 0.64 (3/2H, d, J=8 Hz), 0.788 (3/2H, d, J=8 Hz), 0.794 (3/2H, d, J=8 Hz), 1.41 (9/2H, s), 1.44

(9/2H, s), 1.57–1.73 (1/2H, m), 1.91–2.10 (1/2H, m), 2.13 (3/2H, s), 2.20 (3/2H, s), 2.32 (3/2H, s), 2.33 (3/2H, s), 3.57 (3/2H, s), 3.62 (3/2H, s), 4.36 (1H, dd, J=8 Hz, 5 Hz), 5.18 (1/2H, s), 5.22 (1/2H, s), 5.63 (1/2H, s), 5.67 (1/2H, d, J=8 Hz), 5.71 (1/2H, s), 5.98 (1/2H, d, J=8 Hz), 7.20–7.28 (1H, m), 7.43–7.54 (2H, m), 7.57 (1/2H, d, J=8 Hz), 7.61 (1/2H, d, J=8 Hz)

EXAMPLE 29

Synthesis of t-butyl 2-(S)-[N-[1,4-dihydro-2,6-dimethyl-5-methoxycarbonyl-4-(2-methylphenyl)pyridine-3-carbonyl]amino]-3-methylbutylate The above compound was prepared in the same reaction scheme as in Example 14 except that the ketone compound of the formula shown in Example 14 was replaced by the following ketone in which $R^{12}$ in the formula is

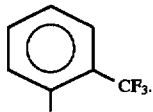

Yield (%) 32.0

Melting point (°C.) oil

IR (vKBr, cm$^{-1}$) 3320, 1735, 1700, 1680

Mass spectrometry Based on Formula $C_{26}H_{36}N_2O_5$ Calcd. 456.26238 Found 456.26229

NMR (δ, CDCl$_3$) 0.55 (3/2H, d, J=7 Hz), 0.59 (3/2H, d, J=7 Hz), 0.64 (3/2H, d, J=7 Hz), 0.72 (3/2H, d, J=7 Hz), 1.41 (9/2H, s), 1.44 (9/2H, s), 1.52–1.64 (1/2H, m), 1.86–1.98 (1/2H, m), 2.03 (3/2H, s), 2.15 (3/2H, s), 2.30 (3/2H, s), 2.32 (3/2H, s), 2.42 (3/2H, s), 2.50 (3/2H, s), 3.53 (3/2H, s), 3.58 (3/2H, s), 4.31 (1/2H, dd, J=9 Hz, 7 Hz), 4.35 (1/2H, dd, J=9 Hz, 7 Hz), 5.03 (1/2H, s), 5.10 (1/2H, s), 5.20 (1/2H, s), 5.37 (1/2H, s), 5.45 (1/2H, d, J=9 Hz), 5.69 (1/2H, d, J=9 Hz), 6.98–7.06 (2H, m), 7.06–7.17 (1H, m), 7.28 (1/2H, d, J=8 Hz), 7.37 (1/2H, d, J=8 Hz)

EXAMPLE 30

Synthesis of t-butyl 2-(S)-[N-[1,4-dihydro-5-methoxycarbonyl-2,4,6-trimethylpyridine-3-carbonyl]amino]-3-methylbutylate The above compound was prepared in the same reaction scheme as in Example 14 except that the ketone compound of formula (XVIII) employed in Example 14 was replaced by a ketone compound of formula (XVIII) in which $R^{12}$ is CH$_3$ Yield (%) 55.1

Melting point (°C.) oil

IR (vKBr, cm$^{-1}$) 3330, 1745, 1680, 1670

Mass spectrometry Based on Formula $C_{20}H_{32}N_2O_5$ Calcd. 380.23108 Found 380.23095

NMR (δ, CDCl$_3$) 0.91–1.00 (6H, m), 1.06 (3/2H, d, J=6 Hz), 1.07 (3/2H, d, J=6 Hz), 1.48 (9H, s), 1.40–1.50 (1/2H, m), 2.15–2.25 (1/2H, m), 2.20 (3/2H, s), 2.21 (3/2H, s), 2.27 (3H, s), 3.65 (1H, q, J=7 Hz), 3.72 (3H, s), 4.57 (1H, dd, J=9 Hz, 5 Hz), 5.44 (1H, s), 6.13 (1/2H, d, J=9 Hz), 6.17 (1/2H, d, J=9 Hz)

EXAMPLE 31

Synthesis of t-butyl 2-[N-[1,4-dihydro-2,6-dimethyl-5-methoxycarbonyl-4-(2-nitrophenyl)pyridine-3-carbonyl]amino]acetate

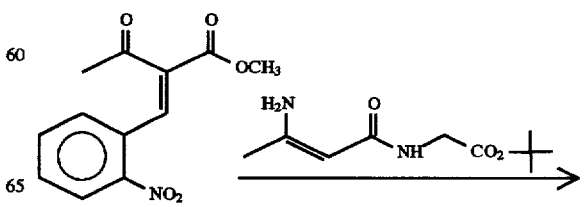

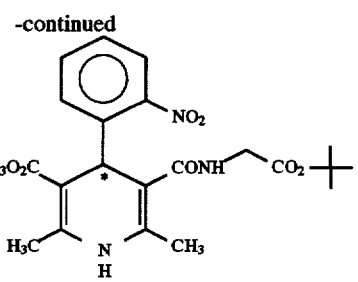

A mixture Of 0.498 g (2 mmol) of methyl 2-(2-nitrobenzylidene)acetoacetate and 0.428 g (2 mmol) of (s)-t-butyl 2-[N-(3-amino-2-butenoyl)amino]acetate was stirred in a light-shielding condition at 120° C. for 15 minutes. After cooling to room temperature, the reaction mixture was chromatographed on a silica gel column for purification, whereby 0.63 g (70.9%) of the captioned compound was obtained as an oily material.

IR (vKBr, cm$^{-1}$) 3330, 1746, 1706, 1668, 1528, 1362

Mass spectrometry Based on Formula $C_{22}H_{27}N_3O_7$ Calcd. 445.18484 Found 445.18513

NMR (δ, CDCl$_3$) 1.40 (9H, s), 2.28 (3H, s), 2.46 (3H, s), 3.52 (3H, s), 3.75 (1H, dd, J=18 Hz, 5 Hz), 3.98 (1H, dd, J=18 Hz, 5 Hz), 5.55 (1H, s), 5.74 (1H, s), 7.29 (1H, dd, J=8 Hz, 8 Hz), 7.46 (1H, t, J=5 Hz), 7.52 (1H, dd, J=8 Hz, 8 Hz), 7.60 (1H, d, J=8 Hz), 7.68 (1H, d, J=8 Hz)

EXAMPLE 32

Synthesis of t-butyl 2-[N-[1,4-dihydro-2,6-dimethyl-5-methoxycarbonyl-4-(3-chlorophenyl) pyridine-3-carbonyl]-amino]acetate The above compound was prepared in accordance with the same reaction scheme as in Example 31 except that the ketone compound employed in Example 31 was replaced by ketone compound shown below. Specifically the reaction scheme in this example is as follows:

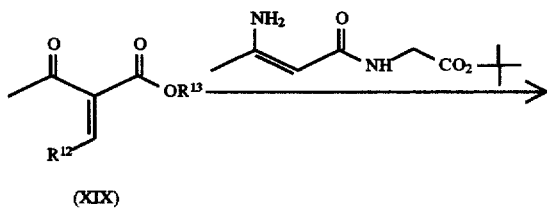

(XIX)

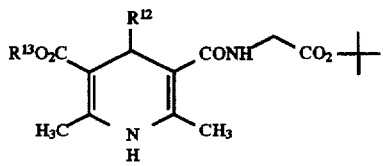

wherein R$^{12}$ is

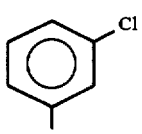

and R$^{13}$ is —CH$_3$.
Yield (%) 89.8
Melting point (°C.) oil

IR (vKBr, cm$^{-1}$) 3268, 1738, 1696, 1664

Mass spectrometry Based on Formula $C_{22}H_{27}ClN_2O_5$ Calcd. 434.16080 Found 434.16166

NMR (δ, CDCl$_3$) 1.44 (9H, s), 2.30 (3H, s), 2.31 (3H, s), 3.66 (3H, s), 3.84 (1H, dd, J=18 Hz, 5Hz), 3.92 (1H, dd, J=18 Hz, 5Hz), 4.80 (1H, s), 5.30 (1H, s), 5.86 (1H, t, J=5 Hz), 7.14–7.29 (4H, m)

EXAMPLE 33

Synthesis of t-butyl 2-[N-[1,4-dihydro-2,6-dimethyl-5-methoxycarbonyl-4-(2-cyanophenyl) pyridine-3-carbonyl]-amino]acetate The above compound was prepared in the same reaction scheme as in Example 32 except that the ketone compound of formula (XIX) employed in Example 32 was replaced by a ketone compound of formula (XIX) in which R$^{12}$ is

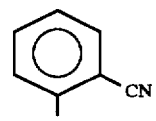

and R$^{13}$ is —CH$_3$.
Yield (%) 89.5
Melting point (°C.) oil
IR (vKBr, cm$^{-1}$) 3288, 2228, 1724, 1688
Mass spectrometry Based on Formula $C_{23}H_{27}N_3O_5$ Calcd. 425.19502 Found 425.19657

NMR (δ, CDCl$_3$) 1.43 (9H, s), 2.20 (3H, s), 2.35 (3H, 3.60 (3H, s), 3.81 (1H, dd, J=18 Hz, 5 Hz), 3.95 (1H, dd, J=18 Hz, 5 Hz), 5.18 (1H, s), 5.58 (1H, s), 6.00 (1H, t, J=5 Hz), 7.21–7.26 (4H, m), 7.47–7.50 (2H, m), 7.56 (1H, d, J=8 Hz)

EXAMPLE 34

Synthesis of t-butyl 2-[N-[1,4-dihydro-2,6-dimethyl-5-methoxycarbonyl-4-(3-cyanophenyl) pyridine-3-carbonyl]-amino]acetate The above compound was prepared in the same reaction scheme as in Example 32 except that the ketone compound of formula (XIX) employed in Example 32 was replaced by a ketone compound of formula (XIX) which R$^{12}$ is

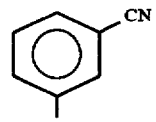

and R$^{13}$ is —CH$_3$.
Yield (%) 91.8
Melting point (°C.) oil
IR (vKBr, cm$^{-1}$) 3352, 2232, 1746, 1682
Mass spectrometry Based on Formula $C_{23}H_{27}N_3O_5$ Calcd. 425.19502 Found 425.19391

NMR (δ, CDCl$_3$) 1.45 (9H, s), 2.29 (3H, s), 2.33 (3H, s), 3.65 (3H, s), 3.88 (2H, d, J=5 Hz), 4.87 (1H, s), 5.59 (1H, s), 5.84 (1H, t, J=5 Hz), 7.36 (1H, dd, J=8 Hz, 8 Hz), 7.46 (1H, d, J=8 Hz), 7.56–7.61 (2H, m)

EXAMPLE 35

Synthesis of t-butyl 2-[N-[1/4-dihydro-2,6-dimethyl-5-methoxycarbonyl-4-(3-methylphenyl) pyridine-3-carbonyl]-amino]acetate The above compound was prepared in the same reaction scheme as in Example 32 except that the ketone compound of formula (XIX) employed in Example 32 was replaced by a ketone compound of formula (XIX) in which $R^{12}$ is

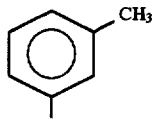

and $R^{13}$ is —$CH_3$.
Yield (%) 60
Melting point (°C.) oil
IR (νKBr, cm$^{-1}$) 3268, 1742, 1694, 1666
Mass spectrometry Based on Formula $C_{23}H_{30}N_2O_5$ Calcd. 414.21543 Found 414.21375
NMR (δ, CDCl$_3$) 1.43 (9H, s), 2.29 (3H, s), 2.31 (3H, s), 3.65 (3H, s), 3.78 (1H, dd, J=18 Hz, 5 Hz), 3.91 (1H, dd, J=18 Hz, 5 Hz), 4.74 (1H, s), 5.47 (1H, s), 5.94 (1H, t, J=8 Hz), 6.97–7.02 (1H, m), 7.12–7.20 (3H, m)

EXAMPLE 36

Synthesis of t-butyl 2-[N-[1,4-dihydro-2,6-dimethyl-5-ethoxycarbonyl-4-(3-nitrophenyl)pyridine-3-carbonyl]-amino]acetate The above compound was prepared in the same reaction scheme as in Example 32 except that the ketone compound of formula (XIX) employed in Example 32 was replaced by a ketone compound of formula (XIX) in which $R^{12}$ is

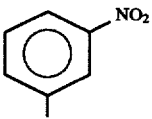

and $R^{13}$ is —$C_2H_5$.
Yield (%) 74.2
Melting point (°C.) oil
IR (νKBr, cm$^{-1}$) 3332, 1746, 1678, 1532, 1350
Mass spectrometry Based on Formula $C_{23}H_{29}N_3O_7$ Calcd. 459.20049 Found 459.19889
NMR (δ, CDCl$_3$) 1.23 (3H, t, J=7 Hz), 1.43 (9H, s), 2.29 (3H, s), 2.33 (3H, s), 3.87 (2H, d, J=5 Hz), 4.04–4.16 (2H, m), 4.96 (1H, s), 5.70 (1H, s), 5.85 (1H, t, J=5 Hz), 7.44 (1H, dd, J=8 Hz, 8 Hz), 7.69 (1H, d, J=8 Hz), 8.03 (1H, d, J=8 Hz), 8.15 (1H, s)

EXAMPLE 37

Synthesis of t-butyl 2-[N-[1,4-dihydro-2,6-dimethyl-5-isopropyloxycarbonyl-4-(3-nitrophenyl)pyridine-3-carbonyl]amino]acetate The above compound was prepared in the same reaction scheme as in Example 32 except that the ketone compound of formula (XIX) employed in Example 32 was replaced by a ketone compound of formula (XIX) in which $R^{12}$ is

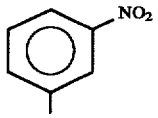

and $R^{13}$ is

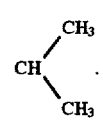

Yield (%) 84.9
Melting point (°C.) oil
IR (νKBr, cm$^{-1}$) 3332, 1746, 1676, 1532, 1350
Mass spectrometry Based on Formula $C_{24}H_{31}N_3O_7$ Calcd. 473.21614 Found 473.21773
NMR (δ, CDCl$_3$) 1.12 (3H, d, J=6 Hz), 1.25 (3H, d, J=6 Hz), 1.43 (9H, s), 2.28 (3H, s), 2.33 (3H, s), 3.87 (2H, d, J=5 Hz), 4.95 (1H, s), 4.92–5.03 (1H, m), 5.66 (1H, s), 5.84 (1H, t, J=5 Hz), 7.42 (1H, dd, J=8 Hz, 8 Hz), 7.68 (1H, d, J=8 Hz), 8.03 (1H, d, J=8 Hz), 8.15 (1H, s)

EXAMPLE 38

Synthesis of t-butyl 2-[N-[1,4-dihydro-2,6-dimethyl-5-(2-methoxyethyloxycarbonyl)-4-(3-nitrophenyl)pyridine-3-carbonyl]amino]acetate The above compound was prepared in the same reaction scheme as in Example 32 except that the ketone compound of formula (XIX) employed in Example 32 was replaced by a ketone compound of formula (XIX) in which $R^{12}$ is

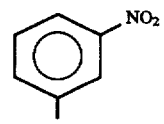

and $R^{13}$ is —(CH$_2$)$_2$—OCH$_3$.
Yield (%) 79.2
Melting point (°C.) oil
IR (νKBr, cm$^{-1}$) 3340, 1742, 1704, 1678, 1528, 1350
Mass spectrometry Based on Formula $C_{24}H_{31}N_3O_8$ Calcd. 489.21106 Found 489.20856
NMR (δ, CDCl$_3$) 1.43 (9H, s), 2.30 (3H, s), 2.34 (3H, s), 3.36 (3H, s), 3.54–3.59 (2H, m), 3.87 (2H, d, J=5 Hz), 4.98 (1H, s), 5.59 (1H, s), 5.88 (1H, t, J=5 Hz), 7.42 (1H, dd, J=8 Hz, 8 Hz), 7.72 (1H, d, J=8 Hz), 8.04 (1H, d, J=8 Hz), 8.15 (1H, s)

EXAMPLE 39

Synthesis of t-butyl 2-[N-[1,4-dihydro-2,6-dimethyl-4-(3-fluorophenyl)-5-methoxycarbonylpyridine-3-carbonyl]-amino]acetate The above compound was prepared in the same reaction scheme as in Example 32 except that the ketone compound of formula (XIX) employed in Example 32 was replaced by a ketone compound of formula (XIX) in which $R^{12}$ is

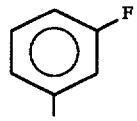

and $R^{13}$ is —$CH_3$.
Yield (%) 62.2 (recrystallized from acetonitrile)
Melting point (°C.) 107–108
IR (νKBr, cm$^{-1}$) 3310, 1750, 1695, 1665
Mass spectrometry Based on Formula $C_{22}H_{27}FN_2O_5$ Calcd. 418.19036 Found 418.19026

NMR (δ, CDCl₃) 1.44 (9H, s), 2.31 (6H, s), 3.66 (3H, s), 3.84 (1H, dd, J=19 Hz, 5 Hz), 3.94 (1H, dd, J=19 Hz, 5 Hz), 4.82 (1H, s), 5.56 (1H, s), 5.87 (1H, t, J=5 Hz), 6.87 (1H, dd, J=10 Hz, 8 Hz), 7.01 (1H, d, J=10 Hz), 7.13 (1H, d, J=8 Hz), 7.22 (1H, ddd, J=8H, 8 Hz, 6 Hz)

EXAMPLE 40

Synthesis of t-butyl 2-[N-[1,4-dihydro-2,6-dimethyl-5-methoxycarbonyl-4-phenylpyridine-3-carbonyl]amino]acetate The above compound was prepared in the same reaction scheme as in Example 32 except that the ketone compound of formula (XIX) employed in Example 32 was replaced by a ketone compound of (XIX) in which R¹² is

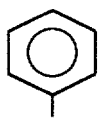

and R¹³ is —CH₃.
Yield (%) 30.0 (recrystallized from acetonitrile)
Melting point (°C.) 87.5–89.2
IR (νKBr, cm⁻¹) 3300, 1740, 1690, 1660
Mass spectrometry Based on Formula $C_{22}H_{28}N_2O_5$
Calcd. 400.19979 Found 400.19990
NMR (δ, CDCl₃) 1.44 (9H, s), 2.30 (3H, s), 2.31 (3H, s), 3.66 (3H, s), 3.79 (1H, dd, J=19 Hz, 5 Hz), 3.91 (1H, dd, J=19 Hz, 5 Hz), 4.79 (1H, s), 5.51 (1H, s), 5.89 (1H, t, J=5 Hz), 7.13–7.38 (5H, m)

EXAMPLE 41

Synthesis of t-butyl 2-[N-[1,4-dihydro-2,6-dimethyl-5-methoxycarbonyl-4-(2,4,6-trimethoxyphenyl)pyridine-3-carbonyl]-amino]acetate The above compound was prepared in the same reaction scheme as in Example 32 except that the ketone compound of formula (XIX) employed in Example 32 was replaced by a ketone compound of formula (XIX) in which R¹² is

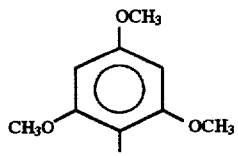

and R¹³ is —CH₃.
Yield (%) 14.3
Melting point (°C.) oil
IR (νKBr, cm⁻¹) 3430, 1740, 1695, 1670
Mass spectrometry Based on Formula $C_{25}H_{34}N_2O_8$
Calcd. 490.23147 Found 490.23140
NMR (δ, CDCl₃) 1.44 (9H, s), 2.25 (3H, s), 2.32 (3H, s), 3.52 (3H, s), 3.60 (1H, dd, J=18 Hz, 5 Hz), 3.77 (3H, s), 3.79 (6H, s), 4.10 (1H, dd, J=18 Hz, 5 Hz), 5.37 (1H, s), 5.50 (1H, s), 6.09 (2H, s), 7.22 (1H, t, J=5 Hz)

EXAMPLE 42

Synthesis of t-butyl 2-[N-[1,4-dihydro-2,6-dimethyl-5-methoxycarbonyl-4-(3-methoxyphenyl)pyridine-3-carbonyl]-amino]acetate The above compound was prepared in the same reaction scheme as in Example 32 except that the ketone compound of formula (XIX) employed in Example 32 was replaced by a ketone compound of formula (XIX) in which R¹² is

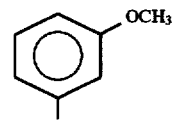

and R¹³ is —CH₃.
Yield (%) 48.8 (recrystallized from acetonitrile)
Melting point (°C.) 157.1–159.6
IR (νKBr, cm⁻¹) 3360, 1745, 1700, 1680
Mass spectrometry Based on Formula $C_{23}H_{30}N_2O_6$
Calcd. 430.21035 Found 430.21041
NMR (δ, CDCl₃) 1.44 (9H, s), 2.29 (3H, s), 2.30 (3H, s), 3.66 (3H, s), 3.79 (3H, s), 3.79 (1H, dd, J=18 Hz, 5 Hz), 3.92 (1H, dd, J=18 Hz, 5 Hz), 4.77 (1H, s), 5.54 (1H, s), 5.94 (1H, t, J=8 Hz), 6.74 (1H, d, J=8 Hz), 6.91 (1H, s), 6.95 (1H, d, J=8 Hz), 7.20 (1H, dd, J=8 Hz, 8 Hz)

EXAMPLE 43

Synthesis of t-butyl 2-[N-[1,4-dihydro-2,6-dimethyl-5-methoxycarbonyl-4-(2-trifluoromethylphenyl)pyridine-3-carbonyl]amino]acetate The above compound was prepared in the same reaction scheme as in Example 32 except that the ketone compound of formula (XIX) employed in Example 32 was replaced by a ketone compound of formula (XIX) in which R¹² is

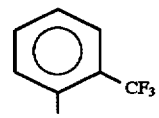

and R¹³ is —CH₃.
Yield (%) 29.9 (recrystallized from acetonitrile)
Melting point (°C.) 169–171.6
IR (νKBr, cm⁻¹) 3330, 1750, 1690, 1645
Mass spectrometry Based on Formula $C_{23}H_{27}F_3N_2O_5$
Calcd. 468.18717 Found 468.18720
NMR (δ, CDCl₃) 1.43 (9H, s), 2.01 (3H, s), 2.37 (3H, s), 3.50 (3H, s), 3.78 (1H, dd, J=18 Hz, 5 Hz), 3.90 (1H, dd, J=18 Hz, 5 Hz), 5.19 (1H, s), 5.38 (1H, s), 5.63 (1H, t, J=5 Hz), 7.26 (1H, dd, J=8 Hz, 8 Hz), 7.48 (1H, dd, J=8 Hz, 8 Hz), 7.51 (1H, d, J=8 Hz), 7.58 (1H, d, J=8 Hz)

EXAMPLE 44

Synthesis of t-butyl 2-[N-[4-cyclohexyl-1,4-dihydro-2,6-dimethyl-5-methoxycarbonylpyridine-3-carbonyl]amino]-acetate The above compound was prepared in the same reaction scheme as in Example 32 except that the ketone compound of formula (XIX) employed in Example 32 was replaced by a ketone compound of formula (XIX) in which R¹² is

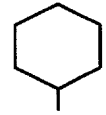

and R¹³ is —CH₃.
Yield (%) 12.3

Melting point (°C.) oil

IR (vKBr, cm$^{-1}$) 3330, 1740, 1680

Mass spectrometry Based on Formula $C_{22}H_{34}N_2O_5$ Calcd. 406.24673 Found 406.24668

NMR (δ, CDCl$_3$) 0.80–1.72 (11H, m), 1.49 (9H, s), 2.25 (3H, s), 2.31 (3H, s), 3.59 (1H, d, J=5 Hz), 3.71 (3H, s), 4.01 (2H, d, J=5 Hz), 5.42 (1H, s), 6.12 (1H, t, J=5 Hz)

EXAMPLE 45

Synthesis of t-butyl 2-[N-[1,4-dihydro-5-methoxycarbonyl-2,4,6-trimethylpyridine-3-carbonyl]amino]acetate The above compound was prepared in the same reaction scheme as in Example 32 except that the ketone compound of formula (XIX) employed in Example 32 was replaced by a ketone compound of formula (XIX) in which R$^{12}$ is

and R$^{13}$ is —CH$_3$.

Yield (%) 32.5

Melting point (°C.) oil

IR (vKBr, cm$^{-1}$) 3320, 1750, 1680

Mass spectrometry Based on Formula $C_{17}H_{26}N_2O_5$ Calcd. 338.18414 Found 338.18385

NMR (δ, CDCl$_3$) 1.05 (3H, d, J=7 Hz), 1.49 (9H, s), 2.24 (3H, s), 2.28 (3H, s), 3.62 (1H, q, J=7 Hz), 3.72 (3H, s), 3.96 (1H, dd, J=18 Hz, 5 Hz), 4.07 (1H, dd, J=18 Hz, 5 Hz), 5.43 (1H, s), 6.14 (1H, t, J=5 Hz)

EXAMPLE 46

Synthesis of t-butyl 2-[N-[1,4-dihydro-2,6-dimethyl-5-methoxycarbonyl-4-(4-nitrophenyl) pyridine-3-carbonyl]-amino]acetate The above compound was prepared in the same reaction scheme as in Example 32 except that the ketone compound of formula (XIX) employed in Example 32 was replaced by a ketone compound of formula (XIX) in which R$^{12}$ is

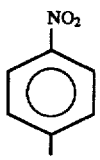

and R$^{13}$ is —CH$_3$.

Yield (%) 49.4 (recrystallized from acetonitrile)

Melting point (°C.) 157.3–159.1

IR (vKBr, cm$^{-1}$) 3300, 1750, 1680, 1670, 1520, 1350

Mass spectrometry Based on Formula $C_{22}H_{27}N_3O_7$ Calcd. 445.18486 Found 445.18469

NMR (δ, CDCl$_3$) 1.45 (9H, s), 2.30 (3H, s), 2.34 (3H, s), 3.65 (3H, s), 3.88 (2H, d, J=5 Hz), 4.96 (1H, s), 5.54 (1H, s), 5.84 (1H, t, J=5 Hz), 7.49 (2H, d, J=9 Hz), 8.12 (2H, d, J=9 Hz)

EXAMPLE 47

Synthesis of t-butyl 2-[N-[1,4-dihydro-2,6-dimethyl-5-methoxycarbonyl-4-(2-methylphenyl) pyridine-3-carbonyl]-amino]acetate:

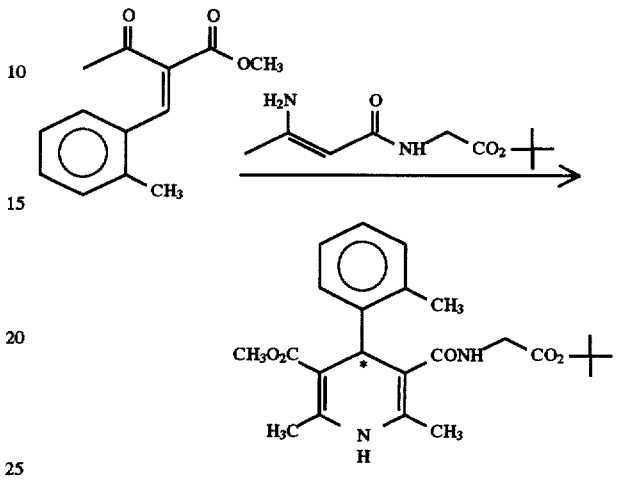

A mixture of 327 mg (1.5 mmol) of methyl 2-(2-methylbenzylidene)acetoacetate and 318 g (1.5 mmol) of t-butyl 2-[N-(3-amino-2-butenoyl)amino]acetate was stirred in a light-shielding condition at 120° C. for 10 minutes. After cooling to room temperature, the reaction mixture was chromatographed on a silica gel column for purification, whereby 308 mg (49.5%) of the captioned compound was obtained as an oily material.

IR (vKBr, cm$^{-1}$) 3332, 1746, 1682

Mass spectrometry Based on Formula $C_{23}H_{30}N_2O_5$ Calcd. 414.21538 Found 414.21498

NMR (δ, CDCl$_3$) 1.43 (9H, s), 2.13 (3H, s), 2.32 (3H, s), 2.46 (3H, s), 3.56 (3H, s), 3.73 (2H, dd, J=18 Hz, 5 Hz), 3.92 (2H, dd, J=18 Hz, 5 Hz), 5.04 (1H, s), 5.34 (1H, s), 5.67 (1H, t, J=5 Hz), 7.02–7.15 (3H, m), 7.33 (1H, d, J=8 Hz)

EXAMPLE 48

Synthesis of t-butyl 2-(S)-[N-[1,4-dihydro-2,6-dimethyl-5-ethoxycarbonyl-4-(3-nitrophenyl) pyridine-3-carbonyl]amino]-3-methylbutylate

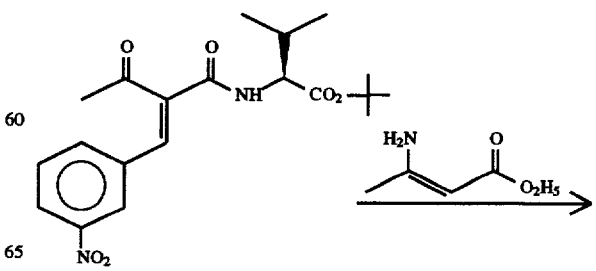

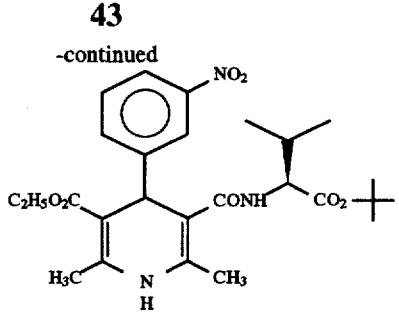

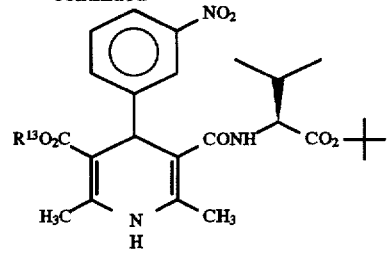

wherein $R^{13}$ is

A mixture of 1.95 g (5 mmol) of t-butyl 2-[N-[2-acetyl-3-(3-nitrophenyl)-2-propenoyl]amino]-3-methylbutylate and 0.645 g (2 mmol) of ethyl 3-aminocrotonate was stirred in a light-shielding condition at 120° C. for 20 minutes. After cooling to room temperature, the reaction mixture was chromatographed on a silica gel column for purification, whereby 1.78 g (71.1%) of the captioned compound was obtained as an oily material.

IR (νKBr, cm$^{-1}$) 3320, 1736, 1682, 1532, 1352

Mass spectrometry Based on Formula $C_{26}H_{35}N_3O_7$
Calcd. 501.24746 Found 501.24759

NMR (δ, CDCl$_3$) 0.68–0.75 (6H, m), 1.19 (3/2H, t, J=7 Hz), 1.24 (3/2H, t, J=7 Hz), 1.40 (9/2H, s), 1.45 (9/2H, s), 1.97–2.08 (1H, m), 2.22 (3/2H, s), 2.29 (3/2H, s), 2.33 (3/2H, s), 2.35 (3/2H, s), 4.02–4.18 (2H, m), 4.13–4.46 (1H, m), 4.97 (1/2H, s), 5.00 (1/2H, s), 5.52 (1/2H, s), 5.61 (1/2H, s), 5.65 (1/2H, d, J=8 Hz), 5.90 (1/2H, d, J=8 Hz), 7.39 (1/2H, dd, J=8 Hz, 8 Hz), 7.42 (1/2H, dd, J=8 Hz, 8 Hz), 7.67 (1/2H, d, J=8 Hz), 7.70 (1/2H, d, J=8 Hz), 8.03 (1/2H, s), 8.15 (1/2H, s)

EXAMPLE 49

Synthesis of t-butyl 2-(S)-[N-[1,4-dihydro-2,6-dimethyl-5-isopropyloxycarbonyl-4-(3-nitrophenyl)pyridine-3-carbonyl]amino-3-methylbutylate The above compound was prepared in accordance with the same reaction scheme as in Example 48, except that the amine compound employed in Example 48 was replaced by an amine compound shown below. Specifically the reaction scheme in this example is as follows:

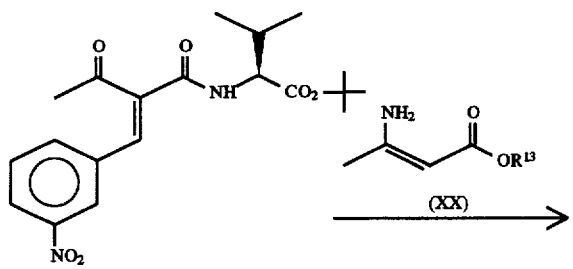

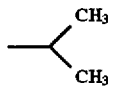

Yield (%) 58.3
Melting point (°C.) oil
IR (νKBr, cm$^{-1}$) 3324, 1732, 1678, 1532, 1352
Mass spectrometry Based on Formula $C_{27}H_{37}N_3O_7$
Calcd. 515.26310 Found 515.26335

NMR (δ, CDCl$_3$) 0.68–0.74 (6H, m), 1.05 (3/2H, d, J=6 Hz), 1.13 (3/2H, d, J=6 Hz), 1.18 (3/2H, d, J=6 Hz), 1.26 (3/2H, d, J=6 Hz), 1.40 (9/2H, s), 1.44 (9/2H, s), 1.96–2.08 (1H, m), 2.20 (3/2H, s), 2.28 (3/2H, s), 2.32 (3/2H, s), 2.34 (3/2H, s), 4.37–4.41 (1H, m), 4.88–5.02 (1H, m), 4.96 (1/2H, s), 4.99 (1/2H, s), 5.59 (1/2H, s), 5.68 (1/2H, s), 5.72 (1/2H, d, J=7 Hz), 5.89 (1/2H, d, J=7 Hz), 7.40 (1/2H, dd, J=8 Hz, 8 Hz), 7.42 (1/2H, dd, J=8 Hz, 8 Hz), 7.68 (1/2H, d, J=8 Hz), 7.71 (1/2H, d, J=8 Hz), 8.03 (1H, d, J=8 Hz), 8.15 (1/2H, s), 8.17 (1/2H, s)

EXAMPLE 50

Synthesis of t-butyl 2-(S)-[N-[1,4-dihydro-2,6-dimethyl-5-(2-methoxyethyloxycarbonyl)-4-(3-nitrophenyl)-pyridine-3-carbonyl]-amino-3-methylbutylate (Compound a)

The above compound was prepared in the same reaction scheme as in Example 49 except that the amine compound of formula (XX) employed in Example 49 was replaced by an amine compound of formula (XX) in which $R^{13}$ is —(CH$_2$)$_2$—OCH$_3$.

Yield (%) 21.4 (recrystallized from diethyl ether)
Melting point (°C.) 172.7–174.4
IR (νKBr, cm$^{-1}$) 3304, 1736, 1682, 1532, 1352
Mass spectrometry Based on Formula $C_{27}H_{37}N_3O_8$
Calcd. 531.25800 Found 531.25891

NMR (δ, CDCl$_3$) 0.69 (3H, d, J=6 Hz), 0.71 (3H, d, J=6 Hz), 1.44 (9H, s), 1.96–2.10 (9H, m), 2.30 (3H, s), 2.34 (3H, s), 3.36 (3H, s), 3.53–3.60 (2H, m), 4.12–4.27 (2H, m), 4.39 (1H, dd, J=8 Hz, 4 Hz), 4.99 (1H, s), 5.61 (1H, s), 5.93 (1H, d, J=8 Hz), 7.42 (1H, dd, J=8 Hz, 8 Hz), 7.75 (1H, d, J=8 Hz), 8.03 (1H, d, J=8 Hz), 8.18 (1H, s)

EXAMPLE 51

Synthesis of t-butyl 2-(S)-[N-[5[N-(1-(S)-t-butoxy-2-methylpropyl)]carbamoyl-1,4-dihydro-2,6-dimethyl-4-(3-nitrophenyl)pyridine]-3-carbonyl]amino]-3-methylbutylate The above compound was prepared in the same reaction scheme as in Example 49 except that the amine compound of formula (XX) employed in Example 49 was replaced by an amine compound of formula (XX) in which R¹³ is

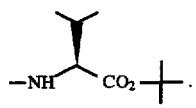

Yield (%) 60.4 (recrystallized from toluene)

Melting point (°C.) 204.2–206.2

IR (νKBr, cm⁻¹) 3284, 1732, 1692, 1528, 1350

Mass spectrometry Based on Formula $C_{33}H_{48}N_4O_8$ Calcd. 628.34715 Found 628.34579

NMR (δ, CDCl₃) 0.67 (3H, d, J=7 Hz), 0.69 (3H, d, J=7 Hz), 0.71 (6H, d, J=7 Hz), 1.41 (9H, s), 1.42 (9H, s), 1.94–2.07 (2H, m), 2.17 (3H, s), 2.27 (3H, s), 4.39 (1H, dd, J=8 Hz, 4 Hz), 4.41 (1H, dd, J=8 Hz, 4 Hz), 4.99 (1H, s), 5.25 (1H, s), 5.76 (1H, d, J=8 Hz), 5.87 (1H, d, J=8 Hz), 7.43 (1H, dd, J=8 Hz, 8 Hz), 7.72 (1H, d, J=8 Hz), 8.03 (1H, d, J=8 Hz), 8.18 (1H, s)

EXAMPLE 52

Synthesis of t-butyl 2-(S)-[N-[5-(t-butoxycarbonylmethylcarbamoyl)-1,4-dihydro-2,6-dimethyl-4-(3-nitrophenyl)pyridine-3-carbonyl] amino]-3-methylbutylate (Compound a)

The above compound was prepared in the same reaction scheme as in Example 49 except that the amine compound of formula (XX) employed in Example 49 was replaced by an amine compound of formula (XX) in which R¹³ in the formula is

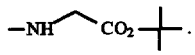

Yield (%) 31.2 (recrystallized from toluene)

Melting point (°C.) 189 (dec.)

IR (νKBr, cm⁻¹) 3332, 1734, 1532, 1350

Mass spectrometry Based on Formula $C_{30}H_{42}N_4O_8$ Calcd. 586.30020 Found 586.29913

NMR (δ, CDCl₃) 0.73 (3H, d, J=7 Hz), 0.74 (3H, d, J=7 Hz), 1.41 (9H, s), 1.42 (9H, s), 1.98–2.09 (1H, m), 2.20 (3H, s), 2.28 (3H, s), 3.86 (2H, d, J=5 Hz), 4.41 (1H, dd, J=9 Hz, 4 Hz), 4.94 (1H, s), 4.93 (1H, s), 5.31 (1H, s), 5.77 (1H, d, J=9 Hz), 5.84 (1H, t, J=5 Hz), 7.44 (1H, dd, J=8 Hz, 8 Hz), 7.70 (1H, d, J=8 Hz), 8.04 (1H, d, J=8 Hz), 8.16 (1H, s)

EXAMPLE 53

Synthesis of t-butyl 2-[N-(1,4-dihydro-2,6-dimethyl-4-(3-nitrophenyl)-5-pyridylpyridine-3-carbonyl)amino]acetate:

The above compound was synthesized in accordance with the following reaction scheme:

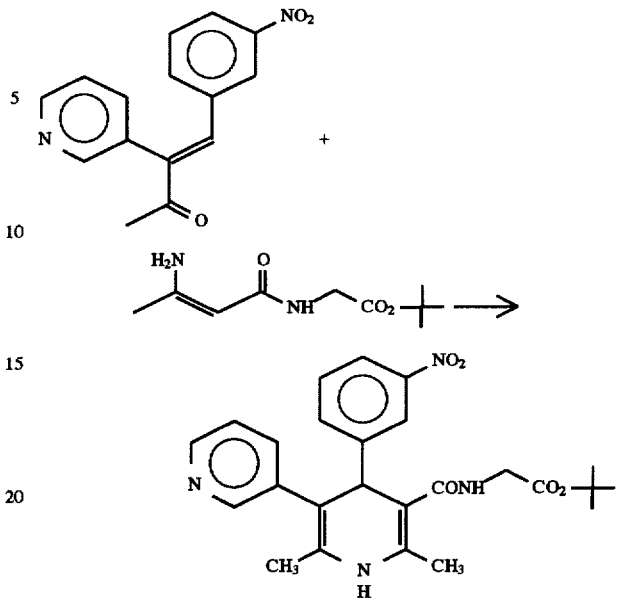

More specifically, a dioxane solution containing 268 mg (1 mmol) of 3-(3-nitrobenzylidene)-3-pyridyl-2-propanone, 1.07 g (5 mmol) of 2-[N-(3-amino-2-butenoyl)amino] acetate, 273 mg (2 mmol) of zinc chloride and 500 mg of Molecular Sieves 4A was refluxed for 2 hours. After cooling to room temperature, the reaction mixture was chromatographed on a silica gel column for purification, whereby 401 mg (86%) of 2-[N-(1,4-dihydro-2,6-dimethyl-4-(3-nitrophenyl)-5-pyridylpyridine-3-carbonyl)-amino]acetate was obtained as an oily material.

IR (νKBr, cm⁻¹) 3320, 1740, 1660, 1530, 1350

Mass spectrometry Based on Formula $C_{25}H_{28}N_4O_5$ Calcd. 464.20593 Found 464.20581

NMR (δ, CDCl₃) 1.42 (9H, s), 1.82 (3H, s), 2.35 (3H, s), 3.87 (2H, d, J=5 Hz), 4.68 (1H, s), 5.37 (1H, s), 5.75 (1H, t, J=5 Hz), 7.21 (1H, dd, J=8 Hz, 5 Hz), 7.33 (1H, d, J=8 Hz), 7.39 (1H, dd, J=8 Hz, 8 Hz), 7.45 (1H, d, J=8 Hz), 8.02 (1H, d, J=8 Hz), 8.08 (1H, s), 8.20 (1H, s), 8.42 (1H, d, J=3 Hz)

EXAMPLE 54

Synthesis of methyl 1,4-dihydro-2,6-dimethyl-4-(S)-(3-nitrophenyl)-5-[N-[1-(pyrrolidin-1-yl)carbonyl-2-(S)-methylpropyl]carbamoyl]pyridine-3-carboxylate:

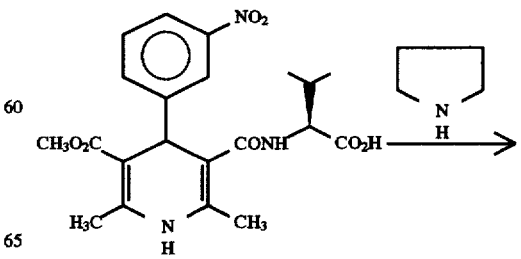

-continued

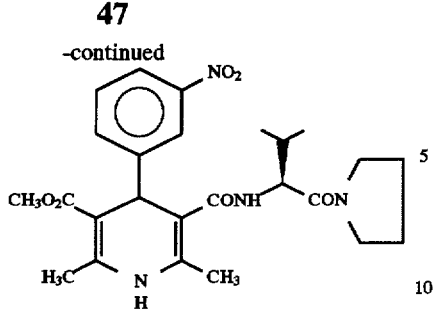

309 mg (1.5 mmol) of 1,3-dicyclohexylcarbodiimido was added to a mixture of 430 mg (1 mmol) of 2-(S)-[N-[1,4-dihydro-2,6-dimethyl-5-methoxycarbonyl-4-(S)-(3-nitrophenyl)pyridine-3-carbonyl]amino]-3-methyl butanoic acid, 149 mg (1.1 mmol) of 1-hydroxybenzotriazole, 71 mg (1 mmol) of pyrrolidine and 10 ml of dichloromethane in a light-shielding condition. The mixture was stirred at room temperature for 4 hours. After washing with water, the reaction mixture was dried over anhydrous sodium sulfate. The thus obtained mixture was then chromatographed on a silica gel column for purification, whereby 188 mg (39%) of the captioned compound was obtained as an oily material.

IR (vKBr, cm$^{-1}$) 3264, 1734, 1532, 1352

Mass spectrometry Based on Formula $C_{25}H_{32}N_4O_6$ Calcd. 484.23213 Found 484.23171

NMR (δ, CDCl$_3$) 0.69 (3H, d, J=7 Hz), 0.83 (3H, d, J=7 Hz), 1.80–1.97 (5H, m), 2.17 (3H, s), 2.35 (3H, s), 3.33–3.50 (4H, m), 3.60 (3H, s), 4.60 (1H, dd, J=9Hz, 6 Hz), 4.99 (1H, s), 5.60 (1H, s), 6.09 (1H, d, J=9 Hz), 7.40 (1H, dd, J=8 Hz, 8 Hz), 7.65 (1H, d, J=8 Hz), 8.01 (1H, d, J=8 Hz), 8.10 (1H, s)

EXAMPLE 55

Synthesis of methyl 1,4-dihydro-2,6 dimethyl-4-(S)-(3-nitrophenyl)-5-[N-[1-(4-phenylpiperazinyl)carbonyl-2-methylpropyl]carbamoyl]pyridine-3-carboxylate:

The above compound was prepared in accordance with the same reaction scheme as in Example 54, except that the amine compound employed in Example 54 was replaced by an amine compound shown below. Specifically the reaction scheme in this example is as follows:

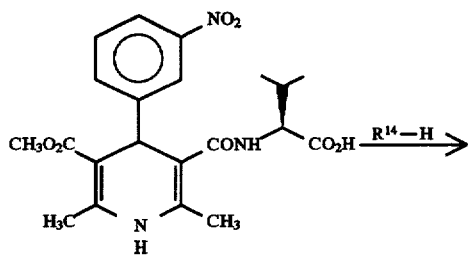

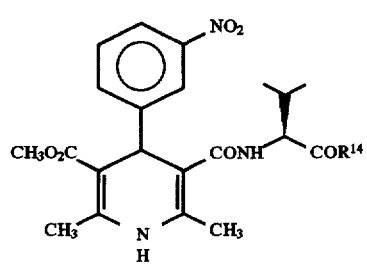

wherein R$^{14}$ is

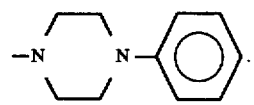

Yield (%) 61.2

Melting point (°C.) oil

IR (vKBr, cm$^{-1}$) 3332, 1684, 1532, 1350

Mass spectrometry Based on Formula $C_{31}H_{37}N_5O_6$ Calcd. 575.27432 Found 575.27261

NMR (δ, CDCl$_3$) 0.69 (3H, d, J=7 Hz), 0.83 (3H, d, J=7 Hz), 1.83–1.95 (1H, m), 2.20 (3H, s), 2.35 (3H, s ), 3.06–3.19 ( 4H, m), 3.55–3.80 (4H, m), 3.61 (3H, s), 4.85 (1H, dd, J=9 Hz, 5 Hz), 5.00 (1H, s), 5.54 (1H, s), 6.14 (1H, d, J=9 Hz), 6.86–6.99 (3H, m), 7.26–7.31 (2H, m), 7.40 (1H, dd, J=8 Hz, 8 Hz), 7.65 (1H, d, J=8 Hz ), 8.00 ( 1H, d, J=8 Hz), 8.12 (1H, s)

EXAMPLE 56

Synthesis of methyl 1,4-dihydro-2,6 dimethyl-4-(S)-(3-nitrophenyl)-5-[N-[1-(4-diphenytmethylpiperazinyl) carbonyl-2-methypropyl]carbamoyl]pyridine-3-carboxylate:

The above compound was prepared in the same reaction scheme as in Example 55 except that the amine compound employed in Example 55 was replaced by an amine compound of formula R$^{14}$-H, in which R$^{14}$ is

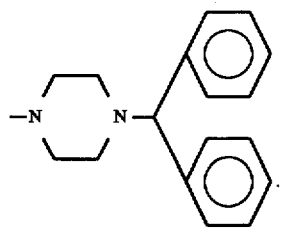

Yield (%) 52.6

Melting point (°C.) oil

IR (vKBr, cm$^{-1}$) 3328, 1734, 1532, 1350

Mass spectrometry Based on Formula $C_{38}H_{43}N_5O_6$ Calcd. 665.32127 Found 665.32132

NMR (δ, CDCl$_3$) 0.63 (3H, d, J=7 Hz), 0.76 (3H, d, J=7 Hz), 1.74–1.88 (1H, m), 2.16 (3H, s), 2.23–2.42 (4H, m), 2.34 (3H, s), 3.36–3.64 (4H, m), 3.59 (3H, s), 4.19 (1H, s), 4.77 (1H, dd, J=9Hz, 5 Hz), 4.98 (1H, s), 5.59 (1H, s), 6.14 (1H, d, J=9 Hz), 7.16–7.31 (6H, m), 7.37–7.42 (5H, m), 7.64 (1H, d, J=8 Hz), 8.01 (1H, d, J=8 Hz), 8.10 (1H, s)

EXAMPLE 57

Synthesis of methyl 1,4-dihydro-2,6-dimethyl-4-(3-nitrophenyl)-5-[N-[(pyrrolidin-1-yl)carbonylmethyl]carbamoyl]pyridine-3-carboxylate:

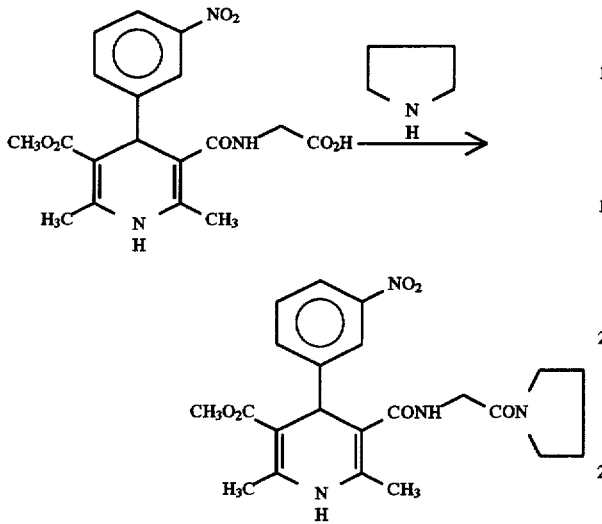

618 mg (3 mmol) of 1,3-dicyclohexylcarbodiimide was added to a mixture of 776 mg (2 mmol) of 2-[N-[1,4-dihydro-2,6-dimethyl-5-methoxycarbonyl-4-(3-nitrophenyl)pyridine-3-carbonyl]amino acetic acid, 298 mg (2.2 mmol) of 1-hydroxybenzotriazole, 142 mg (2 mmol) of pyrrolidine and 20 ml of dichloromethane in a light-shielding condition. The mixture was stirred at room temperature overnight. After washing with water, the reaction mixture was dried over anhydrous sodium sulfate, whereby 442 mg (50%) of the captioned compound was obtained as an oily material.

IR (vKBr, cm$^{-1}$) 3336, 1702, 1528, 1348

Mass spectrometry Based on Formula $C_{22}H_{26}N_4O_6$ Calcd. 442.18519 Found 442.18531

NMR (δ, CDCl$_3$) 1.80–2.03 (4H, m), 2.31 (3H, s), 2.35 (3H, s), 3.34 (2H, t, J=7 Hz), 3.47 (2H, t, J=7 Hz), 3.64 (3H, s), 3.87–4.05 (2H, m), 5.00 (1H, s), 5.63 (1H, s), 6.53–6.62 (1H, m), 7.43 (1H, dd, J=8 Hz, 8 Hz), 7.72 (1H, d, J=8 Hz), 8.02 (1H, d, J=8 Hz), 8.13 (1H, s)

EXAMPLE 58

Synthesis of methyl 1,4-dihydro-2,6-dimethyl-4-(3-nitrophenyl)-5-[N-[(4-phenylpiperazinyl)carbonylmethyl]carbamoyl]pyridine-3-carboxylate:

The above compound was prepared in accordance with the same reaction scheme as in Example 57, except that an amine compound employed in Example 57 was replaced by an amine compound shown below. Specifically the scheme in this example is as follows:

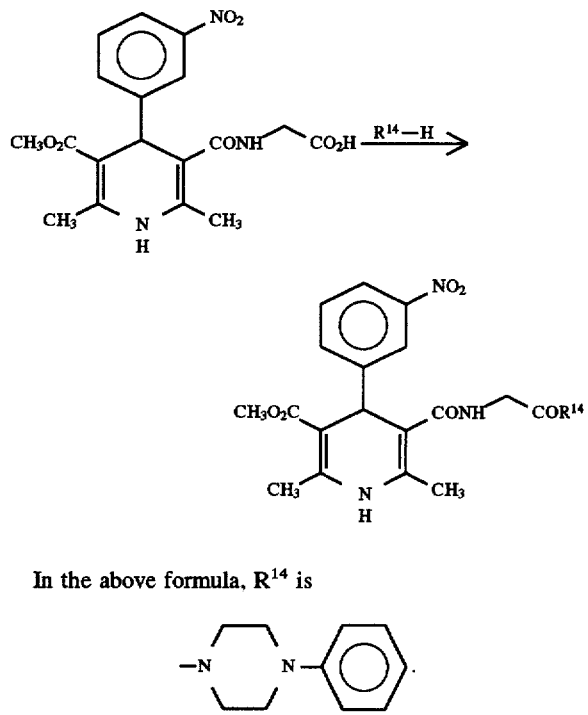

In the above formula, R$^{14}$ is

-N(piperazinyl)N-phenyl.

Yield (%) 35.9

Melting point (°C.) oil

IR (vKBr, cm$^{-1}$) 3340, 1676, 1528, 1344

Mass spectrometry Based on Formula $C_{28}H_{31}N_5O_6$ Calcd. 533.22738 Found 533.22525

NMR (δ, CDCl$_3$) 2.32 (3H, s), 2.35 (3H, s), 3.14–3.19 (4H, m), 3.51–3.60 (2H, m), 3.64 (3H, s), 3.73–3.82 (2H, m), 4.06 (2H, d, J=4 Hz), 5.00 (1H, s), 5.66 (1H, s), 6.57 (1H, d, J=4 Hz), 6.91–6.96 (3H, m), 7.26–7.32 (2H, m), 7.43 (1H, dd, J=8 Hz, 8 Hz), 7.71 (1H, d, J=8 Hz), 8.03 (1H, d, J=8 Hz), 8.14 (1H, s)

EXAMPLE 59

Synthesis of methyl 1,4-dihydro-2,6-dimethyl-4-(3-nitrophenyl)-5-[N-[(4-diphenylmethylpiperazinyl)carbonylmethyl]carbamoyl]pyridine-3-carboxylate:

The above compound was prepared in the same reaction scheme as in Example 58 except that the amine compound employed in Example 58 was replaced by an amine compound of formula R$^{14}$-H, in which R$^{14}$ is

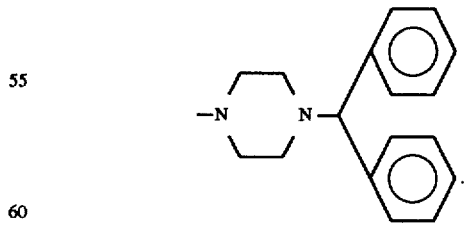

Yield (%) 59.9

Melting point (°C.) oil

IR (vKBr, cm$^{-1}$) 3325, 1658, 1528, 1350

Mass spectrometry Based on Formula $C_{35}H_{37}N_5O_6$ Calcd. 623.27432 Found 623.27522

NMR (δ, CDCl₃) 2.26–2.42 (4H, m), 2.30 (3H, s), 2.34 (3H, s), 3.33–3.40 (2H, m), 3.54–3.65 (2H, m), 3.63 (3H, s), 3.96 (2H, d, J=4 Hz), 4.23 (1H, s), 4.97 (1H, s), 5.64 (1H, s), 6.56 (1H, t, J=4 Hz), 7.16–7.32 (6H, m), 7.35–7.46 (5H, m), 7.69 (1H, d, J=8 Hz), 8.01 (1H, d, J=8 Hz), 8.11 (1H, s)

EXAMPLE 60

Synthesis of 2-methoxyethyl 2-[N-[1,4-dihydro-2,6-dimethyl-5-methoxycarbonyl-4-(3-nitrophenyl)pyridine-3-carbonyl]amino]-3-methylbutylate:

The above compound was prepared in the same reaction scheme as in Example 58 except that the amine compound employed in Example 58 was replaced by a compound of formula R¹⁴-H, in which R¹⁴ is

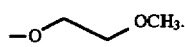

Yield (%) 48
Melting point (°C.) oil
IR (vKBr, cm⁻¹) 3336, 1754, 1682, 1532, 1352
Mass spectrometry Based on Formula $C_{21}H_{25}N_3O_8$ Calcd. 447.16408 Found 447.16318
NMR (δ, CDCl₃) 2.30 (3H, s), 2.33 (3H, s), 3.37 (3H, s), 3.54–3.63 (2H, m), 3.66 (3H, s), 4.03 (2H, d, J=5 Hz), 4.21–4.34 (2H, m), 4.96 (1H, s), 5.80 (1H, s), 5.91 (1H, t, J=5 Hz), 7.43 (1H, dd, J=8 Hz, 8 Hz), 7.69 (1H, d, J=8 Hz), 8.04 (1H, d, J=8 Hz), 8.13 (1H, s)

EXAMPLE 61

Synthesis of ethyl 2-(S)-[N-[1,4-dihydro-2,6-dimethyl-5-methoxycarbonyl-4-(3-nitrophenyl)pyridine-3-carbonyl]amino]-3-methylbutylate:

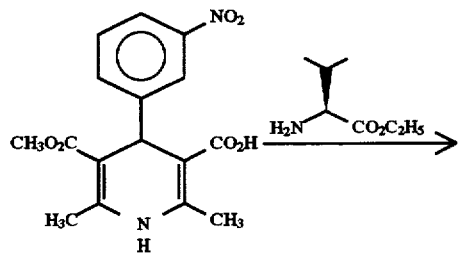

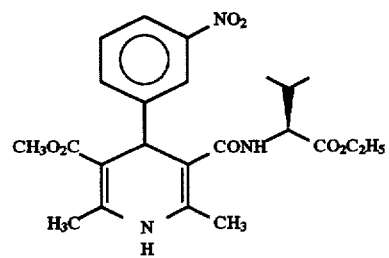

A mixture of 332 mg (1 mmol) of 1,4-dihydro-2,6-dimethyl-5-methoxycarbonyl-4-(3-nitrophenyl)pyridine-3-carboxylic acid, 309 mg (1.5 mmol) of 1,3-dicyclohexylcarbodiimide, 134 mg (1.1 mmol) of 4-dimethylaminopyridine and 10 ml of dichloromethane was stirred at room temperature for one hour. To the mixture, 174 mg (1.2 mmol) of L-valine-t-ethylester was added, and the reaction mixture was stirred at room temperature overnight. After washing with water, the thus obtained mixture was dried over anhydrous sodium sulfate and chromatographed on a silica gel column for purification, whereby 438 mg (95%) of the captioned compound was obtained.

IR (vKBr, cm⁻¹) 3348, 1746, 1654, 1662, 1532, 1348
Mass spectrometry Based on Formula $C_{23}H_{29}N_3O_7$ Calcd. 459.20058 Found 459.20218
NMR (δ, CDCl₃) 0.73 (3H, d, J=7 Hz), 0.78 (3H, d, J=7 Hz), 1.21 (3H, t, J=7 Hz), 2.00–2.15 (1H, m), 2.24 (3H, s), 2.35 (3H, s), 3.63 (3H, s), 4.04–4.20 (2H, m), 4.52 (1H, dd, J=9 Hz, 5 Hz), 4.98 (1H, s), 5.54 (1H, s), 5.74 (1H, dd, J=9 Hz), 7.43 (1H, dd, J=8 Hz, 8 Hz), 7.67 (1H, d, J=8 Hz), 8.05 (1H, d, J=8 Hz), 8.14 (1H, s)

EXAMPLE 62

Synthesis of ethyl 2-[N-[1,4-dihydro-2,6-dimethyl-5-methoxycarbonyl-4-(3-nitrophenyl)pyridine-3-carbonyl]amino]acetate:

The above compound was prepared in accordance with the same reaction scheme as in Example 61 except that the amine compound employed in Example 61 was replaced by an amine compound shown below. Specifically the reaction scheme in this example is as follows:

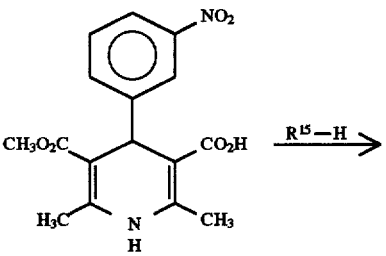

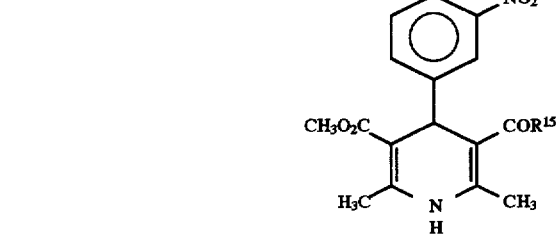

wherein R¹⁵ is

Yield (%) 75
Melting point (°C.) oil
IR (vKBr, cm⁻¹) 3332, 1748, 1682, 1532, 1352
Mass spectrometry Based on Formula $C_{20}H_{23}N_3O_7$ Calcd. 417.15352 Found 417.15282
NMR (δ, CDCl₃) 1.25 (3H, t, J=7 Hz), 2.31 (3H, s), 2.34 (3H, s), 3.66 (3H, s), 3.98 (2H, d, J=5 Hz), 4.17 (2H, q, J=7 Hz), 4.96 (1H, s), 5.83 (1H, s), 5.90 (1H, t, J=5 Hz), 7.43 (1H, dd, J=8 Hz, 8 Hz), 7.69 (1H, d, J=8 Hz), 8.05 (1H, d, J=8 Hz), 8.14 (1H, s)

EXAMPLE 63

Synthesis of isopropyl 2-[N-[1,4-dihydro-2,6-dimethyl-5-methoxycarbonyl-4-(3-nitrophenyl)pyridine-3-carbonyl]amino]acetate:

The above compound was prepared in the same reaction scheme as in Example 62 except that the amine compound employed in Example 62 was replaced by an amine compound of formula $R^{15}$-H, in which R is

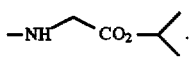

Yield (%) 58

Melting point (°C.) oil

IR (vKBr, cm$^{-1}$) 3332, 1742, 1682, 1532, 1352

Mass spectrometry Based on Formula $C_{21}H_{25}N_3O_7$ Calcd. 431.16924 Found 431.16954

NMR (δ, CDCl$_3$) 1.225 (3H, t, J=6 Hz), 1.233 (3H, d, J=6 Hz), 2.31 (3H, s), 2.34 (3H, s), 3.66 (3H, s), 3.95 (2H, d, J=5 Hz), 4.96 (1H, s), 5.03 (1H, m), 5.83 (1H, s), 5.90 (1H, t, J=5 Hz), 7.43 (1H, dd, J=8 Hz, 8 Hz), 7.69 (1H, d, J=8 Hz), 8.04 (1H, d, J=8 Hz), 8.14 (1H, s)

EXAMPLE 64

Synthesis of ethyl 3-[N-[1,4-dihydro-2,6-dimethyl-5-methoxycarbonyl-4-(3-nitrophenyl)pyridine-3-carbonyl]amino]propionate:

The above compound was prepared in the same reaction scheme as in Example 62 except that the amine compound employed in Example 62 was replaced by an amine compound of formula $R^{15}$-H, in which $R^{15}$ is

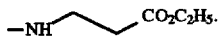

Yield (%) 58

Melting point (°C.) oil

IR (vKBr, cm$^{-1}$) 3332, 1736, 1684, 1532, 1352

Mass spectrometry Based on Formula $C_{21}H_{25}N_3O_7$ Calcd. 431.16922 Found 431.16641

NMR (δ, CDCl$_3$) 1.23 (3H, t, J=7 Hz), 2.25 (3H, s), 2.33 (3H, s), 2.38–2.47 (2H, m), 3.38– 3.54 (2H, m), 3.65 (3H, s), 4.07 (2H, d, J=7 Hz), 4.90 (1H, s), 5.64 (1H, s), 6.03 (1H, t, J=6 Hz), 7.41 (1H, dd, J=8 Hz, 8 Hz), 7.64 (1H, d, J=8 Hz), 8.03 (1H, d, J=8 Hz), 8.11 (1H, s)

EXAMPLE 65

Synthesis of ethyl 2-[N-[1,4-dihydro-2,6-dimethyl-5-methoxycarbonyl-4-(3-nitrophenyl)pyridine-3-carbonyl-N-methylamino]acetate:

The above compound was prepared in the same reaction scheme as in Example 62 except that the amine compound employed in Example 62 was replaced by an amine compound of formula $R^{15}$-H, in which $R^{15}$ is

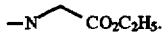

Yield (%) 63

Melting point (°C.) oil

IR (vKBr, cm$^{-1}$) 3320, 1748, 1698, 1530, 1352

Mass spectrometry Based on Formula $C_{21}H_{25}N_3O_7$ Calcd. 431.16922 Found 431.16689

NMR (δ, CDCl$_3$) 1.26 (3H, t, J=7 Hz), 1.93 (3H, s), 2.41 (3H, s), 2.73 (3H, s), 3.56 (3H, s), 3.80–3.94 (1H, m), 4.10–4.35 (1H, m), 4.93 (1H, s), 5.46 (1H, s), 7.41 (1H, dd, J=8 Hz, 8 Hz), 7.58 (1H, d, J=8 Hz), 8.03 (1H, d, J=8 Hz), 8.07 (1H, s)

EXAMPLE 66

Synthesis of t-butyl 2-(S)-[N-[[N-[1,4-dihydro-2,6-dimethyl-5-methoxycarbonyl-4-(3-nitrophenyl)pyridine-3-carbonyl]amino]acetyl]amino]-3-methylbutylate:

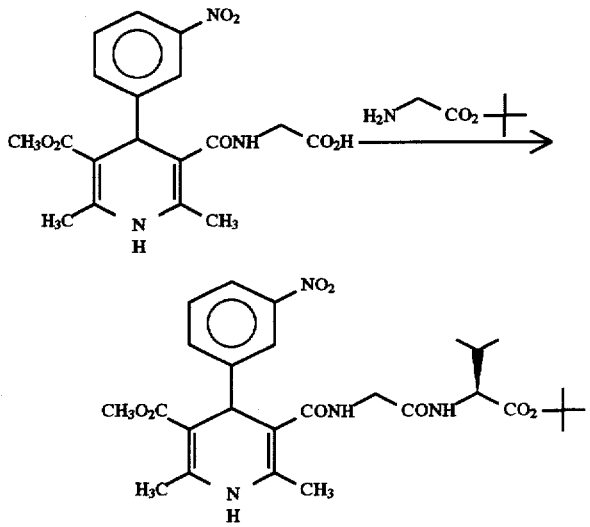

In a light-shielding condition, a mixture of 388 mg (1 mmol) of 2-[N-[1,4-dihydro-2,6-dimethyl-5-methoxycarbonyl-4-(3-nitrophenyl)pyridine-3-carbonyl]amino]acetic acid, 131 mg (1.3 mmol) of triethylamine and 10 ml of dried tetrahydrofuran was cooled to 0° to 5° C. in an atmosphere of argon gas. To the above mixture, 130 mg. (1.2 mmol) of ethyl chlotocarbonate was added dropwise and the reaction mixture was stirred for one hour. To the reaction mixture, 225 mg (1.3 mmol) of L-valine-t-butylester was then added and the mixture was stirred at room temperature overnight. The tetrahydrofuran was distilled away under reduced pressure and the residue was dissolved in dichloromethane. After washing with water, the thus obtained mixture was dried over anhydrous sodium sulfate and chromatographed on a silica gel column for purification, whereby 62 mg (11.4%) of the captioned compound was obtained as an oily material.

IR (vKBr, cm$^{-1}$) 3330, 1734, 1668, 1532, 1352

Mass spectrometry Based on Formula $C_{27}H_{36}N_4O_8$ Calcd. 531.25800 Found 531.25891

NMR (δ, CDCl$_3$) 0.85 (3H, d, J=7 Hz), 0.86 (3/2H, d, J=7 Hz), 0.89 (3/2H, d, J=7 Hz), 1.44 (9/2H, s), 1.46 (9/2H, s), 2.03–2.19 (1H, m), 2.30 (3H, s), 2.32 (3H, s), 3.66 (3H, s), 3.90 (1H, dd, J=17 Hz, 5 Hz), 4.00 (1H, dd, J=17 Hz, 5 Hz), 4.38 (1H, dd, J=9 Hz, 5 Hz), 4.97 (1H, s), 6.02–6.16 (1H, m), 6.28 (1H, br. s), 6.42–6.58 (1H, m), 7.41 (1H, dd, J=8 Hz, 8 Hz), 7.69 (1H, d, J=8 Hz), 8.03 (1H, d, J=8 Hz), 8.13 (1H, s)

EXAMPLE 67

Synthesis of ethyl 1-[N-[1,4-dihydro-2,6-dimethyl-5-methoxycarbonyl-4-(3-nitrophenyl)pyridine-3-carbonyl]amino]cyclohexanecarboxylate:

The above compound was prepared in accordance with the same reaction scheme as in Example 66 except that the amine compound employed in Example 66 was replaced by an amine compound shown below. Specifically the reaction scheme in this example is as follows:

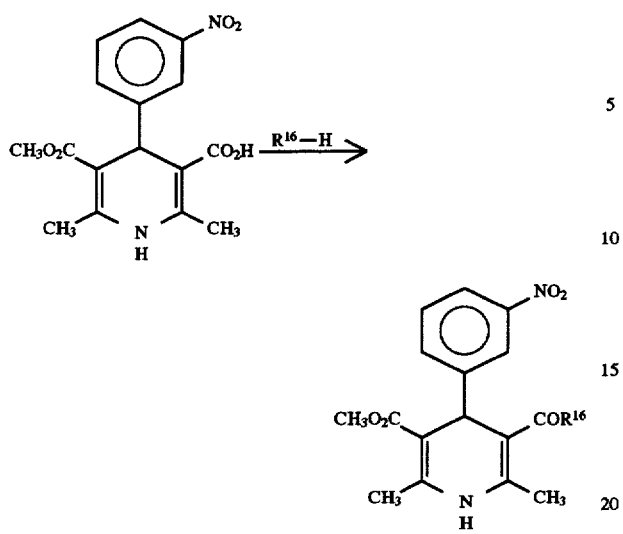

wherein R[16] is

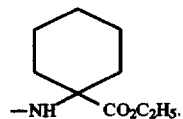

Yield (%) 55

Melting point (°C.) oil

IR (vKBr, cm$^{-1}$) 3340, 1740, 1682, 1532, 1350

Mass spectrometry Based on Formula $C_{25}H_{31}N_3O_7$ Calcd. 485.21617 Found 485.21817

NMR (δ, CDCl$_3$) 0.88–2.02 (10H, m), 1.18 (3H, t, J=7 Hz), 2.26 (3H, s), 2.33 (3H, s), 3.65 (3H, s), 4.05 (2H, m), 4.96 (1H, s), 5.38 (1H, s), 5.71 (1H, s), 7.45 (1H, dd, J=8 Hz, 8 Hz), 7.70 (1H, d, J=8 Hz), 8.07 (1H, d, J=8 Hz), 8.16 (1H, s)

EXAMPLE 68

Synthesis of ethyl 2-[N-[1,4-dihydro-2,6-dimethyl-5-methoxycarbonyl-4-(3-nitrophenyl)pyridine-3-carbonyl]amino]isobutyrate:

The above compound was prepared in the same reaction scheme as in Example 66 except that the amine compound of formula R[16]-H employed in Example 66 was replaced by an amine compound of formula R[16]-H in which R[16] is

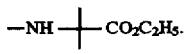

Yield (%) 60

Melting point (°C.) oil

IR (vKBr, cm$^{-1}$) 3332, 1740, 1682, 1532, 1352

Mass spectrometry Based on Formula $C_{22}H_{27}N_3O_7$ Calcd. 445.18480 Found 445.18340

NMR (δ, CDCl$_3$) 1.21 (3H, t, J=7 Hz), 1.43 (3H, s), 1.47 (3H, s), 2.22 (3H, s), 2.35 (3H, s), 3.63 (3H, s), 4.07–4.22 (2H, m), 4.93 (1H, s), 5.55 (1H, s), 5.91 (1H, s), 7.43 (1H, dd, J=8 Hz, 8 Hz), 7.66 (1H, d, J=8 Hz), 8.05 (1H, d, J=8 Hz), 8.12 (1H, s)

EXAMPLE 69

Synthesis of ethyl 2-[N-[1,4-dihydro-2,6-dimethyl-5-methoxycarbonyl-4-(3-nitrophenyl)pyridine-3-carbonyl]amino]benzoate:

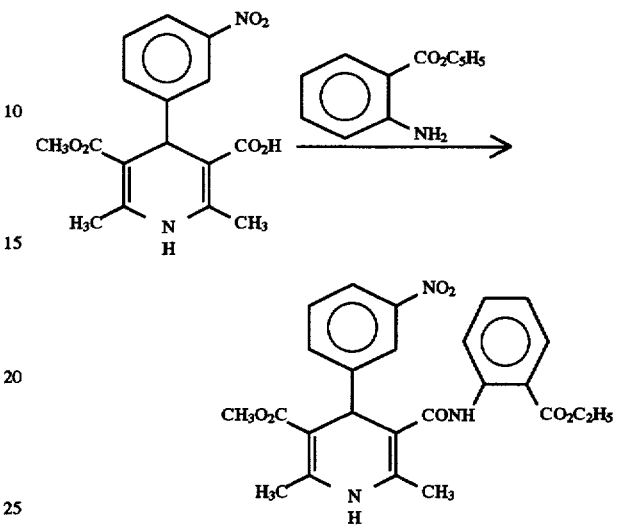

Under an ice-cooled condition, 332 mg (1 mmol) of 1,4-dihydro-2,6-dimethyl-5-methoxycarbonyl-4-(3-nitrophenyl) pyridine-3-carboxylic acid was suspended in dried dichloromethane. The mixture was stirred with addition of 229 mg (1.1 mmol) of phosphorus pentachloride little by little for one hour. At –30° C., 1650 mg (10 mmol) of ethyl anthranilate was added to the reaction mixture. The reaction mixture was further stirred at room temperature for one hour. After washing with water, the raction mixture was dried over anhydrous sodium sulfate. The thus obtained mixture was chromatographed on a silica gel column for purification, whereby 486 mg (100%) of the captioned compound was obtained as an oily material.

IR (vKBr, cm$^{-1}$) 3336, 1690, 1532, 1350

Mass spectrometry Based on Formula $C_{25}H_{25}N_3O_7$ Calcd. 479.16920 Found 479.16710

NMR (δ, CDCl$_3$) 1.39 (3H, t, J=7 Hz), 2.36 (3H, s), 2.38 (3H, s), 3.70 (3H, s), 4.35 (2H, q, J=7 Hz), 5.26 (1H, s), 5.76 (1H, s), 7.03 (1H, dd, J=8 Hz, 8 Hz), 7.38 (1H, dd, J=8 Hz, 8 Hz), 7.48 (1H, dd, J=8 Hz, 8 Hz), 7.71 (1H, d, J=8 Hz), 8.00 (2H, d, J=8 Hz), 8.22 (1H, s), 8.64 (1H, d, J=8 Hz), 11.23 (1H, s)

EXAMPLE 70

Synthesis of ethyl 3-[N-[1,4-dihydro-2,6-dimethyl-5-methoxycarbonyl-4-(3-nitrophenyl)pyridine-3-carbonyl]amino]pyrazine-2-carboxylate:

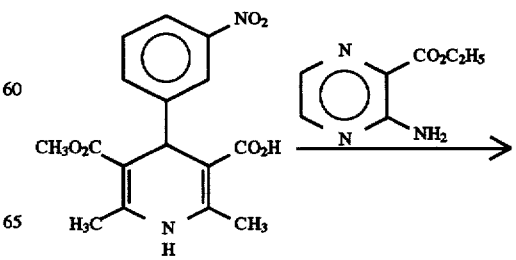

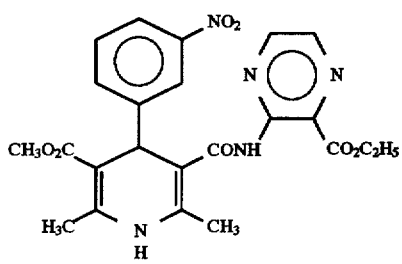

The procedure for Example 69 was repeated except that the ethyl anthranilate employed in Example 69 was replaced by ethyl 3-aminopyrazine-2-carboxylate, whereby the captioned compound was obtained as an oily material.

IR (νKBr, cm$^{-1}$) 3316, 1732, 1690, 1530, 1350

Mass spectrometry Based on Formula $C_{23}H_{23}N_5O_7$ Calcd. 481.15981 Found 481.16061

NMR (δ, CDCl$_3$) 1.45 (3H, t, J=7 Hz), 2.37 (3H, s), 2.48 (3H, s), 3.74 (3H, s), 4.49 (2H, q, J=7 Hz), 5.27 (1H, s), 5.99 (1H, s), 7.40 (1H, dd, J=8 Hz, 8 Hz), 7.75 (1H, d, J=8 Hz), 8.03 (1H, d, J=8 Hz), 8.24 (1H, s), 8.35 (1H, d, J=2.4 Hz), 8.56 (1H, d, J=2.4 Hz), 10.85 (1H, s)

EXAMPLE 71

Synthesis of t-butyl 2-[N-[1,4-dihydro-6-methyl-5-methoxycarbonyl-4-(3-nitrophenyl)-2-phenylpyridine-3-carbonyl]amino]-3-methylbutylate:

The above compound was synthesized in accordance with the following reaction scheme:

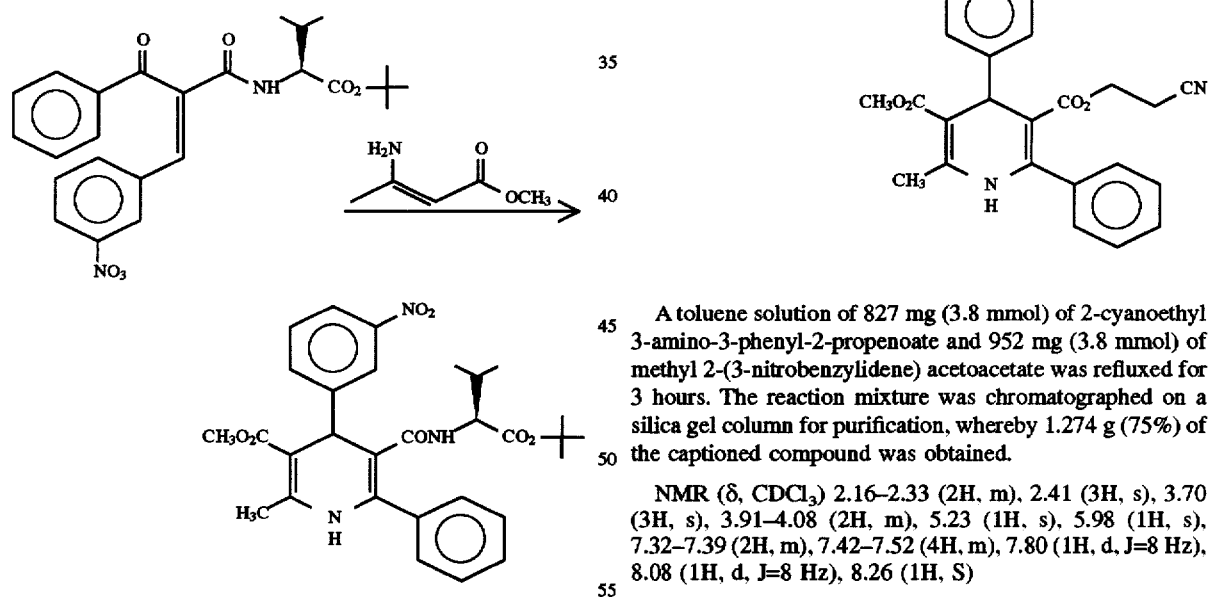

More specifically, a mixture of 366 mg (0.81 mmol) of t-butyl 2-(S)-[N-[2-benzoyl-3-(3-nitrophenyl)-2-propenoyl]amino]-3-methylbutylate, 95 mg (0.81 mmol) of methyl 3-aminocrotonate and 2 ml of toluene was refluxed for 5 hours. After cooling to room temperature, the reaction mixture was chromatographed on a silica gel column for purification, whereby the 198 mg (44%) of a diastereo mixture was obtained as an oily material.

IR (νKBr, cm$^{-1}$) 3308, 1734, 1704, 1682, 1532, 1352

Mass spectrometry Based on Formula $C_{30}H_{35}N_3O_7$ Calcd. 549.24747 Found 549.24837

NMR (δ, CDCl$_3$) 0.36 (3/5H, d, J=7 Hz), 0.40 (12/5H, d, J=7 Hz), 0.44 (3/5H, d, J=7 Hz), 0.55 (12/5H, d, J=7 Hz), 1.27 (36/5H, s), 1.34 (9/5H, s), 1.64–1.83 (1H, m), 2.39 (3H, s), 3.63 (3H, s), 4.08 (1H, dd, J=9 Hz, 5 Hz), 4.14 (1H, dd, J=9 Hz, 5 Hz), 5.15 (1/5H, s), 5.28 (4/5H, s), 5.36 (4/5H, d, J=9 Hz), 5.39 (1/5H, d, J=9 Hz), 6.03 (4/5H, s), 6.10 (1/5H, s), 7.29–7.60 (6H, m), 7.75 (4/5H, d, J=8 Hz), 7.78 (1/5H, d, J=8 Hz), 7.90–8.03 (1H, m), 8.22 (4/5H, s), 8.23 (1/5H, s)

Reference Example 1

Synthesis of 2-cyanoethyl methyl 1,4-dihydro-6-methyl-4-(3-nitrophenyl)-2-phenylpyridine-3,5-dicarboxylate:

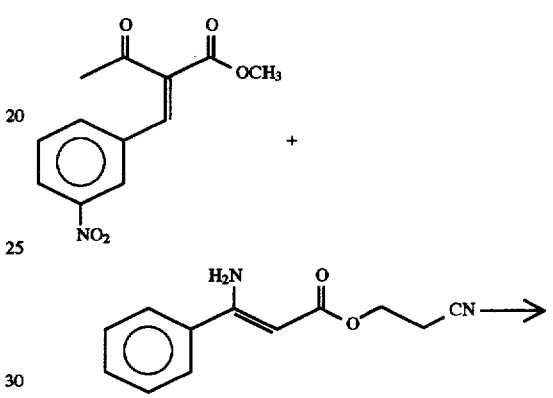

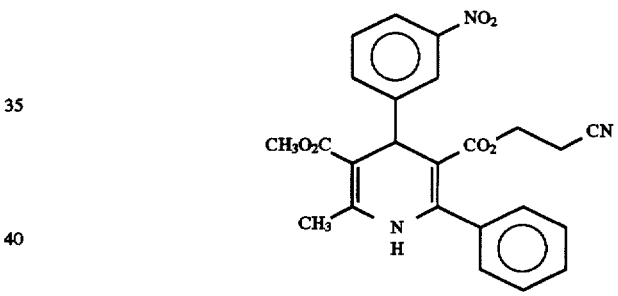

A toluene solution of 827 mg (3.8 mmol) of 2-cyanoethyl 3-amino-3-phenyl-2-propenoate and 952 mg (3.8 mmol) of methyl 2-(3-nitrobenzylidene) acetoacetate was refluxed for 3 hours. The reaction mixture was chromatographed on a silica gel column for purification, whereby 1.274 g (75%) of the captioned compound was obtained.

NMR (δ, CDCl$_3$) 2.16–2.33 (2H, m), 2.41 (3H, s), 3.70 (3H, s), 3.91–4.08 (2H, m), 5.23 (1H, s), 5.98 (1H, s), 7.32–7.39 (2H, m), 7.42–7.52 (4H, m), 7.80 (1H, d, J=8 Hz), 8.08 (1H, d, J=8 Hz), 8.26 (1H, S)

Reference Example 2

Synthesis of 2-cyanoethyl methyl 1,4-dihydro-4,6-dimethyl-2-phenylpyridine-3,5-dicarboxylate:

The above compound was prepared in accordance with the same reaction scheme as in Reference Example 1 except that the ketoester derivative and the enamine derivative employed in Reference Example 1 were respectively replaced by a ketoester derivative of formula (XXI) and an enamine derivative of formula (XXII) shown below. Specifically the reaction scheme in this example is as follows:

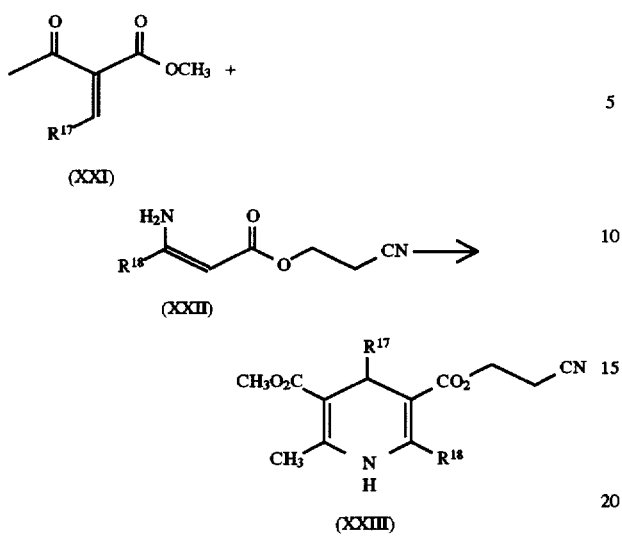

(XXI)

(XXII)

(XXIII)

wherein $R^{17}$ in formula (XXI) is —$CH_3$ and $R^{18}$ in formula (XXI) is

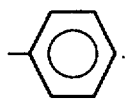

Yield (%) 78.9

NMR (δ, CDCl₃) 1.14 (3H, d, J=7 Hz), 2.31 (3H, s), 2.32 (2H, t, J=6 Hz), 3.75 (3H, s), 3.95 (1H, q, J=7 Hz), 4.03 (1H, ddd, J=11 Hz, 6 Hz, 6 Hz), 4.10 (1H, ddd, J=11 Hz, 6 Hz, 6 Hz), 5.80 (1H, s), 7.28–7.35 (2H, m), 7.39–7.48 (3H, m)

Reference Example 3

Synthesis of 2-cyanoethyl methyl 1,4-dihydro-2-(2-methoxy-4-methylthiophenyl)-6-methyl-4-(3-nitrophenyl)pyridine-3,5-dicarboxylate:

The above compound was prepared in the same reaction scheme as in Reference Example 2 except that the ketoester derivative and the enamine derivative employed in Reference Example 2 were respectively replaced by a ketoester derivative of formula (XXI) in which $R^{17}$ is

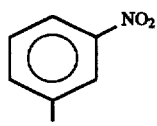

and an enamine derivative of formula (XXII) in which $R^{18}$ is

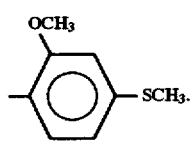

Yield (%) 84.7

NMR (δ, CDCl₃) 2.27 (2H, d, J=6 Hz), 2.36 (3H, s), 2.53 (3H, s), 3.72 (3H, s), 3.85 (3H, s), 3.95 (1H, ddd, J=11 Hz, 6 Hz, 6 Hz), 4.03 (1H, ddd, J=11 Hz, 6 Hz, 6 Hz), 5.24 (1H, s), 5.91 (1H, S), 6.85 (1H, s), 6.87 (1H, d, J=8 Hz), 7.11 (1H, d, J=8 Hz), 7.44 (1H, dd, J=8 Hz, 8 Hz), 7.82 (1H, d, J=8 Hz), 8.05 (1H, d, J=8 Hz), 8.36 (1H, S)

Reference Example 4

Synthesis of 2-cyanoethyl methyl 2-ethyl-1,4-dihydro-6-methyl-4-(3-nitrophenyl)pyridine-3,5-dicarboxylate:

The above compound was prepared in the same reaction scheme as in Reference Example 2 except that the ketoester derivative and the enamine derivative employed in Reference Example 2 were respectively replaced by a ketoester derivative of formula (XXI) in which $R^{17}$ is

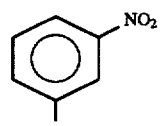

and an enamine derivative of formula (XXII) in which $R^{18}$ is —$CH_2CH_3$.

Yield (%) 60.3

NMR (δ, CDCl₃) 1.26 (3H, t, J=7.4 Hz), 2.38 (3H, s), 2.65 (2H, t, J=6 Hz), 2.67–2.89 (2H, m), 3.66 (3H, s), 4.19–4.33 (2H, m), 5.10 (1H, s), 5.85 (1H, s), 7.40 (1H, dd, J=8 Hz, 8 Hz), 7.67 (1H, d, J=8 Hz), 8.02 (1H, d, J=8 Hz), 8.10 (1H, S)

Reference Example 5

Synthesis of 1,4-dihydro-5-methoxycarbonyl-6-methyl-4-(3-nitrophenyl)-2-phenylpyridine-3-carboxylic acid:

The above compound was obtained in accordance with the following reaction scheme:

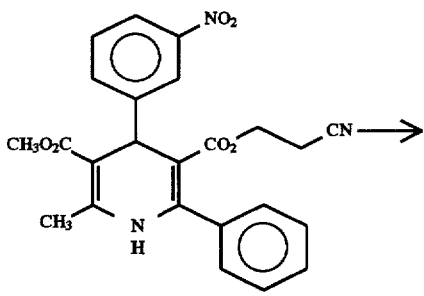

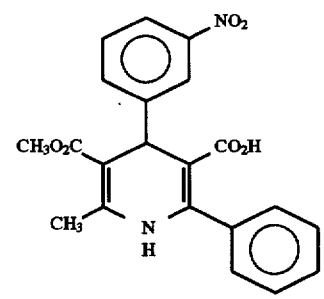

More specifically, 557 mg (2.89 mmol) of a 28% sodium methoxide was added to a dried mixed solution of methanol and methylene chloride (1:1) containing 1.174 g (2.62 mmol) of 2-cyanoethyl methyl 1,4-dihydro-6-methyl-4-(3-nitrophenyl)-2-phenylpyridine-3,5-dicarboxylate synthesized in Reference Example 1. The mixture was stirred at room temperature for 2 hours and 100 ml of methylene chloride was added thereto. The reaction mixture was then extracted with 100 ml of water. The water layer was acidified by 1N hydrochloric acid and extracted with ethyl acetate. The ethyl acetate layer was dried over anhydrous sodium sulfate, and the solvent was distilled away therefrom under reduced pressure, whereby 993 mg (96.2%) of the captioned compound was obtained.

Melting point (°C.) 183.3–185.9

IR (vKBr, cm⁻¹) 3272, 1690, 1670, 1528, 1352

NMR (δ, Acetone-d6) 2.47 (3H, s), 3.67 (3H, s), 5.30 (1H, s), 7.32–7.48 (5H, m), 7.59 (1H, dd, J=8 Hz, 8 Hz), 7.89 (1H, d, J=8 Hz), 8.07 (1H, d, J=8 Hz), 8.23 (1H, s), 8.30 (1H, s), 10.10 (1H, br.S)

Reference Example 6

Synthesis of 1,4-dihydro-5-methoxycarbonyl-4,6-dimethyl-2-phenylpyridine-3-carboxylic acid:

The above compound was prepared in accordance with the same reaction scheme as in Reference Example 5 except that the cyanoethyl derivative employed in Reference Example 5 was replaced by a cyanoethyl derivative shown below. Specifically the reaction scheme in this example is as follows:

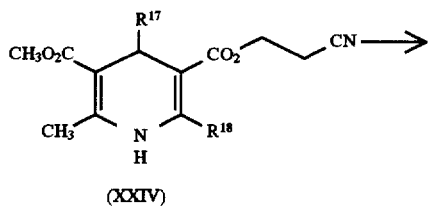

(XXIV)

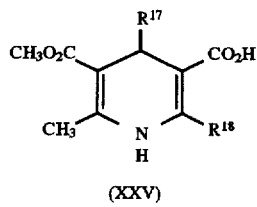

(XXV)

wherein R¹⁷ is

and R¹⁸ is

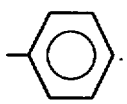

Yield (%) 61.7
Melting point (°C.) 172.1–175.7
IR (vKBr, cm⁻¹) 3260, 1684, 1666
NMR (δ, CD₃OD) 1.05 (3H, d, J=6 Hz), 2.27 (3H, s), 3.72 (3H, s), 3.87 (1H, q, J=6 Hz), 7.27–7.34 (2H, m), 7.34–7.41 (3H, m)

Reference Example 7

Synthesis of 1,4-dihydro-5-methoxycarbonyl-2-(2-methoxy-4-methylthiophenyl)-6-methyl-4-(3-nitrophenyl)pyridine-3-carboxylic acid:

The above compound was prepared in the same reaction scheme as in Reference Example 6 except that the cyanoethyl derivative of formula (XXIV) employed in Reference Example 6 was replaced by a cyanoethyl derivative of formula (XXIV) in which R¹⁷ is

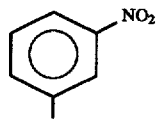

and R¹⁸ is

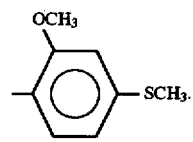

Yield (%) 67

Melting point (°C.) 198.9–201.6

IR (vKBr, cm⁻¹) 3340, 1714, 1682, 1530, 1352

NMR (δ, Acetone-d6) 2.39 (3H, s), 2.53 (3H, s), 3.69 (3H, s), 3.82 (3H, s), 5.12 (1H, s), 6.84 (1H, d, J=8 Hz), 6.90 (1H, s), 7.14 (1H, d, J=8 Hz), 7.56 (1H, dd, J=8 Hz, 8 Hz), 7.92 (1H, d, J=8 Hz), 8.04 (1H, d, J=8 Hz), 8.07 (1H, s), 8.39 (1H, s), 9.95 (1H, br.S)

Reference Example 8

Synthesis of 2-ethyl-1,4-dihydro-5-methoxycarbonyl-6-methyl-4-(3-nitrophenyl)pyridine-3-carboxylate:

The above compound was prepared in the same reaction scheme as in Reference Example 6 except that the cyanoethyl derivative of formula (XXIV) employed in Reference Example 6 was replaced by a cyanoethyl derivative of formula (XXIV) in which R¹⁷ is

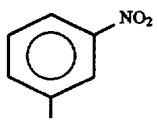

and R¹⁸ is —CH₂CH₃.

Yield (%) 96.4

Melting point (°C.) 174.9–176.7

IR (vKBr, cm⁻¹) 3348, 1660, 1532, 1352

NMR (δ, Acetone-d6) 1.21 (3H, t, J=7 Hz), 2.37 (3H, s), 2.83 (2H, q, J=7 Hz), 3.62 (3H, s), 5.19 (1H, s), 7.52 (1H, dd, J=8 Hz, 8 Hz), 7.75 (1H, d, J=8 Hz), 8.01 (1H, d, J=8 Hz), 8.13 (1H, s), 8.16 (1H, s), 9.95 (1H, br. S)

EXAMPLE 72

Synthesis of t-butyl 2-[N-(1,4-dihydro-5-methoxycarbonyl-6-methyl-4-(3-nitrophenyl)-2-phenylpyridine-3-carbonyl)amino]acetate:

The above compound was synthesized in accordance with the following reaction scheme:

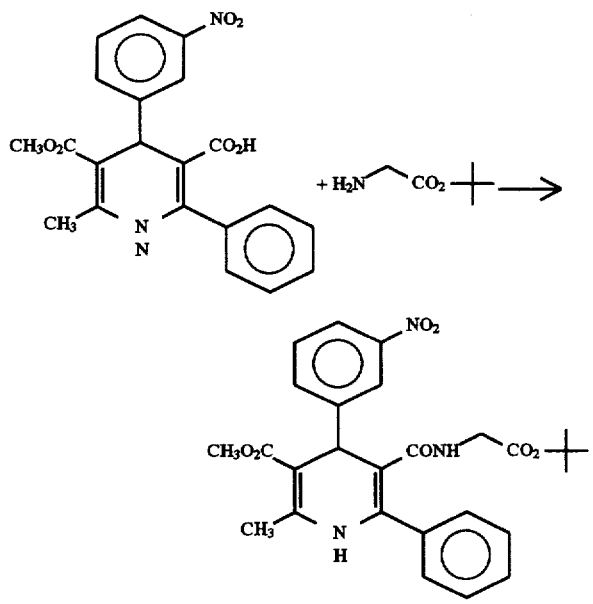

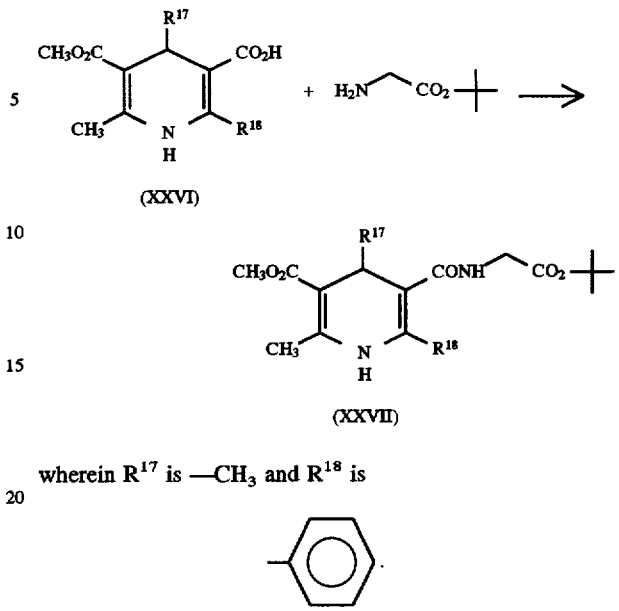

wherein $R^{17}$ is —$CH_3$ and $R^{18}$ is

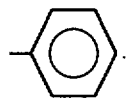

More specifically, a dried methylene chloride solution containing 394 mg (1 mmol) of 1,4-dihydro-5-methoxycarbonyl- 6-methyl-4-(3-nitrophenyl)-2-phenylpyridine-3-carboxylate, 309 mg (1.5 mmol) of dicyclohexylcarbodiimide and 134 mg (1.1 mmol) of dimethylaminopyridine was stirred for one hour. To this reaction mixture, 157 mg (1.2 mmol) of glycine t-butyl ester was added and the reaction mixture was refluxed for 2 hours. Insoluble components were removed from the reaction mixture by filtration and the reaction mixture was chromatographed on a silica gel column for purification, whereby 508 mg (100%) of the captioned compound was obtained as an oily material.

IR (vKBr, cm$^{-1}$) 3330, 1742, 1682, 1530, 1350

Mass spectrometry Based on Formula $C_{27}H_{29}N_3O_7$ Calcd. 507.20051 Found 507.20109

NMR (δ, CDCl$_3$) 1.33 (9H, s), 2.42 (3H, s), 3.54 (1H, dd, J=19 Hz, 5 Hz), 3.67 (3H, s), 3.68, (1H, dd, J=19 Hz, 5 Hz), 5.25 (1H, s), 5.32 (1H, t, J=5 Hz), 5.79 (1H, s), 7.43 (1H, dd, J=8H, 8 Hz), 7.44–7.51 (5H, m), 7.79 (1H, d, J=8 Hz), 8.04 (1H, d, J=8 Hz), 8.25 (1H, S)

EXAMPLE 73

Synthesis of t-butyl 2-[N-(1,4-dihydro-5-methoxycarbonyl-4,6-dimethyl-2-phenylpyridine-3-carbonyl)amino]acetate:

The above compound was synthesized in accordance with the same reaction scheme as in Example 72 except that the carboxylic acid derivative employed in Example 72 was replaced by a carboxylic acid derivative shown below. Specifically the reaction scheme in this example is as follows:

Melting point (°C.) 133 (recrystallized from acetonitrile)
Yield (%) 84.9
IR (vKBr, cm$^{-1}$) 3296, 1748, 1660
Mass spectrometry Based on Formula $C_{22}H_{28}N_2O_5$ Calcd. 400.19979 Found 400.20005
NMR (δ, CDCl$_3$) 1.16 (3H, d, J=7 Hz), 1.38 (9H, s), 2.32 (3H, s), 3.69 (1H, d, J=18 Hz, 5 Hz), 3.79 (1H, dd, J=18 Hz, 5 Hz), 3.72 (3H, s), 3.90 (1H, q, J=7 Hz), 5.48 (1H, t, J=5 Hz), 5.57 (1H, s), 7.36–7.45 (5H, m)

EXAMPLE 74

Synthesis of t-butyl 2-[N-(1,4-dihydro-5-methoxycarbonyl-2-(2-methoxy-4-methylthiophenyl)-6-methyl-4-(3-nitrophenyl)pyridine-3-carbonyl)amino] acetate:

The above compound was synthesized in the same reaction scheme as in Example 73 except that the carboxylic acid derivative of formula (XXVI) employed in Example 73 was replaced by a carboxylic acid derivative of formula (XXVI) in which $R^{17}$ is

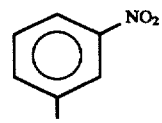

and $R^{18}$ is

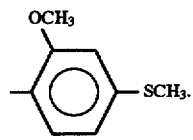

Melting point (°C.) oil
Yield (%) 72
IR (vKBr, cm$^{-1}$) 3304, 1740, 1682, 1532, 1350
Mass spectrometry Based on Formula $C_{29}H_{33}N_3O_8S$ Calcd. 583.19879 Found 583.19700
NMR (δ, CDCl$_3$) 1.34 (9H, s), 2.34 (3H, s), 2.51 (3H, s), 3.56 (1H, dd, J=19 Hz, 5 Hz), 3.67 (1H, dd, J=19 Hz, 5 Hz), 3.69 (3H, s), 3.91 (3H, s), 5.29 (1H, s), 5.73 (1H, s), 5.73 (1H, t, J=5 Hz), 6.86 (1H, d, J=7.8 Hz), 6.88 (1H, s), 7.20 (1H, d, J=7.5 Hz), 7.41 (1H, dd, J=8H, 8 Hz), 7.82 (1H, d, J=8 Hz), 8.03 (1H, d, J=8 Hz), 8.38 (1H, S)

EXAMPLE 75

Synthesis of t-butyl 2-[N-(2-ethyl-1,4-dihydro-5-methoxycarbonyl-6-methyl-4-(3-nitrophenyl)pyridine-3-carbonyl)amino]acetate:

The above compound was synthesized in the same reaction scheme as in Example 73 except that the carboxylic acid derivative of formula (XXVI) employed in Example 73 was replaced by a carboxylic acid derivative of formula (XXVI) in which $R^{17}$ is

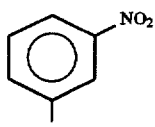

and $R^{18}$ is —CH$_2$CH$_3$.

Melting point (°C.) 115 (recrystallized from diethyl ether)
Yield (%) 74.6
IR (vKBr, cm$^{-1}$) 3304, 1746, 1682, 1530, 1348
Mass spectrometry Based on Formula $C_{23}H_{29}N_3O_7$
Calcd. 459.20051 Found 459.20109
NMR (δ, CDCl$_3$) 1.26 (3H, t, J=7), 1.44 (9H, s), 2.35 (3H s), 2.69 (2H, d, J=7), 3.67 (3H, s), 3.87 (2H d, J=5), 4.94 (1H s), 5.71 (1H s), 5.86 (1H, t, J=5 Hz), 7.43 (1H, dd, J=8 Hz, 8 Hz), 7.69 (1H, d, J=8 Hz), 8.04 (1H, d, J=8 Hz), 8.15 (1H, s)

EXAMPLE 76

Synthesis of t-butyl 2-[N-[1,4-dihydro-2-methyl-5-methoxycarbonyl-4-(3-nitrophenyl)-6-phenylpyridine-3-carbonyl]amino]acetate:

The above compound was synthesized in accordance with the following reaction scheme:

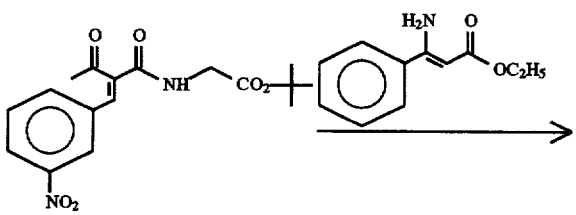

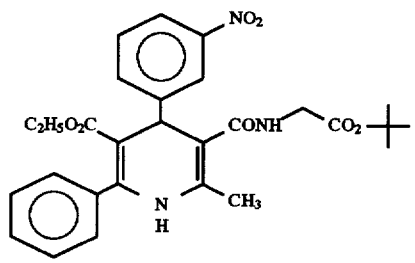

More specifically a mixture of 330 mg (1 mmol) of t-butyl 2-[N-[2-acetyl-3-(3-nitrophenyl)-2-propenoyl]-amino] acetate and 191 mg (1 mmol) of ethyl 3-amino-3-phenyl-2-propenoate was stirred under a light-shielding condition at 110° C. overnight. After cooling to room temperature, the reaction mixture was chromatographed on a silica gel column for purification, whereby 98 mg (22%) of the captioned compound was obtained as an oily material.

IR (vKBr, cm$^{-1}$) 3330, 1746, 1682, 1530, 1350

Mass spectrometry Based on Formula $C_{28}H_{31}N_3O_7$
Calcd. 521.21623 Found 521.21893

NMR (δ, CDCl$_3$) 0.84 (3H, d, J=7 Hz), 1.45 (9H, s), 2.33 (3H, s), 3.75–3.96 (2H, m), 3.90 (2H, d, J=5 Hz), 5.07 (1H, s), 5.85 (1H, s), 5.93 (1H, t, J=5 Hz), 7.26–7.32 (2H, m), 7.35–7.44 (3H, m), 7.48 (1H, dd, J=8 Hz, 8 Hz), 7.83 (1H, d, J=8 Hz), 8.08 (1H, d, J=8 Hz), 8.30 (1H, s)

Reference Example 9

Synthesis of (–)-methyl (R)-[N-[1-(t-butoxycarbonyl)-2-methylpropyl]]aminocrotonate:

The above compound was synthesized in accordance with the following reaction scheme:

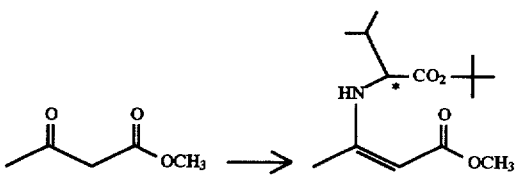

More specifically, 22.3 mg (0.4 mmol) of acetic acid was added to a mixture of 4.31 g (37.1 mol) of methyl acetoacetate and 6.75 g (39 mmol) of R-(–)-valine t-butyl ester, and the mixture was stirred for 24 hours. The reaction mixture was dissolved in 30 ml of anhydrous benzene. The thus obtained mixture was dried over anhydrous sodium sulfate and the benzene was distilled away under reduced pressure, whereby 10.07 g (100%) of the captioned compound was obtained.

NMR (δ, CDCl$_3$) 1.01 (6H, d, J=7 Hz) 1.47 (9H, s), 1.86 (3H, s), 2.09–2.23 (1H, m), 3.64 (3H, s), 3.78 (1H, dd, J=10 Hz, 6 Hz), 4.52 (1H, s), 8.87 (1H, d, J=10 Hz)

Optical rotation $[α]_D^{25}$=–132° [c=0.95, ethanol]

EXAMPLE 77

Synthesis of (–)-2-cyanoethyl methyl (R)-1,4-dihydro-2,6-dimethyl-4-(3-nitrophenyl)pyridine-3,5-dicarboxylate:

The above compound was synthesized in accordance with the following reaction scheme:

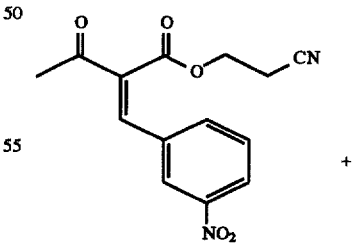

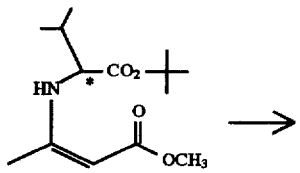

-continued

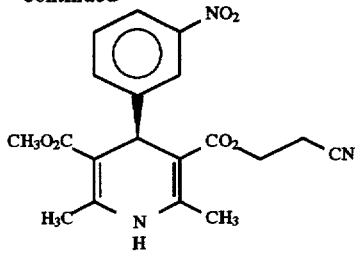

More specifically, a tetrahydrofuran solution containing phenylmagnesiumbromide in an amount of 1.2 equivalents was prepared by dissolving 1.30 g (53.4 mg atom) of magnesium, 0.84 g (4.5 mol) of 1,2-dibromethane and 6.99 g (44.5 mol) of bromobenzene in 23 ml of anhydrous tetrahydrofuran. In an atmosphere of argon gas, the tetrahydrofuran solution containing the phenylmagnesiumbromide was added dropwise to an anhydrous tetrahydrofuran solution containing 10.07 g (37.1 mol) of (–)-methyl (R)-[N-[1-(t-butoxycarbonyl)-2-methylpropyl]]-aminocrotonate at –15° C. and the reaction mixture was stirred for one hour. The reaction mixture was then cooled to –50° C. and an anhydrous tetrahydrofuran solution containing 10.18 g (35.3 mmol) of 2-cyanoethyl 2-(3-nitrobenzylidene)acetoacetate was added dropwise thereto. After the completion of the dropwise addition of the tetrahydrofuran solution, the reaction mixture was further stirred for 3 hours. To the reaction mixture, 51.2 ml of 2N hydrochloric acid was added dropwise and the temperature of the reaction mixture was raised to room temperature. An organic layer was separated from the reaction mixture and a water layer was extracted with tetrahydrofuran. The obtained organic layer and the extracted layer obtained by the tetrahydrofuran were combined and washed with a saturated aqueous solution of sodium chloride. To an organic layer obtained from the above mixture, 51.2 ml of 2N hydrochloric acid was added again and the mixture was stirred at room temperature for 3 hours. A saturated aqueous solution of sodium chloride was added to the mixture and an organic layer was separated from the mixture and further washed with a saturated aqueous solution of sodium chloride. An organic layer was separated from the mixture and dried over anhydrous sodium sulfate. The solvent in the organic layer was distilled away under reduced pressure. The residue was dissolved in 150 ml of methanol. With addition of 4.09 g (53 mmol) of ammonium acetate, the residue was stirred overnight and the solvent was distilled away under reduced pressure. The residue was then dissolved in methylene chloride, washed with a saturated aqueous solution of sodium hydrogencarbonate and with water, and dried over anhydrous sodium sulfate. The solvent was distilled away under reduced pressure. The residue was recrystallized from 100 ml of methanol, whereby 10.89 g (80%) of the captioned compound was obtained.

Melting point (°C.) 165.3°–166.6° C.

IR (cm$^{-1}$, KBr) 3390, 2250, 1706, 1682, 1526, 1354

Mass spectrometry Based on Formula $C_{19}H_{19}N_3O_6$ Calcd. 385.12736 Found 385.12672

NMR (δ, CDCl$_3$) 2.38 (3H, s), 2.40 (3H, s), 2.65 (2H, t, J=6 Hz), 3.65 (3H, s), 4.22 (1H, dd, J=13 Hz, 6 Hz), 4.31 (1H, dd, J=13 Hz, 6 Hz), 5.10 (1H, s), 5.77 (1H, s), 7.41 (1H, dd, J=8 Hz, 8 Hz), 7.67 (1H, d, J=8 Hz), 8.02 (1H, d, J=8 Hz), 8.10 (1H, s)

Optical rotation $[\alpha]_D^{25}$=–20.5° [c=1.038, methanol]

EXAMPLE 78

Synthesis of (+)-(S)-1,4-dihydro-2,6-dimethyl-5-methoxycarbonyl-4-(3-nitrophenyl)pyridine-3-carboxylic acid:

The above compound was synthesized in accordance with the following reaction scheme:

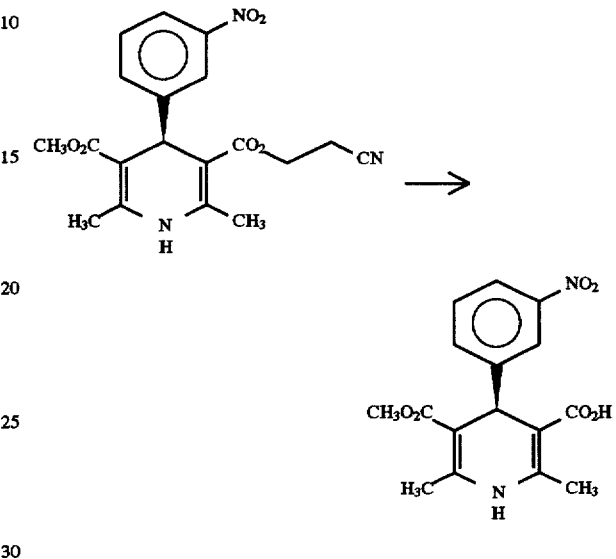

More specifically, under an ice-cooled condition, 10.89 g (28.3 mmol) of (–)-2-cyanoethyl methyl (R)-1,4-dihydro-2,6-dimethyl-4-(3-nitrophenyl)pyridine-3,5-dicarboxylate was suspended in 30 ml of anhydrous methanol. To the mixture, 5.73 g (29.7 mmol) of a 28% sodium methoxide was added. The mixture was stirred at room temperature for one hour and water was added thereto. The reaction mixture was then, washed with methylene chloride. With addition of 2N hydrochloric acid, the pH of the reaction mixture was adjusted to 3 to 4, and the reaction mixture was extracted with ethyl acetate. An organic layer was separated and washed with water and with a saturated aqueous solution of sodium chloride, and dried over anhydrous sodium sulfate. The solvent was distilled away under reduced pressure, whereby 9.34 g (100%) of the captioned compound was obtained.

Melting point (° C.) 171°–172° C. (dec.)

IR (cm$^{-1}$, KBr) 3360, 1678, 1534, 1352

Mass spectrometry Based on Formula $C_{16}H_{16}N_2O_6$ Calcd. 332.10081 Found 332.10107

NMR (δ, Acetone—d$_6$) 2.37 (6H, s), 3.61 (3H, s), 5.18 (1H, s), 7.52 (1H, t, J=8 Hz), 7.74 (1H, d, J=8 Hz), 8.01 (1H, d, J=8 Hz), 8.09 (1H, s), 8.15 (1H, s), 10.4 (1H, s)

Optical rotation $[\alpha]_D^{25}$=+19.3° [c=0.9924, acetone]

EXAMPLE 79

Synthesis of (+)-t-butyl (S)-[2-[N-[1,4-dihydro-2,6-dimethyl-5-methoxycarbonyl-4-(3-nitrophenyl)pyridin-3-yl]-carbonyl]amino]acetate:

The above compound was synthesized in accordance with the following reaction scheme:

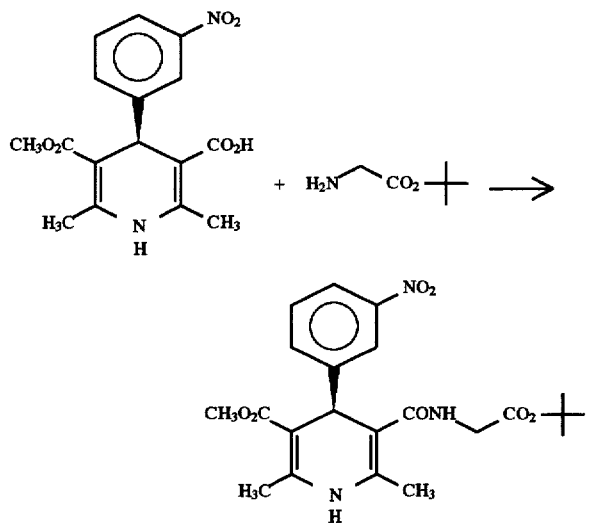

More specifically, under a light-shielding condition and in an atmosphere of an inert gas, a methylene chloride solution containing 1.91 g (11 mmol) of p-toluenesulfonyl chloride was added dropwise to an anhydrous methylene chloride solution containing 4.39 g (36 mmol) of N,N-dimethylaminopyridine. The reaction mixture was stirred for one hour under an ice-cooled condition. To the reaction mixture, 3.32 g (10 mmol) of (+)-(S)-1,4-dihydro-2,6-dimethyl-5-methoxycarbonyl-4-(3-nitrophenyl)-pyridine-3-carboxylic acid was added and the reaction mixture was stirred for one hour. To the reaction mixture, an anhydrous methylene chloride solution containing 1.57 g (12 mmol) of glycine-t-butylester was added dropwise and the reaction mixture was further stirred for one hour. The solvent was distilled away under reduce pressure. Toluene was added to the residue and insoluble components were removed from the mixture by filtration. The insoluble components were washed with toluene and the toluene employed for the washing was combined with the above filtrate.

The thus obtained toluene solution was washed with a saturated aqueous solution of ammonium chloride, with a dilute aqueous solution of sodium hydroxide and then with water, and dried over anhydrous sodium sulfate. The solvent was distilled away from the toluene solution under reduced pressure. The residue was chromatographed on a silica gel column for purification, whereby 4.00 g (90%) of the captioned compound with an optical rotation of $[\alpha]_D^{25}=+18.0°$ (c=1.0031, ethanol) was obtained.

The captioned compound with the following physical properties was obtained by recrystallization.

Melting point (°C.) 140.9°–142.4° C.

IR ($cm^{-1}$, KBr) ν=3328, 1742, 1682, 1532, 1352

Mass spectrometry Based on Formula $C_{22}H_{27}N_3O_7$ Calcd. 445.18484 Found 445.18726

NMR (δ, $CDCl_3$) 1.44 (9H, s), 2.31 (3H, s), 2.34 (3H, s), 3.66 (3H, s), 3.88 (2H, d, J=5 Hz), 4.96 (1H, s), 5.62 (1H, s), 5.86 (1H, t, J=5 Hz), 7.42 (1H, dd, J=8 Hz, 8 Hz), 7.69 (1H, d, J=8 Hz), 8.04 (1H, d, J=8 Hz), 8.13 (1H, s)

Optical rotation $[\alpha]_D^{25}+18.3°$ [c=1.0264, ethanol]

EXAMPLE 80

Synthesis of (+)-t-butyl (S)-[2-[N-[1,4-dihydro-2,6-dimethyl-5-methoxycarbonyl-4-(3-nitrophenyl)pyridin-3-yl]carbonyl]amino]acetate:

Under a light-shielding condition and in an atmosphere of an inert gas, 3.32 g (10 mmol) of (+)-(S)-1,4-dihydro-2,6-dimethyl-5-methoxycarbonyl-4-(3-nitrophenyl)pyridine-3-carboxylic acid was suspended in 33 ml of dried methylene chloride and the above mixture was cooled to −30° C. To the mixture, 2.29 g (11 mmol) of phosphorus pentachloride was added and the reaction mixture was stirred at 0° C. for one hour. The reaction mixture was cooled to −30° C. again and a dried methylene chloride solution containing 1.57 g (12 mmol) of glycine t-butylester and 2.42 g (24 mmol) of triethylamine was added to the mixture. After stirring at 0° C. for one hour, the reaction mixture was basified with addition of aqueous ammonia. An organic layer was separated from the above mixture and washed with water and dried over anhydrous sodium sulfate. The solvent was distilled away from the organic solution under reduced pressure. The residue was chromatographed on a silica gel column for purification and then recrystallized, whereby 4.23 g (95%) of the captioned compound was obtained. The thus obtained compound exhibited the same physical properties as those of the compound obtained in Example 79.

EXAMPLE 81

Synthesis of (+)-t-butyl (S)-[2-[N-[1,4-dihydro-2,6-dimethyl-5-methoxycarbonyl-4-(3-nitrophenyl)pyridin-3-yl]carbonyl]amino]acetate:

Under a light-shielding condition and in an atmosphere of an inert gas, 3.32 g (10 mmol) of (+)-(S)-1,4-dihydro-2,6-dimethyl-5-methoxycarbonyl-4-(3-nitrophenyl)pyridine-3-carboxylic acid, 3.09 g (15 mmol) of dicyclohexylcarbodiimide and 4.39 g (36 mmol) of N,N-dimethylaminopyridine were dissolved in 33 ml of dried methylene chloride and the mixture was stirred for one hour. To the above mixture, 1.57 g (12 mmol) of glycine t-butylester was added and the mixture was stirred for 2 days. The insoluble components were removed from the mixture by filtration. The solvent was distilled away from the mixture under reduced pressure. The residue was chromatographed on a silica gel column for purification and then recrystallized, whereby 4.14 g (93%) of the captioned compound was obtained. This obtained compound exhibited the same physical properties as those of the compound obtained in Example 79.

EXAMPLE 82

Synthesis of t-butyl 2-(R)-[N-[1,4-dihydro-2,6-dimethyl-5-methoxycarbonyl-4-(S)-(3-nitrophenyl]pyridine-3-carbonyl]-amino]-3-methylbutytate:

The above compound was synthesized in accordance with the following reaction scheme:

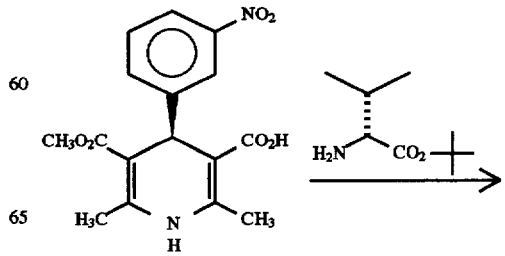

71
-continued

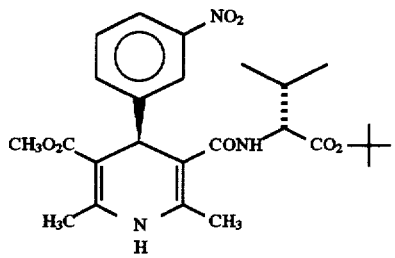

More specifically, 354 mg (1.07 mmol) of (S)-(+)-1,4-dihydro-2,6-dimethyl-5-methoxycarbonyl-4-(3-nitrophenyl)pyridine-3-carboxylic acid was suspended in 10 ml of dichloromethane. To the above mixture, 330 mg (1.6 mmol) of 1,3-dicyclohexylcarbodiimide and 161 mg (1.3 mmol) of 4-dimethylaminopyridine were added, and the reaction mixture was stirred for one hour. Subsequently, a dichloromethane solution containing 191 mg (1.1 mmol) of D-valine-t-butylester was added to the reaction mixture and the reaction mixture was stirred at room temperature for 2 days. The reaction mixture was washed with water and then dried over anhydrous sodium sulfate. The dichloromethane was distilled away from the reaction mixture under reduced pressure. The thus obtained mixture was chromatographed on a silica gel column for purification and then recrystallized from methanol, whereby 340 mg (69.5%) of the captioned compound was obtained. This compound exhibited the same physical properties as those of Compound b obtained in Example 2.

EXAMPLE 83

Synthesis of (+)-t-butyl 2-(S)-[N-[1,4-dihydro-2,6-dimethyl-5-methoxycarbonyl-4-(S)-(3-nitrophenyl)pyridine-3-carbonyl]amino]propionate:

The above compound was synthesized in accordance with the same reaction scheme as in Example 82 except that the amine compound employed in Example 82.was replaced by an amine compound shown below. Specifically the reaction scheme in this example is as follows:

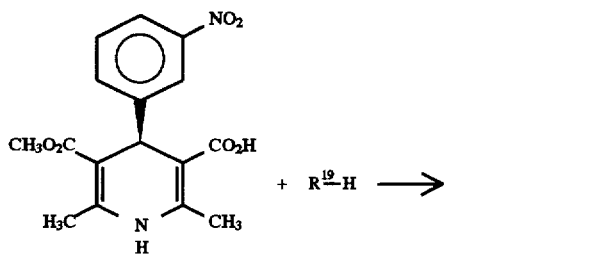

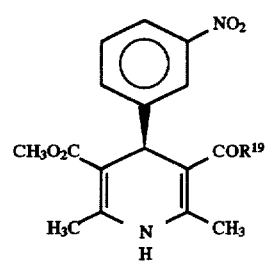

72 wherein $R^{19}$ is

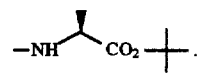

Yield (%) 88.2
IR (vKBr, cm$^{-1}$) 3330, 1740, 1680, 1530, 1350
Mass spectrometry Based on Formula $C_{23}H_{29}N_3O_7$ Calcd. 459.20051 Found 459.20035
NMR (δ, CDCl$_3$) 1.27 (3H, d, J=7 Hz), 1.41 (9H, s), 2.26 (3H, s), 2.36 (3H, s), 3.64 (3H, s), 4.40 (1H, dq, J=7 Hz, 7 Hz), 4.97 (1H, s), 5.55 (1H, s), 5.97 (1H, d, J=7 Hz), 7.41 (1H, dd, J=8 Hz, 8 Hz), 7.67 (1H, d, J=8 Hz), 8.03 (1H, d, J=8 Hz), 8.13 (1H, s)
Optical rotation $[\alpha]_D^{25}$=+71.01° [c=0.9444, ethyl alcohol]

EXAMPLE 84

Synthesis of (+)-t-butyl 2-(S)-[N-[1,4-dihydro-2,6-dimethyl-5-methoxycarbonyl-4-(S)-(3-nitrophenyl)pyridine-3-carbonyl]amino]-3-phenylpropionate:

The above compound was prepared in the same reaction scheme as in Example 83 except that the amine compound of formula $R^{19}$-H employed in Example 83 was replaced by an amine compound of $R^{19}$-H in which $R^{19}$ is

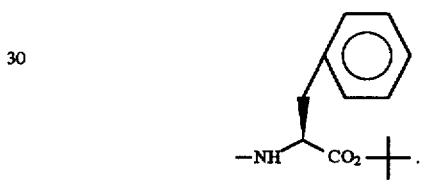

Yield (%) 98.1
Melting point (°C.) 200–203
IR (vKBr, cm$^{-1}$) 3328, 1746, 1700, 1678, 1532, 1348
Mass spectrometry Based on Formula $C_{29}H_{33}N_3O_7$ Calcd. 535.23181 Found 535.23243
NMR (δ, CDCl$_3$) 1.35 (9H, s), 2.19 (3H, s), 2.33 (3H, s), 2.97 (1H, dd, J=15 Hz, 6 Hz), 3.06 (1H, dd, J=15 Hz, 6 Hz), 3.63 (3H, s), 4.68–4.76 (1H, m), 4.89 (1H, s), 5.62 (1H, s), 5.73 (1H, d, J=7 Hz), 6.90–6.98 (2H, m), 7.18–7.26 (3H, m), 7.36 (1H, dd, J=8 Hz, 8 Hz), 7.52 (1H, d, J=8 Hz), 8.02 (1H, d, J=8 Hz), 8.03 (1H, s)
Optical rotation $[\alpha]_D^{25}$=+33.35° [c=0.993, ethyl alcohol]

EXAMPLE 85

Synthesis of (+)-t-butyl 2-(S)-[N-[1,4-dihydro-2,6-dimethyl-5-methoxycarbonyl-4-(S)-(3-nitrophenyl)pyridine-3-carbonyl]amino]-4-methylpentanoate:

The above compound was synthesized in the same reaction scheme as in Example 83 except that the amine compound of formula $R^{19}$-H employed in Example 83 was replaced by an amine compound of $R^{19}$-H in which $R^{19}$ is

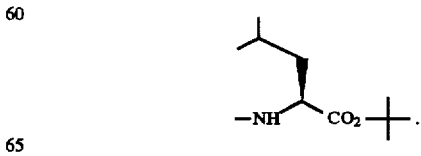

Yield (%) 99.2

IR (vKBr, cm$^{-1}$) 3320, 1740, 1690, 1530, 1350

Mass spectrometry Based on Formula $C_{26}H_{35}N_3O_7$ Calcd. 501.24746 Found 501.24722

NMR (δ, CDCl$_3$) 1.16–1.62 (3H, m), 1.40 (9H, s), 2.23 (3H, s), 2.35 (3H, s), 3.61 (3H, s), 4.48 (1H, dt, J=8 Hz, 5 Hz), 5.01 (1H, s), 5.48 (1H, s), 5.61 (1H, d, J=8 Hz), 7.40 (1H, dd, J=8 Hz, 8 Hz), 7.65 (1H, d, J=8 Hz), 8.03 (1H, d, J=8 Hz), 8.12 (1H, s)

Optical rotation $[\alpha]_D^{25}$=+90.65° [c=0.9869, ethyl alcohol]

EXAMPLE 86

Synthesis of (+)-t-butyl-(S)-[N-[1,4-dihydro-2,6-dimethyl-5-methoxycarbonyl-4-(S)-(3-nitrophenyl) pyridine-3-carbonyl]amino]-4-(t-butoxycarbonyl)butylate:

The above compound was synthesized in the same reaction scheme as in Example 83 except that the amine compound of formula R$^{19}$-H employed in Example 83 was replaced by an amine compound of formula R$^{19}$-H in which R$^{19}$ is

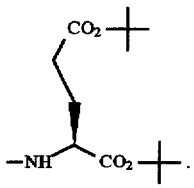

Yield (%) 97.8

IR (vKBr, cm$^{-1}$) 3330, 1730, 1710, 1680, 1530, 1350

Mass spectrometry Based on Formula $C_{29}H_{39}N_3O_9$ Calcd. 573.26858 Found 573.26850

NMR (δ, CDCl$_3$) 1.40 (9H, s), 1.43 (9H, s), 1.73–2.15 (4H, m), 2.26 (3H, s), 2.36 (3H, s), 3.63 (3H, s), 4.45 (1H, dt, J=7 Hz, 4 Hz) 5.00 (1H, s), 5.51 (1H, s), 6.09 (1H, d, J=7 Hz), 7.41 (1H, dd, J=8 Hz, 8 Hz), 7.67 (1H, d, J=8 Hz), 8.02 (1H, d, J=8 Hz), 8.14 (1H, S)

Optical rotation $[\alpha]_D^{25}$=+73.76° [c=1.0150, ethyl alcohol]

EXAMPLE 87

Synthesis of (+)-t-butyl 1-[1,4-dihydro-2,6-dimethyl-5-methoxycarbonyl-4-(S)-(3-nitrophenyl)pyridine-3-carbonyl]-pyrrolidine-2-(S)-carboxylate:

The above compound was synthesized in the same reaction scheme as in Example 83 except that the amine compound of formula R$^{19}$-H employed in Example 83 was replaced by an amine compound of formula R$^{19}$-H in which R$^{19}$ is

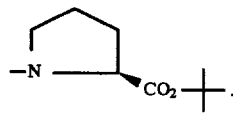

Yield (%) 86.0

IR (vKBr, cm$^{-1}$) 3320, 1740, 1700, 1532, 1350

Mass spectrometry Based on Formula $C_{25}H_{31}N_3O_7$ Calcd. 485.21616 Found 485.21630

NMR (δ, CDCl$_3$) 1.45 (9H, s), 1.63–1.84 (3H, m), 1.97 (3H, s) 2.05–2.18 (1H, m), 2.41 (3H, s), 2.62–2.70 (1H, m), 3.15–3.27 (1H, m), 3.51 (3H, s), 4.32 (1H, t, J=8 Hz), 5.08 (1H, s), 5.37 (1H, s), 7.39 (1H, dd, J=8 Hz, 8 Hz), 7.55 (1H, d, J=8 Hz), 8.01 (1H, d, J=8 Hz), 8.07 (1H, s)

Optical rotation $[\alpha]_D^{25}$=+10.15° [c=1.0076, ethyl alcohol]

Reference Example 10

Synthesis of (+)-methyl (S)-[N-[1-(t-butoxycarbonyl)-2-methylpropyl]]aminocrotonate:

The above compound was synthesized in accordance with the following reaction scheme:

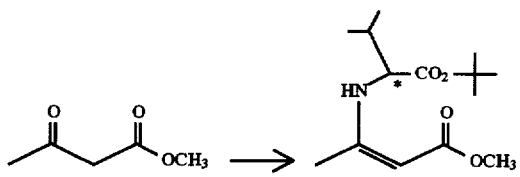

More Specifically, 22.3 mg (0.4 mmol) of acetic acid was added to a mixture of 4.31 g (37.1 mol) of methyl acetoacetate and 6.75 g (39 mmol) of 1-valine t-butyl ester, and the obtained mixture was stirred for 24 hours. The reaction mixture was dissolved in 30 ml of anhydrous benzene and dried over anhydrous sodium sulfate. The benzene was distilled away from the reaction mixture under reduced pressure, whereby 10.07 g (100%) of the captioned compound was obtained.

NMR (δ, CDCl$_3$) 1.01 (6H, d, J=7 Hz), 1.47 (9H, s), 1.86 (3H, s), 2.09–2.23 (1H, m), 3.64 (3H, s), 3.78 (1H, dd, J=10 Hz, 6 Hz), 4.52 (1H, s), 8.87 (1H, d, J=10 Hz)

Optical rotation $[\alpha]_D^{25}$=+132° [c=1.01, ethanol]

EXAMPLE 88

Synthesis of (+)-2-cyanoethyl methyl (S)-1,4-dihydro-2,6-dimethyl-4-(3-nitrophenyl)pyridine-3,5-dicarboxylate:

The above compound was synthesized in accordance with the following reaction scheme:

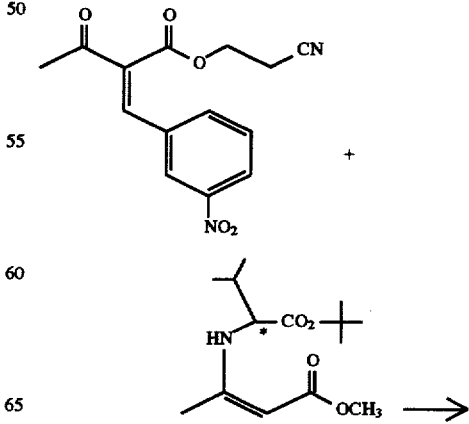

-continued

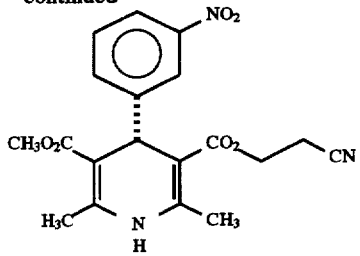

More specifically, a tetrahydrofuran solution containing phenylmagnesiumbromide in an amount of 1.2 equivalents was prepared by dissolving 1.30 g (53.4 mg atom) of magnesium, 0.84 g (4.5 mol) of 1,2-dibromoethane and 6.99 g (44.5 mol) of bromobenzene in 23 ml of anhydrous tetrahydrofuran. In an atmosphere of argon gas, the tetrahydrofuran solution containing the phenylmagnesium-bromide was added dropwise to an anhydrous tetrahydrofuran solution containing 10.07 g (37.1 mol) of (+)-methyl (S)-[N-[1-(t-butoxycarbonyl)-2-methylpropyl]]aminocrotonate at $-15°$ C. and the reaction mixture was stirred for one hour. The reaction mixture was cooled to $-50°$ C. and an anhydrous tetrahydrofuran solution containing 10.18 g (35.3 mmol) of 2-cyanoethyl 2-(3-nitrobenzylidene)acetoacetate was added dropwise to the above reaction mixture. After the completion of the dropwise addition of the tetrahydrofuran solution, the reaction mixture was further stirred for 3 hours.

To the reaction mixture, 51.2 ml of 2N hydrochloric acid was added dropwise and the temperature of the reaction mixture was raised to room temperature. An organic layer was separated from the reaction mixture and a water layer was extracted with tetrahydrofuran. The obtained organic layer and the extracted layer obtained by the tetrahydrofuran were combined and washed with a saturated aqueous solution of sodium chloride. To an organic layer obtained from the above mixture, 51.2 ml of 2N hydrochloric acid was added again and the mixture was stirred at room temperature for 3 hours. A saturated aqueous solution of sodium chloride was added to the mixture and an organic layer was separated from the mixture and further washed with a saturated aqueous solution of sodium chloride. An organic layer was separated from the mixture and dried over anhydrous sodium sulfate. The solvent in the organic layer was distilled away under reduced pressure. The residue was dissolved in 150 ml of methanol. With addition of 4.09 g (53 mmol) of ammonium acetate, the residue was stirred overnight and the solvent was distilled away under reduced pressure. The residue was then dissolved in methylene chloride, washed with a saturated aqueous solution of sodium hydrogencarbonate and then with water, and dried over anhydrous sodium sulfate. The solvent was distilled away under reduced pressure. The residue was recrystallized from 100 ml of methanol, whereby 10.89 g (80%) of the captioned compound was obtained.

Melting point (°C.) 165.3°–166.6° C.

IR (cm$^{-1}$, KBr) 3388, 2250, 1706, 1682, 1526, 1354

Mass spectrometry $C_{19}H_{19}N_3O_6$ Calcd. 385.12736 Found 385.12672

NMR (δ, CDCl$_3$) 2.38 (3H, s), 2.40 (3H, s), 2.65 (2H, t, J=6 Hz), 3.65 (3H, s), 4.22 (1H, dd, J=13 Hz, 6 Hz), 4.31 (1H, dd, J=13 Hz, 6 Hz), 5.10 (1H, s), 5.77 (1H, s), 7.41 (1H, t, J=8 Hz), 7.67 (1H, d, J=8 Hz), 8.02 (1H, d, J=8 Hz), 8.10 (1H,s)

Optical rotation $[\alpha]_D^{25}$=+20.5° [c=1.005, methanol]

EXAMPLE 89

Synthesis of (−)-(R)-1,4-dihydro-2,6-dimethyl-5-methoxycarbonyl-4-(3-nitrophenyl)pyridine-3-carboxylic acid:

The above compound was synthesized in accordance with the following reaction scheme:

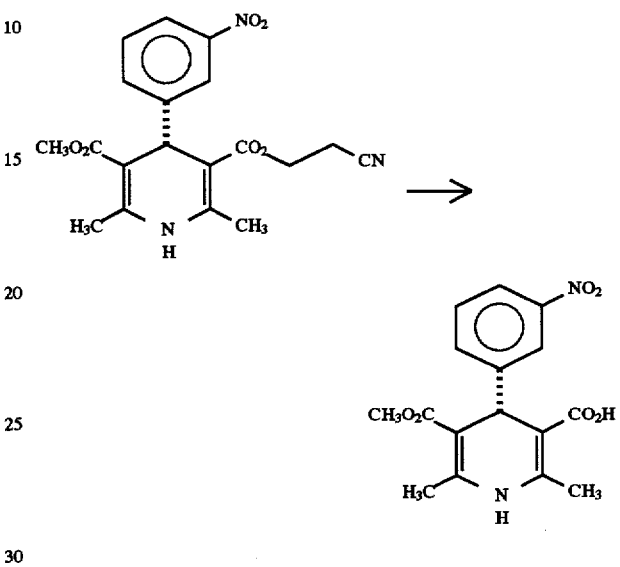

More specifically, under an ice-cooled condition, 10.89 g (28.3 mmol) of (+)-2-cyanoethyl methyl (S)-1,4-dihydro-2,6-dimethyl-4-(3-nitrophenyl)pyridine-3,5-dicarboxylate was suspended in 30 ml of anhydrous methanol. To the above mixture, 5.73 g (29.7 mmol) of a 28% sodium methoxide was added. The reaction mixture was stirred at room temperature for one hour and water was added thereto. The reaction mixture was then washed with methylene chloride. With addition of 2N hydrochloric acid, the PH of the reaction mixture was adjusted to 3 to 4, and the reaction mixture was extracted with ethyl acetate. An organic layer was separated and washed with water and then with a saturated aqueous solution of sodium chloride, and dried over anhydrous sodium sulfate. The solvent was distilled away under reduced pressure, whereby 9.34 g (100%) of the captioned compound was obtained.

Melting point (°C.) 171°–172° C. (dec.)

IR (cm$^{-1}$, KBr) 3360, 1678, 1534, 1352

Mass spectrometry $C_{16}H_{16}N_2O_6$ Calcd. 332.10081 Found 332.10107

NMR (δ, Acetone—d$_6$) 2.37 (6H, s), 3.61 (3H, s), 5.18 (1H, s), 7.52 (1H, t, J=8 Hz), 7.74 (1H, d, J=8 Hz), 8.01 (1H, d, J=8 Hz), 8.09 (1H, s), 8.15 (1H, s), 10.4 (1H, s).

Optical rotation $[\alpha]_D^{25}$=−19.3° [c=1.021, acetone]

EXAMPLE 90

Synthesis of (−)-t-butyl (R)-[2-[N-[1,4-dihydro-2,6-dimethyl-5-methoxycarbonyl-4-(3-nitrophenyl)pyridine-3-yl]carbonyl]amino]acetate:

The above compound was synthesized in accordance with the following reaction scheme:

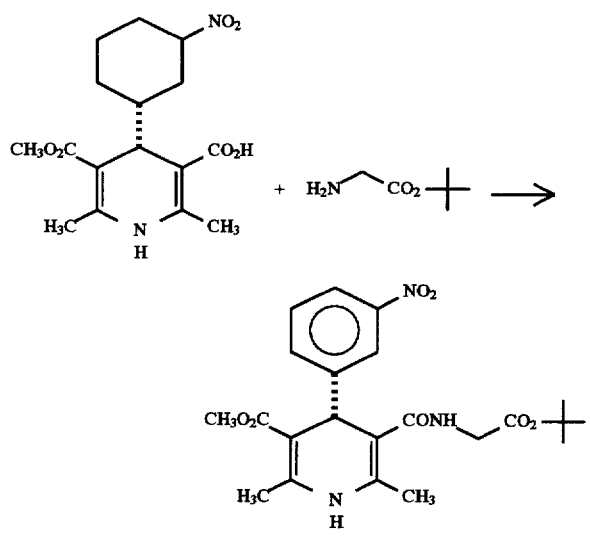

More specifically, under a light-shielding condition and in an atmosphere of an inert gas, a methylene chloride solution containing 1.91 g (11 mmol) of p-toluenesulfonylchloride was added dropwise to an anhydrous methylene chloride solution containing 4.39 g (36 mmol) of N,N-dimethylaminopyridine under an ice-cooled condition. The above reaction mixture was stirred for one hour. To the reaction mixture, 3.32 g (10 mmol) of (−)-(R)-1,4-dihydro-2,6-dimethyl-5-methoxycarbonyl-4-(3-nitrophenyl)pyridine-3-carboxylic acid was added and the reaction mixture was stirred for one hour. To the mixture, an anhydrous methylene chloride solution containing 1.57 g (12 mmol) of glycine-t-butylester was added dropwise and the reaction mixture was further stirred for one hour. The solvent was distilled away from the reaction mixture under reduced pressure and toluene was added to the obtained residue. Insoluble components were removed from the mixture by filtration. The insoluble components were washed with toluene and the toluene employed for the washing was combined with the above filtrate. The mixture was successively washed with a saturated aqueous solution of ammonium chloride, with a dilute aqueous solution of sodium hydroxide and water, and dried over anhydrous sodium sulfate. The solvent was distilled away under reduced pressure. The thus obtained residue was chromatographed on a silica gel column for purification, whereby 3.96 g (89%) of the captioned compound with an optical rotation of $[\alpha]_D^{25}$= −18.1° (c=1.102, ethanol) was obtained. The captioned compound with the following physical properties was obtained by recrystallization.

Melting point (°C.) 140.0°–141.8° C.

IR (cm$^{-1}$, KBr) ν=3328, 1742, 1682, 1532, 1352

Mass spectrometry Based on Formula $C_{22}H_{27}N_3O_7$ Calcd. 445.18484 Found 445.18655

NMR (δ, CDCl$_3$) 1.44 (9H, s), 2.31 (3H, s), 2.34 (3H, s), 3.66 (3H, s), 3.88 (2H, d, J=5 Hz), 4.96 (1H, s), 5.62 (1H, s), 5.86 (1H, t, J=5 Hz), 7.42 (1H, dd, J=8 Hz, 8 Hz), 7.69 (1H, d, J=8 Hz), 8.04 (1H, d, J=8 Hz), 8.13 (1H, s)

Optical rotation $[\alpha]_D^{25}$=−18.4° [c=1.053, ethanol]

EXAMPLE 91

Synthesis of (−)-t-butyl 2-(S)-[N-[1,4-dihydro-2,6-dimethyl-5-methoxycarbonyl-4-(R)-(3-nitrophenyl)pyridine-3-carbonyl]amino]propionate:

The above compound was synthesized in accordance with the same reaction scheme as in Example 90 except that the amine compound employed in Example 90 was replaced by an amine compound shown below. Specifically the reaction scheme in this example is as follows:

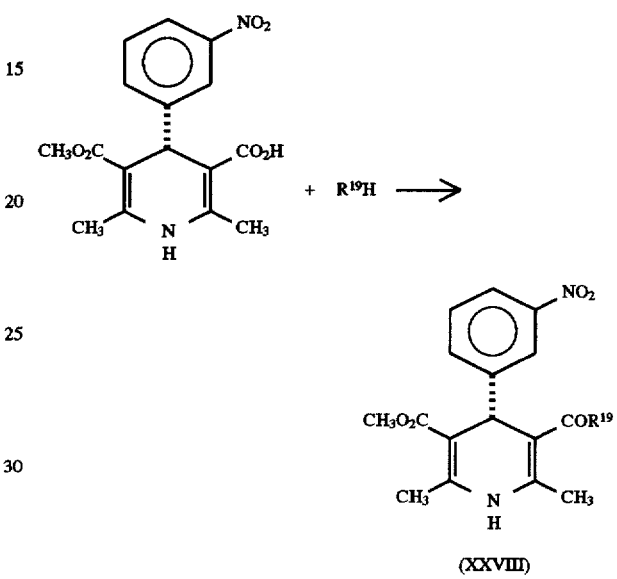

wherein R$^{19}$ is

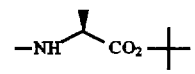

Yield (%) 90.8

IR (cm$^{-1}$, νKBr) 3320, 1740 1680, 1530 1350

Mass spectrometry Based on Formula $C_{23}H_{29}N_3O_7$ Calcd. 459.20051 Found 459.20040

NMR (δ, CDCl$_3$) 1.26 (3H, d, J=7 Hz), 1.45 (9H, s), 2.26 (3H, s), 2.35 (3H, s), 3.65 (3H, s), 4.42 (1H, dq, J=7 Hz, 4 Hz), 4.93 (1H, s), 5.58 (1H, s), 5.99 (1H, d, J=7 Hz), 7.42 (1H, dd, J=8 Hz, 8 Hz), 7.67 (1H, d, J=8 Hz), 8.03 (1H, d, J=8 Hz), 8.12 (1H, s)

Optical rotation $[\alpha]_D^{25}$=−31.24° [c=1.0188, ethyl alcohol]

EXAMPLE 92

Synthesis of (−)-t-butyl 2-(S)-[N-[1,4-dihydro-2,6-dimethyl-5-methoxycarbonyl-4-(R)-(3-nitrophenyl)pyridine-3-carbonyl]amino]-3-phenylpropionate:

The above compound was synthesized in the same reaction scheme as in Example 91 except that the amine compound of formula (XXVIII) employed in Example 91 was replaced by an amine compound of formula (XXVIII) in which R$^{19}$ is

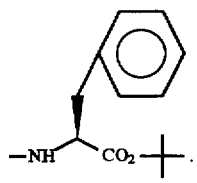

Yield (%) 100

IR (cm$^{-1}$, KBr) 3330, 1740 1690 1530, 1350

Mass spectrometry Based on Formula $C_{29}H_{33}N_3O_7$ Calcd. 535.23181 Found 535.23190

NMR (δ, CDCl$_3$) 1.41 (9H, s), 2.23 (3H, s), 2.31 (3H, s), 2.95 (1H, dd, J=15 Hz, 6 Hz), 3.03 (1H, dd, J=15 Hz, 6 Hz), 3.65 (3H, s), 4.72 (1H, dt, J=8 Hz, 6 Hz), 4.87 (1H, s), 5.63 (1H, s), 5.79 (1H, d, J=8 Hz), 6.86–6.92 (2H, m), 7.06–7.14 (3H, m) 7.35 (1H, dd, J=8 Hz, 8 Hz), 7.56 (1H, d, J=8 Hz), 8.01 (1H, d, J=8 Hz), 8.05 (1H, s)

Optical rotation $[\alpha]_D^{25}$=–23.61° [c=1.0035, ethyl alcohol]

EXAMPLE 93

Synthesis of (–)-t-butyl 2-(S)-[N-[1,4-dihydro-2,6-dimethyl-5-methoxycarbonyl-4-(R)-(3-nitrophenyl)pyridine-3-carbonyl]amino]-4-methylpentanoate:

The above compound was synthesized in the same reaction scheme as in Example 91 except that the amine compound of formula (XXVIII) employed in Example 91 was replaced by an amine compound of formula (XXVIII) in which R$^{19}$ is

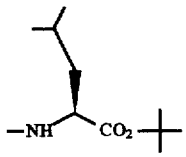

Yield (%) 99.8

IR (vcm$^{-1}$, KBr) 3330, 1740, 1690, 1630, 1540, 1350

Mass spectrometry Based on Formula $C_{26}H_{35}N_3O_7$ Calcd. 501.24746 Found 501.24752

NMR (δ, CDCl$_3$) 0.77 (3H, d, J=6 Hz), 0.79 (3H, d, J=6 Hz), 1.20–1.57 (3H, m), 1.44 (9H, s), 2.28 (3H, s), 2.34 (3H, s), 3.66 (3H, s), 4.46 (1H, dt, J=8 Hz, 6 Hz), 4.94 (1H, s), 5.65 (1H, s), 5.77 (1H, d, J=8 Hz), 7.42 (1H, dd, J=8 Hz, 8 Hz), 7.67 (1H, d, J=8 Hz), 8.04 (1H, d, J=8 Hz), 8.13 (1H, s)

Optical rotation $[\alpha]_D^{25}$=–24.65° [c=0.9926, ethyl]

EXAMPLE 94

Synthesis of (–)-t-butyl 2-(S)-[N-[1,4-dihydro-2,6-dimethyl-5-methoxycarbonyl-4-(R)-(3-nitrophenyl)pyridine-3-carbonyl]amino]-4-(t-butoxycarbonyl)butylate:

The above compound was synthesized in the same reaction scheme as in Example 91 except that the amine compound of formula (XXVIII) employed in Example 91 was replaced by an amine compound of formula (XXVIII) in which R$^{19}$ is

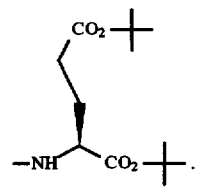

Yield (%) 65.3

IR (vcm$^{-1}$, KBr) 3320, 1730, 1710, 1680, 1530, 1350

Mass spectrometry Based on Formula $C_{29}H_{39}N_3O_9$ Calcd. 573.26858 Found 573.26863

NMR (δ, CDCl$_3$) 1.40 (9H, s), 1.45 (9H, s), 1.70–2.23 (4H, m), 2.30 (3H, s), 2.34 (3H, s), 3.65 (3H, s), 4.46 (1H, dt, J=7 Hz, 4 Hz), 4.94 (1H, s), 5.65 (1H, s), 6.17 (1H, d, J=7 Hz), 7.42 (1H, dd, J=8 Hz, 8 Hz), 7.69 (1H, d, J=8 Hz), 8.03 (1H, d, J=8 Hz), 8.15 (1H, S)

Optical rotation $[\alpha]_D^{25}$=–15.01° [c=0.8836, ethyl alcohol]

EXAMPLE 95

Synthesis of (–)-t-butyl 1-[1,4-dihydro-2,6-dimethyl-5-methoxycarbonyl-4-(R)-(3-nitrophenyl)pyridine-3-carbonyl]-pyrrolidine-2-(S)-carboxylate:

The above compound was synthesized in the same reaction scheme as in Example 91 except that the amine compound of formula (XXVIII) employed in Example 91 was replaced by an amine compound of formula (XXVIII) in which R$^{19}$ is

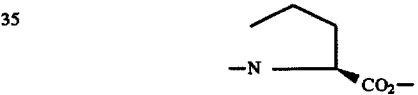

Yield (%) 89.5

IR (vcm$^{-1}$, KBr) 3270, 1740, 1694, 1530, 1350

Mass spectrometry Based on Formula $C_{25}H_{31}N_3O_7$ Calcd. 485.21616 Found 485.21590

NMR (δ, CDCl$_3$) 1.44 (9H, s), 1.75–2.00 (3H, m), 1.97 (3H, s), 2.12–2.26 (1H, m), 2.38 (3H, s), 3.16–3.27 (1H, m), 3.43–3.60 (1H, m), 3.60 (3H, s), 4.31 (1H, dd, J=8 Hz, 3 Hz), 4.79 (1H, s), 5.54 (1H, s), 7.40 (1H, dd, J=8 Hz, 8 Hz), 7.63 (1H, d, J=8 Hz), 8.01 (1H, d, J=8 Hz), 8.07 (1H, s,)

Optical rotation $[\alpha]_D^{25}$=–39.09° [c=1.0060, ethyl alcohol]

Reference Example 11

Synthesis of t-butyl 2-[N-(3-oxobutanoyl)amino]acetate:

3.93 g (50 mmol) of t-butyl 2-aminoacetate was dissolved in 65 ml of benzene. To the above mixture, 4.41 g (52.5 mmol) of diketene was added dropwise and the reaction mixture was stirred for one hour. The reaction mixture was washed with a saturated aqueous solution of sodium hydrogencarbonate and then with water, and dried over anhydrous sodium sulfate. The solvent was distilled away from the reaction mixture under reduced pressure, whereby 9.821 g (91.2%) of the captioned compound was obtained.

NMR (δ, CDCl$_3$) 1.47 (9H, s), 2.28 (3H, s), 3.46 (2H, s), 3.96 (2H, d, J=5 Hz), 7.33 (1H, s)

Reference Example 12

Synthesis of t-butyl 2-[N-[2-(3-nitrobenzylidene)-3-oxobutanoyl]amino]acetate:

9.821 g (45.6 mmol) of t-butyl 2-[N-(3-oxobutanoyl) amino]acetate and 6.891 g (45.6 mmol) of 3-nitrobenzaldehyde were suspended in 50 ml of isopropyl alcohol. With addition of 0.331 g (2.28 mmol) of piperidine acetate, the mixture was stirred for 15 hours. The above mixture was ice-cooled for one hour and the precipitated crystals were separated by filtration. The thus obtained crystals were washed with cooled isopropyl alcohol and dried under reduced pressure. The thus obtained crystals were recrystallized from acetonitrile, whereby 13.5 g (85%) of the captioned compound was obtained.

Melting point (°C.) 104.8–106.0

NMR (δ, CDCl$_3$) 1.46 (9H, s), 2.50 (3H, s), 4.08 (2H, d, J=5 Hz), 6.47 (1H, d, J=5 Hz), 7.58 (1H, t, J=8 Hz), 7.60 (1H, s), 7.90 (1H, d, J=8 Hz), 8.24 (1H, d, J=8 Hz), 8.38 (1H, s)

Reference Example 13

Synthesis of (−)-methyl (R)-[N-[1-(t-butoxycarbonyl)-2-methypropyl]]aminocrotonate:

0.018 g (0.3 mol) of acetic acid was added to a mixture of 3.484 g (30 mmol) of methyl acetoacetate and 5.458 g (31.5 mmol) of D-valine t-butyl ester. The above mixture was then stirred for 24 hours and dissolved in 45 ml of benzene. The reaction mixture was washed with water and dried over anhydrous sodium sulfate. The solvent was distilled away from the reaction mixture under reduced pressure, whereby 8.14 g (100%) of the captioned compound was obtained.

Optical rotation [α]=−132° [c=0.95, ethanol]

NMR (δ, CDCl$_3$) 1.01 (6H, d, J=7 Hz), 1.47 (9H, s), 1.86 (3H, s), 2.09–2.23 (1H, m), 3.64 (3H, s), 3.78 (1H, dd, J=10 Hz, 6 Hz), 4.52 (1H, s), 8.87 (1H, d, J=10 Hz)

Reference Example 14

Synthesis of (+)-methyl (S)-[N-[1-(t-butoxycarbonyl)-2-methylpropyl]]aminocrotonate:

0.018 g (0.3 mol) of acetic acid was added to a mixture of 3.484 g (30 mmol) of methyl acetoacetate and 5.458 g (31.5 mmol) of L-valine t-butyl ester. The mixture was then stirred for 24 hours and dissolved in 45 ml of benzene. The reaction mixture was washed and dried over anhydrous sodium sulfate. The solvent was distilled away from the reaction mixture under reduced pressure, whereby 8.14 g (100%) of the captioned compound was obtained.

Optical rotation [α]$_D^{25}$=+131° [c=1.02, ethanol].

NMR (δ, CDCl$_3$) 1.01 (6H, d, J=7 Hz), 1.47 (9H, s), 1.86 (3H, s), 2.09–2.23 (1H, m), 3.64 (3H, s), 3.78 (1H, dd, J=10 Hz, 6 Hz), 4.52 (1H, s), 8.87 (1H, d, J=10 Hz)

EXAMPLE 96

Snythesis of (+)-t-butyl (S)-[2-[N-[1,4-dihydro-2,6-dimethyl-5-methoxycarbonyl-4-(3-nitrophenyl)pyridine-3-yl]carbonyl]amino]acetate:

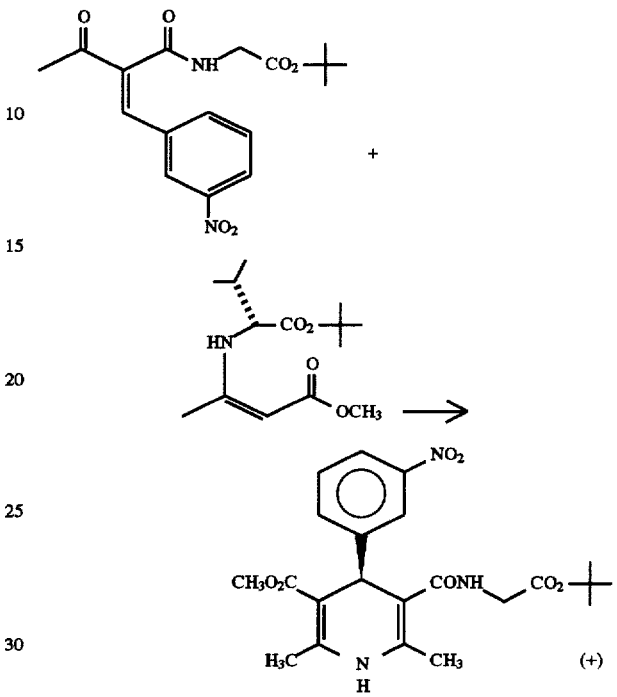

More specifically, a tetrahydrofuran solution containing phenylmagnesiumbromide in an amount of 1.2 equivalents was prepared by dissolving 0.153 g (6.3 g atom) of magnesium, 0.075 g (0.4 mmol) of 1,2-dibromoethane and 0.832 g (5.3 mol) of bromobenzene in 20 ml of anhydrous tetrahydrofuran. In an atmosphere of argon gas, a tetrahydrofuran solution containing the phenylmagnesiumbromide was added dropwise to 12 ml of an anhydrous tetrahydrofuran solution containing 1.194 g (4.4 mmol) of (−)-methyl (R)-[N-[1-(t-butoxycarbonyl)-2-methylpropyl]] aminocrotonate at −15° C. and the mixture was further stirred for one hour. The reaction mixture was cooled to −70° C. and an anhydrous tetrahydrofuran solution containing 1.359 g (3.9 mmol) of t-butyl 2-[N-[2-(3-nitrobenzylidene)-3-oxobutanoyl]amino]acetate was added dropwise thereto. After the completion of the dropwise addition of the tetrahydrofuran solution, the reaction mixture was further stirred for 3 hours. To the obtained reaction mixture, 11 ml of 1N hydrochloric acid was added dropwise and the temperature of the reaction mixture was raised to room temperature. An organic layer was separated from the reaction mixture. A water layer was extracted with tetrahydrofuran. The extracted layer by the tetrahydrofuran was combined with the organic layer, washed with a saturated aqueous solution of sodium chloride and dried over anhydrous sodium sulfate. The solvent was distilled away from the mixture under reduced pressure. The residue was dissolved in 20 ml of methanol and 3.39 g (44 mmol) of ammonium acetate was added thereto. The mixture was then stirred at room temperature overnight. The solvent was distilled away from the mixture under reduced pressure. The residue was dissolved in methylene chloride, washed with a saturated aqueous solution of sodium hydrogencarbonate, and dried over anhydrous sodium sulfate. The solvent was distilled away from the mixture under reduced pressure. The residue was chromatographed on a silica gel column for purification, whereby 1.39 g (80%) of the captioned compound with an optical rotation of $[\alpha]_D^{25}=+14.6°$ (c=0.5327, ethanol) was obtained. Furthermore, the captioned compound with the following physical properties was obtained by recrystallization.

Melting point (°C.) 140.9–142.4

IR (vcm$^{-1}$, KBr) 3328, 1742, 1682, 1532, 1352

Mass spectrometry Based on Formula $C_{22}H_{27}N_3O_7$ Calcd. 445.18484 Found 445.18726

NMR (δ, CDCl$_3$) 1.44 (9H, s), 2.31 (3H, s), 2.34 (3H, s), 3.66 (3H, s), 3.88 (2H, d, J=5 Hz), 4.96 (1H, s), 5.62 (1H, s), 5.86 (1H, t, J=5 Hz), 7.42 (1H, dd, J=8 Hz, 8 Hz), 7.69 (1H, d, J=8 Hz), 8.04 (1H, d, J=8 Hz), 8.13 (1H, s)

Optical rotation $[\alpha]_D^{25}=+18.3°$ [c=1.0264, ethanol]

EXAMPLE 97

Synthesis of (−)-t-butyl (R)-[2-[N-[1,4-dihydro-2,6-dimethyl-5-methoxycarbonyl-4-(3-nitrophenyl)pyridin-3-yl]carbonyl]amino]acetate:

The above compound was synthesized in accordance with the following reaction scheme:

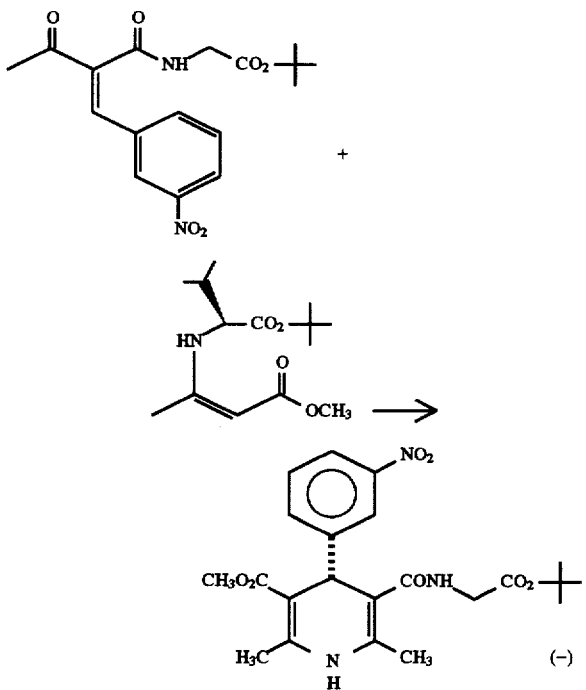

The procedure for the synthesis of (+)-t-butyl (S)-[2-[N-[1,4-dihydro-2,6-dimethyl-5-methoxycarbonyl-4-(3-nitrophenyl)pyridine-3-yl]carbonyl]amino]acetate in Example 96 was repeated except that the (−)-methyl (R)-[N-[1 (t-butoxycarbonyl)-2-methylpropyl]]aminocrotonate employed in Example 96 was replaced by 1.194 g (4.4 mmol) of (+)-methyl (S)-[N-[1-t-butoxycarbonyl)-2-methylpropyl]]aminocrotonate, whereby 1.39 g (80%) of the captioned compound with an optical rotation of $[\alpha]_D^{25}=+15.2°$ [c=0.5001, ethanol] was obtained. Furthermore, the captioned compound with the following physical properties was obtained by recrystallization.

Melting point (°C.) 140.0–141.8

IR (vcm$^{-1}$, KBr) 3328, 1742, 1682, 1532, 1352

Mass spectrometry $C_{22}H_{27}N_3O_7$ Calcd. 445.18484 Found 445.18655

NMR (δ, CDCl$_3$) 1.44 (9H, s), 2.31 (3H, s), 2.34 (3H, s), 3.66 (3H, s), 3.88 (2H, d, J=5 Hz), 4.96 (1H, s), 5.62 (1H, s), 5.86 (1H, t, J=5 Hz), 7.42 (1H, dd, J=8 Hz, 8 Hz), 7.69 (1H, d, J=8 Hz), 8.04 (1H, d, J=8 Hz), 8.13 (1H, S)

Optical rotation $[\alpha]_D^{25}=-18.4°$ [c=1.053, ethanol]

Reference Example 15

Synthesis of (+)-t-butyl (S)-2-[N-[3-[N-[1-(t-butoxycarbonyl)-2-methylpropyl]amino]-2-butenoyl]amino]-acetate:

A mixture of 4.305 g (20 mmol) of t-butyl 2-[N-(3-oxobutanoyl)amino]acetate and 3.811 g (22 mmol) of L-valine t-butyl ester was stirred at room temperature for 15 hours. The reaction mixture was dissolved in benzene and dried over anhydrous sodium sulfate. The solvent was distilled away from the reaction mixture under reduced pressure, whereby 7.41 g (100%) of the captioned compound was obtained.

Optical rotation $[\alpha]_D^{25}=+114.5°$ [c=0.9415, ethanol]

NMR (δ, CDCl$_3$) 1.00 (6H, d, J=7 Hz), 1.46 (18H, s), 1.81 (3H, s), 2.08–2.22 (1H, m), 3.71 (1H, dd, J=10 Hz, 6 Hz), 3.95 (2H, d, J=5 Hz), 4.41 (1H, s), 5.29 (1H, t, J=5 Hz), 9.33 (1H, d, J=10 Hz)

Reference Example 16

Synthesis of (−)-t-butyl (R)-2-[N-[3-[N-[1-(t-butoxycarbonyl)-2-methylpropyl]amino]-2-butenoyl]amino]-acetate:

A mixture of 4.305 g (20 mmol) of t-butyl 2-[N-(3-oxobutanoyl)aminocrotonate]acetate and 3.811 g (22 mmol) of D-valine t-butyl ester was stirred at room temperature for 15 hours. The reaction mixture was dissolved in benzene and dried over anhydrous sodium sulfate. The solvent was distilled away under reduced pressure, whereby 7.41 g (100%) of the captioned compound was obtained.

Optical rotation $[\alpha]_D^{25}=-114.5°$ [c=0.8447, ethanol]

NMR (δ, CDCl$_3$) 1.00 (6H, d, J=7 Hz), 1.46 (18H, s), 1.81 (3H, s), 2.08–2.22 (1H, m), 3.71 (1H, dd, J=10 Hz, 6 Hz), 3.95 (2H, d, J=5 Hz), 4.41 (1H, s), 5.29 (1H, t, J=5 Hz), 9.33 (1H, d, J=10 Hz)

EXAMPLE 98

Synthesis of (+)-t-butyl (S)-[2-[N-[1,4-dihydro-2,6-dimethyl-5-methoxycarbonyl-4-(3-nitrophenyl)pyridin-3-yl]-carbonyl]amino]acetate:

The above compound was synthesized in accordance with the following reaction scheme:

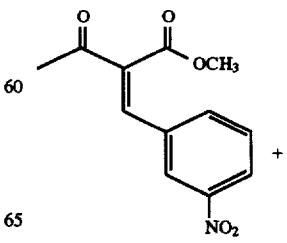

-continued

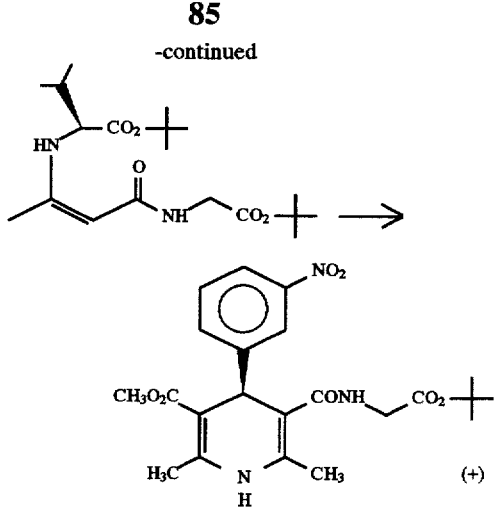

More specifically, a tetrahydrofuran solution containing phenylmagnesiumbromide in an amount of 1.2 equivalents was prepared by dissolving 0.656 g (27 mg atom) of magnesium, 0.188 g (1 mmol) of 1,2-dibromoethane and 3.768 g (24 mmol) of bromobenzene in 24 ml of anhydrous tetrahydrofuran. In an atmosphere of argon gas, the tetrahydrofuran solution containing the phenylmagnesiumbromide was added dropwise to 74 ml of an anhydrous tetrahydrofuran solution containing 7.41 g (20 mmol) of (+)-t-butyl (S)-2-[N-[3-[N-[(1-t-butoxycarbonyl)-2-methylpropyl] amino]-2-butenoyl]amino]acetate at −15° C. and the reaction mixture was stirred for one hour. The reaction mixture was cooled to −50° C. and an anhydrous tetrahydrofuran solution containing 4.735 g (19 mmol) of methyl 2-(3-nitrobenzylidene) acetoacetate was added dropwise thereto. After the completion of the dropwise addition of the tetrahydrofuran solution, the reaction mixture was further stirred for 3 hours. To the obtained reaction mixture, 47 ml of 1N hydrochloric acid was added dropwise and the temperature of the reaction mixture was raised to room temperature. An organic layer was separated from the reaction mixture. A water layer was extracted with tetrahydrofuran. The layer extracted with tetrahydrofuran was combined with the organic layer, washed with a saturated aqueous solution of sodium chloride and dried over anhydrous sodium sulfate. The solvent was distilled away from the mixture under reduced pressure. The residue was dissolved in 89 ml of methanol. With the addition of 15.4 g (200 mmol) of ammonium acetate, the residue was stirred at room temperature overnight. The solvent was distilled away from the mixture under reduced pressure. The residue was chromatographed on a silica gel column for purification, whereby 6.764 g (80%) of the captioned compound with an optical rotation of $[\alpha]_D^{25}=+16.1°$ (c=0.499, ethanol) was obtained. Furthermore, the captioned compound with the following physical properties was obtained by recrystallization.

Melting point (°C.) 140.9–142.4

IR (vcm$^{-1}$, KBr) 3328, 1742, 1682, 1532, 1352

Mass spectrometry Based on Formula $C_{22}H_{27}N_3O_7$ Calcd. 445.18484 Found 445.18726

NMR (δ, CDCl$_3$) 1.44 (9H, s), 2.31 (3H, s), 2.34 (3H, s), 3.66 (3H, s), 3.88 (2H, d, J=5 Hz), 4.96 (1H, s), 5.62 (1H, s), 5.86 (1H, t, J=5 Hz), 7.42 (1H, dd, J=8 Hz, 8 Hz), 7.69 (1H, d, J=8 Hz), 8.04 (1H, d, J=8 Hz), 8.13 (1H, s)

Optical rotation $[\alpha]_D^{25}=+18.3°$ [c=1.0264, ethanol]

EXAMPLE 99

Synthesis of (−)-t-butyl (R)-[2-[N-[1,4-dihydro-2,6-dimethyl-5-methoxycarbonyl-4-(3-nitrophenyl)pyridine-3-yl]-carbonyl]amino]acetate:

The above compound was synthesized in accordance with the following reaction scheme:

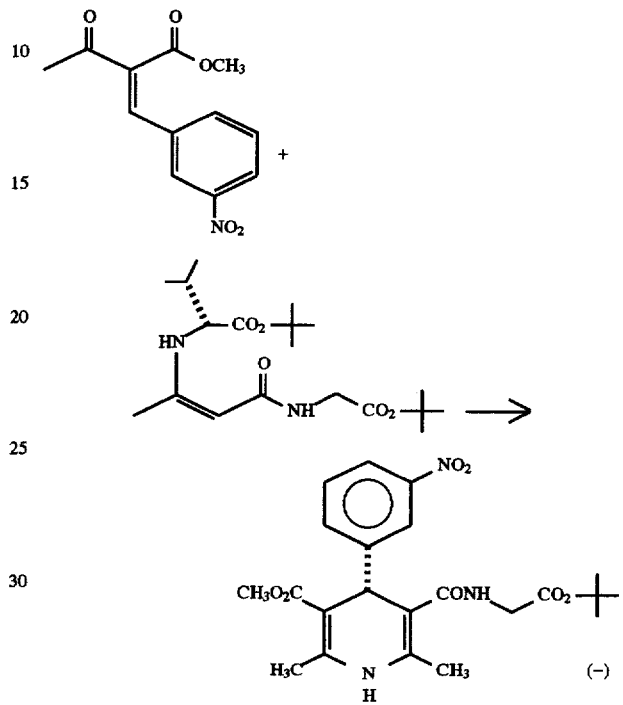

The procedure for the synthesis of (+)-t-butyl (s)-[2-[N-[1,4-dihydro-2,6-dimethyl-5-methoxycarbonyl-4-(3-nitrophenyl)pyridin-3-yl]carbonyl]amino]acetate in Example 98 was repeated except that (+)-t-butyl (S)-2-[N-[3-[N-[(1-t-butoxycarbonyl)-2-methylpropyl]amino]-2-butenoyl]amino]acetate employed in Example 98 was replaced by 7.41 g (20 mmol) of (−)-t-butyl (R)-2-[N-[3-[N-[(1-t-butoxycarbonyl)-2-methylpropyl]amino]-2-butenoyl]-amino]acetate, whereby 6.764 g (80%) of the captioned compound with an optical rotation of $[\alpha]_D^{25}=-15.8°$ (c=0.499, ethanol) was obtained. Successively, the captioned compound with the following physical properties was obtained by recrystallization.

Melting point (°C.) 140.0–141.8

IR (vcm$^{-1}$, KBr) 3328, 1742, 1682, 1532, 1352

Mass spectrometry Based on Formula $C_{22}H_{27}N_3O_7$ Calcd. 445.18484 Found 445.18655

NMR (δ, CDCl$_3$) 1.44 (9H, s), 2.31 (3H, s), 2.34 (3H, s), 3.66 (3H, s), 3.88 (2H, d, J=5 Hz), 4.96 (1H, s), 5.62 (1H, s), 5.86 (1H, t, J=5 Hz), 7.42 (1H, dd, J=8 Hz, 8 Hz), 7.69 (1H, d, J=8 Hz), 8.04 (1H, d, J=8 Hz), 8.13 (1H, s)

Optical rotation $[\alpha]_D^{25}=-18.4°$ [c=1.053, ethanol]

EXAMPLE 100

Synthesis of t-butyl 2-[N-(5-cyano-1,4-dihydro-2,6-dimethyl-4-(3-nitrophenyl)pyridine-3-carbonyl)amino] acetate:

The above compound was synthesized in accordance with the following reaction scheme:

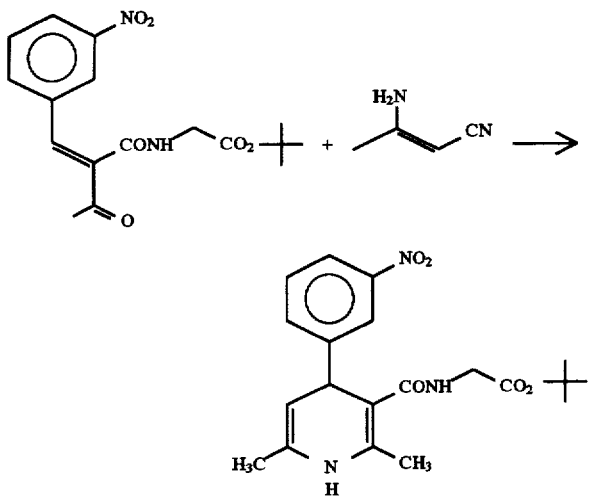

A toluene solution containing 348 mg (1 mmol) of t-butyl 2-[N-[3-oxo-2-(3-nitrobenzylidene)butanoyl]amino]acetate and 123 mg (1.5 mmol) of 3-aminocrotonitrile was refluxed for 4 hours. The reaction mixture was chromatographed on a silica gel column for purification, whereby 407 mg (98.7%) of t-butyl 2-[N-(5-cyano-1,4-dihydro-2,6-dimethyl-4-(3-nitro-phenyl)pyridine-3-carbonyl)amino]acetate was obtained.

Melting point (°C.) 181.8–183.1

IR (vcm$^{-1}$, KBr) 3308, 2196, 1706, 1676, 1526, 1352

Mass spectrometry Based on Formula $C_{21}H_{24}N_4O_5$ Calcd. 412.17464 Found 412.17500

NMR (δ, CDCl$_3$) 1.42 (9H, s), 2.12 (3H, s), 2.28 (3H, s), 3.78 (1H, dd, J=18 Hz, 6 Hz), 3.87 (1H, dd, J=18 Hz, 6 Hz), 4.69 (1H, s), 5.76 (1H, t, J=6 Hz), 5.81 (1H, s), 7.52 (1H, dd, J=8H, 8 Hz), 7.68 (1H, d, J=8 Hz), 8.12 (1H, s), 8.14 (1H, d, J=8 Hz)

1. Test for hypotensive activity

The test was carried out by employing spontaneously hypertensive rats (aparalytice SHR; male) according to Nakao et al method.

The blood pressures in the whole body of the rats were measured with a pressure transducer (MPU-0.5, made by Nihon Koden K. K.) through a canula inserted into the abdominal aorta through the aorta of its tail. Successively, 100 μg/kg of each compound to be tested was administrated into the vein of its tail of SHR through a canula (previously inserted), whereby the hypotensive activiy of each compound was examined. The results are shown in Table 10.

TABLE 10

| Compound of Example | Hypotensive Activity (mmHg) |
|---|---|
| 1 (Compound a) | 90 |
| 1 (Compound b) | 105 |
| 2 (Compound a) | 35 |
| 2 (Compound b) | 35 |
| 3 | 40 |
| 4 | 105 |
| 7 | 80 |
| 8 | 25 |
| 9 | 100 |
| 12 | 75 |
| 13 (Compound b) | 90 |
| 15 | 90 |

TABLE 10-continued

| Compound of Example | Hypotensive Activity (mmHg) |
|---|---|
| 22 (Compound a) | 90 |
| 23 | 70 |
| 32 | 60 |
| 34 | 30 |
| 35 | 50 |
| 36 | 35 |
| 37 | 30 |
| 38 | 20 |
| 48 | 92.5 |
| 49 | 105 |
| 50 (Compound a) | 107.5 |
| 66 | 30 |
| 90 | 70 |

2. Test for platelet aggregation-inhibiting activity of rabit

A blood of a rabbit (Japanese white; male; 2.5–3.0 kg) was exsanguinated from a carotid of the rabbit, and nine parts of the blood were mixed with one part of a 3.8% aqueous solution of sodium citrate. The mixture was centrifuged at 1100 rpm at 20° C. for 15 minutes. The upper layer is a platelet rich plasma (PRP), and the lower layer was centrifuged at 2500 rpm at 20° C. for 10 minutes, so that a platelet poor plasma (PPP) was obtained.

10 μl of a solution of the compound to be tested was added to 200 μl of PRP, and the mixture was subjected to incubation at 37° C. for 10 minutes. To the mixture was added 10 μl of a platelet activating factor (PAF) (10 mg/ml). The agglutination was measured by Agricometer (NKK, PAT-4A). The Platelet aggregation-inhibiting concentration to each aggregation agent of each compound is shown in Table 11.

TABLE 11

| Compound of Example | Platelet Aggregation-Inhibiting Activity (%) |
|---|---|
| 1 (Compound a) | 42.8 |
| 2 (Compound a) | 25.5 |
| 2 (Compound b) | 98.2 |
| 3 | 100 |
| 7 (Compound a) | 54.1 |
| 8 | 39.1 |
| 9 | 29.8 |
| 13 (Compound a) | 37.7 |
| 18 (Compound a) | 33.8 |
| 19 (Compound a) | 35.4 |
| 22 (Compound a) | 20.2 |
| 23 | 33.6 |
| 24 (Compound a) | 24.3 |
| 27 (Compound a) | 33.3 |
| 32 | 100 |
| 33 | 94.2 |
| 34 | 100 |
| 35 | 32.3 |
| 36 | 100 |
| 37 | 100 |
| 38 | 100 |
| 47 | 32.7 |
| 48 | 41.5 |
| 49 | 38.9 |
| 50 (Compound a) | 23.5 |
| 52 (Compound a) | 29.2 |
| 57 | 64.5 |
| 58 | 22.1 |
| 60 | 47.2 |
| 62 | 64.3 |
| 63 | 100 |
| 64 | 52.6 |
| 65 | 42.7 |

TABLE 11-continued

| Compound of Example | Platelet Aggregation-Inhibiting Activity (%) |
|---|---|
| 66 | 100 |
| 67 | 33.8 |
| 68 | 34.1 |
| 69 | 23.3 |
| 70 | 27.1 |
| 71 | 100 |
| 76 | 46.3 |
| 79 | 100 |

The 1,4-dihydropyridine derivatives and optical active 1,4-dihydropyridine derivatives according to the present invention have vasodilating activity based on calcium antagonism, and PAF antaognism, so that these 1,4-dihydropyridine derivatives are useful as remedies for diseases of circulatory system, such as hypotensor, cerebral circulation improvement agent, and antithrombotic agent, and remedies for allergic diseases, such as antiasthmatic, anti-inflammatory agent, and antiallergic agent. Furthermore, the present invention provides simple and efficient methods of producing the optical active 1,4-dihydropyridine derivatives.

What is claimed is:

1. A method of producing optically active 1,4-dihydropyridine derivatives of formula (I-a) comprising the steps of:

(a) allowing an N-acylamino acid derivative of formula (XIV) to react with an optically active enamine derivative of formula (XV), and (b) allowing a product of its reaction to react with ammonia or an ammonium salt:

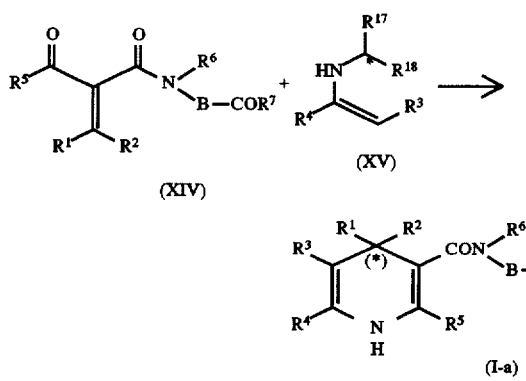

wherein $R^1$ represents hydrogen, a straight chain, branched chain or cyclic alkyl group having from 1 to 6 carbon atoms, an unsubstituted or substituted aromatic hydrocarbon group, or an unsubstituted or substituted aromatic heterocyclic group; $R^2$ represents hydrogen, a straight chain, branched chain or cyclic alkyl group having from 1 to 6 carbon atoms, and $R^1$ and $R^2$ in combination may form a saturated or unsaturated hydrocarbon ring; $R^4$ and $R^5$ each represent hydrogen, an unsubstituted or substituted straight chain, branched chain or cyclic alkyl group having from 1 to 6 hydrocarbon atoms, an unsubstituted or substituted amino group, an unsubstituted or substituted aromatic hydrocarbon group, or an unsubstituted or substituted aromatic heterocyclic group; $R^6$ represents hydrogen, a straight chain, branched chain or cyclic alkyl group having from 1 to 6 carbon atoms; or a trialkylsilyl group; B represents an unsubstituted or substituted alkylene group, an unsubstituted or substituted aromatic hydrocarbon group, an unsubstituted or substituted aromatic heterocyclic group, an unsubstituted or substituted cylcoalkylydene group; $R^7$ represents an unsubstituted or substituted straight chain, branched chain or cyclic alkoxyl group, an unsubstituted or substituted amino group, or an unsubstituted or substituted cyclic amino group; $R^3$ represents hydrogen, cyano group, nitro group, $-COR^8$, an unsubstituted or substituted aromatic hydrocarbon group, or an unsubstituted or substituted aromatic heterocyclic group, in which $R^8$ represents an unsubstituted or substituted straight chain, branched chain or cyclic alkoxyl group, an alkenyloxy group, an alkylnyloxy group, or $-N(R^{61})-B^1-COR^{71}$, in which $R^{61}$, $R^{71}$ and $B^1$ are respectively the same as $R^6$, $R^7$ and B; $R^{17}$ and $R^{18}$ are different and independently represent an unsubstituted or substituted straight chain, branched chain or cyclic alkyl group, an unsubstituted or substituted aromatic hydrocarbon group, an unsubstituted or substituted aralkyl group, an unsubstituted or substituted straight chain, branched chain or cyclic alkoxycarbonyl group, or an unsubstituted or substituted straight chain, branched chain or cyclic aminocarbonyl group, and * indicates a chiral center.

2. The method as claimed in claim 1, wherein said straight chain, branched chain or cyclic alkyl group having 1 to 6 atoms represented by $R^1$, $R^2$, $R^4$, $R^5$, or $R^6$ is selected from the group consisting of methyl group, ethyl group, propyl group, butyl group, pentyl group, hexyl group, 2-propyl group, t-butyl group, cyclopentyl group, and cyclohexyl group.

3. The method as claimed in claim 1, wherein said unsubstituted or substituted aromatic hydrocarbon group, or said unsubstituted or substituted aromatic heterocyclic group represented by $R^1$, $R^4$, $R^5$, or $R^6$ is selected from the group consisting of phenyl group, pyridyl group, quinolyl group, isoquinolyl group, furyl group, thienyl group, benzoxazolyl group, benzthiazolyl group, pyridazinyl group, pyrazinyl group, pyrimidyl group, indolyl group, naphthyl group, benzoxadiazolyl group, and benzthiadiazolyl group, which may have a substituent.

4. The method as claimed in claim 3, wherein said substituent of said unsubstituted or substituted aromatic hydrocarbon group, or said unsubstituted or substituted aromatic heterocyclic group represented by $R^1$ is selected from the group consisting of a halogen atom, hydroxyl group, cyano group, nitro group, trifluoromethyl group, trichloromethyl group, azide group, amino group; a lower alkyl group having 1 to 6 carbon atoms, a lower alkoxyl group having 1 to 6 carbon atoms, a lower alkylthio group having 1 to 6 carbon atoms, phenylthio group, phenoxy group, methoxycarbonyl group, ethoxycarbonyl group, propoxycarbonyl group, butoxycarbonyl group, pentyloxycarbonyl group, acetyl group, propionyl group, butylyl group, pentanolyl group, hexanolyl group, benzyloxy group, and cinnamyloxy group.

5. The method as claimed in claim 1, wherein said saturated or unsaturated hydrocarbon ring formed by $R^1$ and $R^2$ in combination is selected from the group consisting of cyclopentane ring, cyclohexane ring, and tetrahydronaphthalene ring.

6. The method as claimed in claim 1, wherein said substituted straight chain, branched chain or cyclic alkyl group represented by $R^4$ or $R^5$ is selected from the group consisting of trifluoromethyl group, and trichloromethyl group.

7. The method as claimed in claim 1, wherein said unsubstituted or substituted amino group represented by $R^4$ or $R^5$ is selected from the group consisting of amino group, dimethylamino group, diethylamino group, and dipropylamino group.

8. The method as claimed in claim 1, wherein said unsubstituted or substituted straight chain, branched chain or cyclic alkoxyl group represented by $R^7$ is selected from the group consisting of methoxy group, ethoxy group, n-propyloxy group, n-butoxy group, n-pentyloxy group, n-hexyloxy group, n-heptyloxy group, n-octyloxy group, n-nonyloxy group, n-decyloxy group, isopropyloxy group, isobutyloxy group, cyclopentyloxy group, cyclohexyloxy group, aryloxy group, 2-propyn-1-yloxy group, (E)-2-buten-1-yloxy group, (E)-3-buten-1-yloxy group, (E)-2-penten-1-yloxy group, (2E,4E)-2,4-hexadienyloxy group, 2,4-hexadiynyloxy group, (E)-hexa-4-ene-2-ynoxy group, (E)-3-phenyl-2-propen-1-yloxy group, (Z)-3-phenyl-2-propen-1-yloxy group, 3-phenyl-2-propyn-1-yloxy group, (2E,4E)-5-phenyl-2,4-pentadien-1-yloxy group, 5-phenyl-penta-2,4-diyn-1-yloxy group, (E)-5-phenyl-penta-2-ene-4-yn-1-yloxy group, (E)-3-[4-(1-imidazolylmethyl)phenyl]-2-propen-1-yloxy group, (E)-3-[3-(1-imidazolylmethyl)phenyl]-2-propen-1-yloxy group, (E)-3-[2-(1-imidazolylmethyl)phenyl]-2-propen-1-yloxy group, (E)-3-[4-(1-imidazolyl)phenyl]-2-propen-1-yloxy group, (Z)-3-[4-(1-imidazolylmethyl)phenyl]-2-propen-1-yloxy group, (E)-3-[6-(1-imidazolylmethyl)pyridin-2-yl]-2-propen-1-yloxy group, (E)-3-[5-(1-imidazolylmethyl)furan-2-yl]-2-propenlyloxy group, (E)-3-[5-(1-imidazolylmethyl)thiophen-2-yl]-2-propen-1-yloxy group, (E)-3-phenyl-1-methyl-2-propen-1-yloxy group, (E)-1-fluoro-3-phenyl-2-propen-1-yloxy group, 2-methoxyethyloxy group, 3-methoxypropyloxy group, 3-ethoxypropyloxy group, 2-phenoxyethyloxy group, 2-phenylthioethyloxy group, 2-(N-methylamino)ethyloxy group, 2-(N,N-dimethylamino)ethyloxy group, 2-(N-methyl-N-phenylamino)ethyloxy group, 2-(N,N-diethyl)aminoethyloxy group, 2-(N-benzyl-N-methyl)aminoethyloxy group, 2-(1-piperazinyl)ethyloxy group, 4-(1-piperazinyl)butyloxy group, 6-(1-piperazinyl) hexyloxy group, 2-(4-piperidinyl)ethyloxy group, 2-(4-phenylpiperazin-1-yl)ethyloxy group, D-(4-phenylpiperazin-1-yl)propyloxy group, 4-(4-phenylpiperazin-1-yl) butyloxy group, 6-(4-phenylpiperazin-1-yl)hexyloxy group, 2-(4-phenylpiperidin-1-yl)ethyloxy group, 3-(4-phenylpiperidin-1-yl) propyloxy group, 4-(4-phenylpiperidin-1-yl)butyloxy group, 6-(4-phenylpiperidin-1-yl)hexyloxy group, 2-[4-(diphenylmethyl)piperazin-1-yl]ethyloxy group, 3-[4-(diphenylmethyl)-piperazin-1-yl]propyloxy group, 4-[4-(diphenylmethyl)piperazin-1-yl]butyloxy group, 6-[4-(diphenylmethyl)piperazin-1-yl]hexyloxy group, 2-morpholinoethyloxy group, N-benzylpyrrolidin-3-yloxy group, N-benzylpiperidin-3-yloxy group, 2-(1,2,3,4-tetrahydroisoquinolin-2-yl)ethyloxy group, 2,2,2-trifluoroethyloxy group, 2-(3,7-dihydro-3,7-dimethyl-1H-purine-2,6-dion-1-yl)ethyloxy group, and 2-(1,2,3,6-tetrahydro-1,3-dimethyl-2,6-dioxo-7H-purin-7-yl)ethyloxy.

9. The method as claimed in claim 1, wherein said unsubstituted or substituted amino group or cyclic amino group is selected from the group consisting of dimethylamino group, diethylamino group, dipropylamino group, diisopropylamino group, piperidinyl group, piperazinyl group, morpholino group, pyrrolidinyl group, 4-phenylpiperidinyl group, 4-phenylpiperazinyl group, 4-diphenylmethylpiperazinyl group, methoxycarbonylmethylamino group, ethoxycarbonylmethylamino group, isopropyloxycarbonylmethylamino group, t-butoxycarbonylmethylamino group, 1-(t-butoxycarbonyl)-2-methylpropylamino group, 1-(t-butoxycarbonyl) ethylamino group, 1-(t-butoxycarbonyl)-2-phenylethylamino group, 1-(2-methoxyethoxycarbonyl)-2-methylpropylamino group, 1-(ethoxycarbonyl)-1-methylethylamino group, 2-(ethoxycarbonyl)ethylamino group, and N-methyl-N-ethoxycarbonylmethylamino group.

* * * * *

UNITED STATES PATENT AND TRADEMARK OFFICE
CERTIFICATE OF CORRECTION

PATENT NO. : 5,696,268
DATED : December 9, 1997
INVENTOR(S) : Hiroshi Ikawa, et al.

It is certified that error appears in the above-identified patent and that said Letters Patent is hereby corrected as shown below:

Column 2, line 12, "besed" should read -- based --.

Column 3, line 30,

"

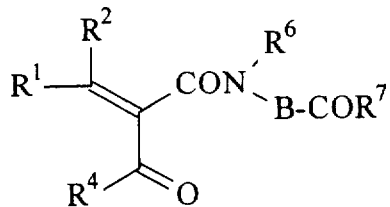

(IV)

", should read

--

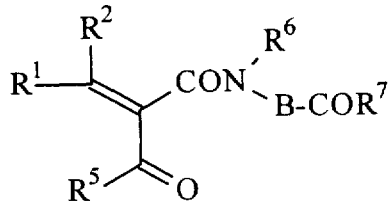

(IV)

--.

UNITED STATES PATENT AND TRADEMARK OFFICE
CERTIFICATE OF CORRECTION

PATENT NO. : 5,696,268
DATED : December 9, 1997
INVENTOR(S) : Hiroshi Ikawa, et al.

It is certified that error appears in the above-identified patent and that said Letters Patent is hereby corrected as shown below:

Column 4, line 35, "grup" should read -- group --.

Column 5, line 34, "i" should read -- 1 --.

Column 5, line 39, "methythio" should read -- methylthio -- .

Column 6, line 17, "isopropytoxy" should read -- isopropyloxy --.

Column 12, line 55, "diemthyl" should read -- dimethyl --.

Column 13, line 9,

"

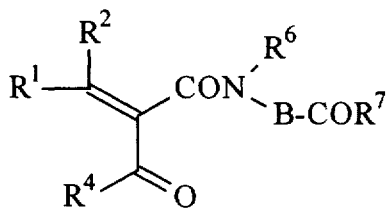

(IV)

"

UNITED STATES PATENT AND TRADEMARK OFFICE
CERTIFICATE OF CORRECTION

PATENT NO. : 5,696,268
DATED : December 9, 1997
INVENTOR(S) : Hiroshi Ikawa, et al.

It is certified that error appears in the above-identified patent and that said Letters Patent is hereby corrected as shown below:

-- should read

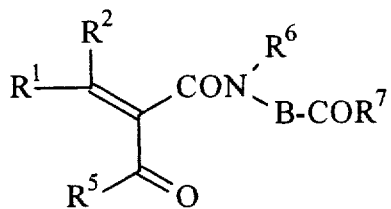

(IV)

--.

Column 13, line 40, "diemthyl" should read -- dimethyl --.

Column 16, line 10, "XT'" should read -- (XI') --.

UNITED STATES PATENT AND TRADEMARK OFFICE
CERTIFICATE OF CORRECTION

PATENT NO. : 5,696,268
DATED : December 9, 1997
INVENTOR(S) : Hiroshi Ikawa, et al.

It is certified that error appears in the above-identified patent and that said Letters Patent is hereby corrected as shown below:

Column 17, line 15,

"
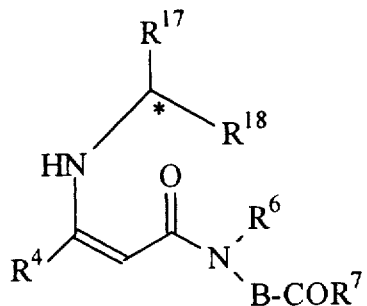
"

should read

--
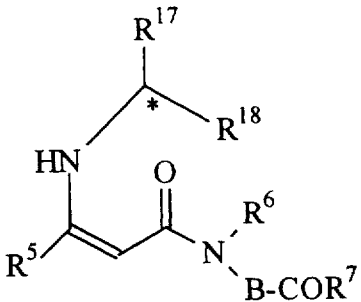
--.

UNITED STATES PATENT AND TRADEMARK OFFICE
CERTIFICATE OF CORRECTION

PATENT NO. : 5,696,268
DATED : December 9, 1997
INVENTOR(S) : Hiroshi Ikawa, et al.

It is certified that error appears in the above-identified patent and that said Letters Patent is hereby corrected as shown below:

Column 18, line 20, "as" should read -- was --.

Column 24, line 29, "7.08 ∝ 7.32" should read -- 7.08-7.32 --.

Column 25, line 14, "(νK Br, cm )" should read -- (νKBr, cm$^{-1}$ ) --.

Column 26, line 60,

"
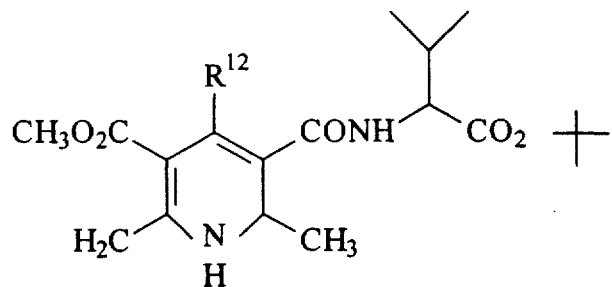
"

UNITED STATES PATENT AND TRADEMARK OFFICE
CERTIFICATE OF CORRECTION

PATENT NO. : 5,696,268
DATED : December 9, 1997
INVENTOR(S) : Hiroshi Ikawa, et al.

It is certified that error appears in the above-identified patent and that said Letters Patent is hereby corrected as shown below:

Column 30, line 35,

"  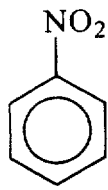  "

should read

-- 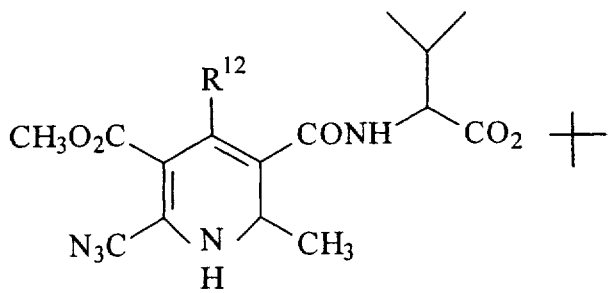 --.

UNITED STATES PATENT AND TRADEMARK OFFICE
CERTIFICATE OF CORRECTION

PATENT NO. : 5,696,268
DATED : December 9, 1997
INVENTOR(S) : Hiroshi Ikawa, et al.

It is certified that error appears in the above-identified patent and that said Letters Patent is hereby corrected as shown below:

should read

--

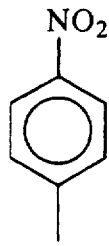

--.

Column 30, line 59, "Exhale" should read -- Example --.

Column 31, line 36, "2..29" should read -- 2.29 --.

Column 32, line 27, "(VBr, cm)" should read -- ($\vee K\,Br, cm^{-1}$) --.

Column 34, lines 8-9,

"

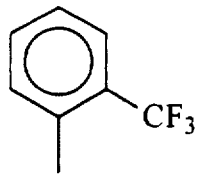

"

UNITED STATES PATENT AND TRADEMARK OFFICE
CERTIFICATE OF CORRECTION

PATENT NO. : 5,696,268
DATED : December 9, 1997
INVENTOR(S) : Hiroshi Ikawa, et al.

It is certified that error appears in the above-identified patent and that said Letters Patent is hereby corrected as shown below:

should read

-- 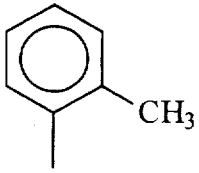

--.

Column 38, line 39, "$C_{24}H_{31}N_3)_8$" should read -- $C_{24}H_{31}N_3O_8$ --.

Column 40, line 19, "J=8 Hz)" should read -- J=5Hz) --.

Column 43, line 38, "8,03" should read -- 8.03 --.

Column 48, line 30, "(4-diphenytmethylpiperazinyl)" should read -- (4-diphenylmethylpiperazinyl) --.

Column 53, line 54,

" 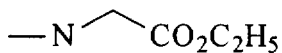

"

UNITED STATES PATENT AND TRADEMARK OFFICE
CERTIFICATE OF CORRECTION

PATENT NO. : 5,696,268
DATED : December 9, 1997
INVENTOR(S) : Hiroshi Ikawa, et al.

It is certified that error appears in the above-identified patent and that said Letters Patent is hereby corrected as shown below:

should read

--

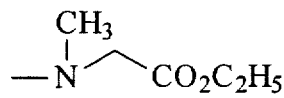

--.

Column 54, line 34, "chlotocarbonate" should read

-- chlorocarbonate --.

Column 56, line 36, "raction" should read -- reaction --.

UNITED STATES PATENT AND TRADEMARK OFFICE
CERTIFICATE OF CORRECTION

PATENT NO. : 5,696,268
DATED : December 9, 1997
INVENTOR(S) : Hiroshi Ikawa, et al.

It is certified that error appears in the above-identified patent and that said Letters Patent is hereby corrected as shown below:

Column 57, line 40,

"
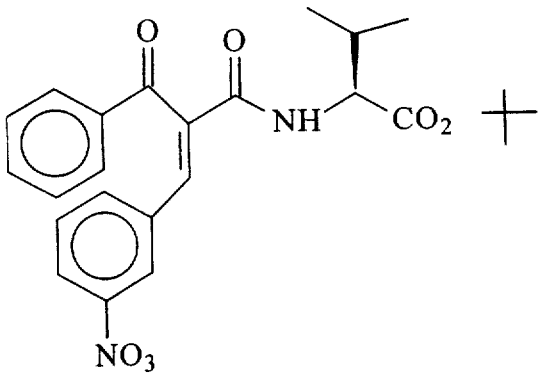
"

should read

UNITED STATES PATENT AND TRADEMARK OFFICE
CERTIFICATE OF CORRECTION

PATENT NO. : 5,696,268
DATED : December 9, 1997
INVENTOR(S) : Hiroshi Ikawa, et al.

It is certified that error appears in the above-identified patent and that said Letters Patent is hereby corrected as shown below:

--

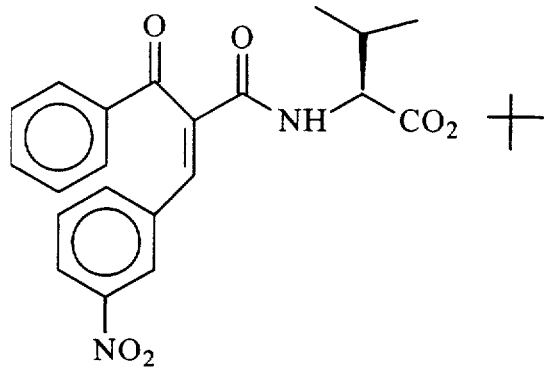

--.

Column 59, line 65, "(1H, S)" should read -- (1H, s) --.

UNITED STATES PATENT AND TRADEMARK OFFICE
CERTIFICATE OF CORRECTION

Page 12 of 15

PATENT NO. : 5,696,268
DATED : December 9, 1997
INVENTOR(S) : Hiroshi Ikawa, et al.

It is certified that error appears in the above-identified patent and that said Letters Patent is hereby corrected as shown below:

Column 63, lines 9-10,

"
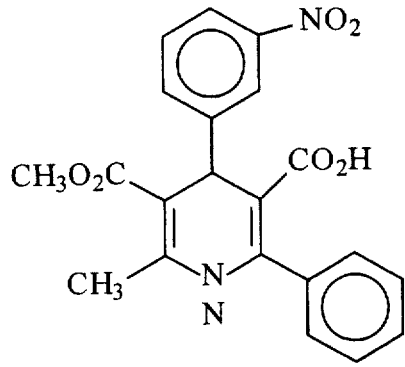
"

UNITED STATES PATENT AND TRADEMARK OFFICE
CERTIFICATE OF CORRECTION

Page 13 of 15

PATENT NO. : 5,696,268
DATED : December 9, 1997
INVENTOR(S) : Hiroshi Ikawa, et al.

It is certified that error appears in the above-identified patent and that said Letters Patent is hereby corrected as shown below:

should read

--

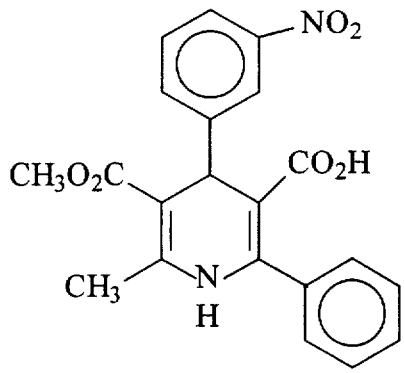

--.

Column 68, line 39, "then," should read -- then --.

Column 71, line 43, "82." should read -- 82 --.

Column 78, line 45, "3320, 1740 1680, 1530 1350" should read -- 3320, 1740, 1680, 1530, 1350 --.

Column 79, line 11, "3330, 1740 1690 1530, 1350" should read -- 3330, 1740, 1690, 1530, 1350 --.

UNITED STATES PATENT AND TRADEMARK OFFICE
CERTIFICATE OF CORRECTION

PATENT NO. : 5,696,268
DATED : December 9, 1997
INVENTOR(S) : Hiroshi Ikawa, et al.

Page 14 of 15

It is certified that error appears in the above-identified patent and that said Letters Patent is hereby corrected as shown below:

Column 87, lines 19-20,

"
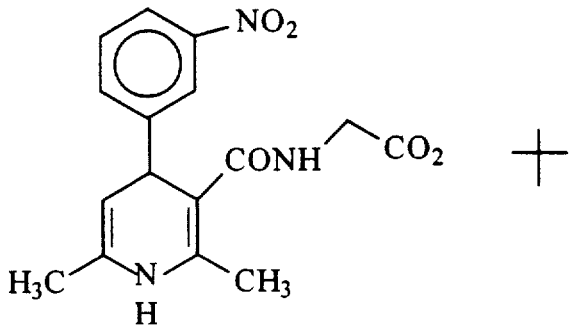

UNITED STATES PATENT AND TRADEMARK OFFICE
CERTIFICATE OF CORRECTION

PATENT NO. : 5,696,268
DATED : December 9, 1997
INVENTOR(S) : Hiroshi Ikawa, et al.

Page 15 of 15

It is certified that error appears in the above-indentified patent and that said Letters Patent is hereby corrected as shown below:

"

should read
--

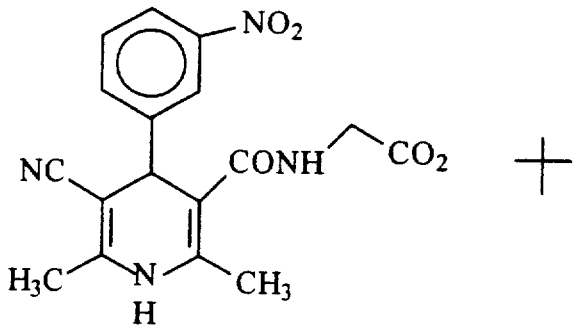

--.

Signed and Sealed this

Fourteenth Day of July, 1998

Attest:

BRUCE LEHMAN

*Attesting Officer*                *Commissioner of Patents and Trademarks*